(12) United States Patent
Kawashima et al.

(10) Patent No.: US 9,618,666 B2
(45) Date of Patent: Apr. 11, 2017

(54) NEAR-INFRARED-ABSORBING COMPOSITION, NEAR-INFRARED CUT-OFF FILTER USING SAME, MANUFACTURING METHOD THEREFOR, CAMERA MODULE, AND MANUFACTURING METHOD THEREFOR

(71) Applicant: FUJIFILM Corporation, Tokyo (JP)

(72) Inventors: Takashi Kawashima, Shizuoka (JP); Seiichi Hitomi, Shizuoka (JP); Hidenori Takahashi, Shizuoka (JP); Yuki Nara, Shizuoka (JP); Seongmu Bak, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/753,189

(22) Filed: Jun. 29, 2015

(65) Prior Publication Data
US 2015/0301245 A1 Oct. 22, 2015

Related U.S. Application Data

(63) Continuation of application No. PCT/JP2014/052402, filed on Feb. 3, 2014.

(30) Foreign Application Priority Data

Feb. 19, 2013 (JP) ................................ 2013-030487
Jul. 24, 2013 (JP) ................................ 2013-153991

(51) Int. Cl.
| | | |
|---|---|---|
| *G02B 5/20* | (2006.01) | |
| *C07F 1/08* | (2006.01) | |
| *H04N 5/225* | (2006.01) | |
| *H04N 5/33* | (2006.01) | |
| *C08F 2/44* | (2006.01) | |
| *C08K 5/42* | (2006.01) | |
| *C08L 63/00* | (2006.01) | |
| *G02B 5/22* | (2006.01) | |
| *C08K 5/00* | (2006.01) | |
| *H01L 27/146* | (2006.01) | |

(52) U.S. Cl.
CPC ............... *G02B 5/208* (2013.01); *C07F 1/08* (2013.01); *C08F 2/44* (2013.01); *C08K 5/0091* (2013.01); *C08K 5/42* (2013.01); *C08L 63/00* (2013.01); *G02B 5/22* (2013.01); *G02B 5/223* (2013.01); *H01L 27/14618* (2013.01); *H01L 27/14625* (2013.01); *H04N 5/2254* (2013.01); *H04N 5/332* (2013.01); *H01L 2224/11* (2013.01)

(58) Field of Classification Search
CPC .......... C07F 1/08; G02B 5/208; G02B 5/223; G02B 5/22; H04N 5/332; H04N 5/2254; H01L 27/14625; H01L 27/14618; C08K 5/0091; C08K 5/42; C08F 2/44; C08L 63/00

USPC ............ 556/113; 252/587; 427/162; 348/342
See application file for complete search history.

(56) References Cited

U.S. PATENT DOCUMENTS

| | | |
|---|---|---|
| 4,567,753 A | 2/1986 | Miller, Jr. et al. |
| 5,354,514 A | 10/1994 | Satake et al. |
| 2001/0011719 A1 | 8/2001 | Hasegawa et al. |
| 2002/0068778 A1 | 6/2002 | Ohnishi et al. |
| 2004/0185588 A1 | 9/2004 | Fukuyoshi et al. |

FOREIGN PATENT DOCUMENTS

| | | |
|---|---|---|
| JP | 61-144567 A | 7/1986 |
| JP | 02-34682 A | 2/1990 |
| JP | 05-163408 A | 6/1993 |
| JP | 08-127763 A | 5/1996 |
| JP | 2001-213918 A | 8/2001 |
| JP | 2004200360 A | 7/2004 |
| JP | 2010-134457 A | 6/2010 |
| JP | 2011-100084 A | 5/2011 |
| JP | 2011-184343 A | 9/2011 |
| WO | 99/10354 A1 | 3/1999 |
| WO | 99/26951 A1 | 6/1999 |

OTHER PUBLICATIONS

International Preliminary Report on Patentability and Written Opinion, dated Aug. 25, 2015, issued in corresponding International Application No. PCT/JP2014/052402, 8 pages in English.
Communication dated Mar. 14, 2016 from Korean Intellectual Property Office in counterpart Application No. 10-2015-7019610.
Notification of Reasons for Refusal, dated Jan. 26, 2016, issued in corresponding JP Application No. 2014-026718, 9 pages in English and Japanese.
Written Opinion for PCT/JP2014/052402 dated May 13, 2014.
International Search Report for PCT/JP2014/052402 dated May 13, 2014.
Communication dated Sep. 6, 2016, from the Japanese Patent Office in counterpart application No. 2014-026718.
Communication dated Aug. 25, 2016, from the State Intellectual Property Office of People's Republic of China in counterpart application No. 201480004195.5.

(Continued)

*Primary Examiner* — Porfirio Nazario Gonzalez
(74) *Attorney, Agent, or Firm* — Sughrue Mion, PLLC

(57) ABSTRACT

An object of the present invention is to provide a near-infrared-absorbing composition capable of forming a cured film having excellent heat resistance while maintaining strong near-infrared shielding properties when a cured film is produced. The near-infrared-absorbing composition of the present invention includes a copper complex obtained by reacting two or more kinds of sulfonic acids represented by General Formula (I) described below or salts thereof with a copper component and a solvent.

General Formula (I)

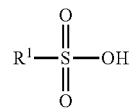

58 Claims, 2 Drawing Sheets

(56) References Cited

OTHER PUBLICATIONS

Office Action dated Nov. 24, 2016, from the Korean Intellectual Property Office in counterpart Korean Application No. 10-2015-7019610.
Office Action dated Jan. 13, 2017 from the Taiwanese Intellectual Property Office in counterpart Taiwanese Application No. 103105384.

NEAR-INFRARED-ABSORBING COMPOSITION, NEAR-INFRARED CUT-OFF FILTER USING SAME, MANUFACTURING METHOD THEREFOR, CAMERA MODULE, AND MANUFACTURING METHOD THEREFOR

CROSS-REFERENCE TO RELATED APPLICATIONS

This application is a Continuation of PCT International Application No. PCT/JP2014/052402 filed on Feb. 3, 2014, which claims priority under 35 U.S.C. §119(a) to Japanese Patent Application No. 2013-030487 filed on Feb. 19, 2013 and Japanese Patent Application No. 2013-153991 filed on Jul. 24, 2013. Each of the above application(s) is hereby expressly incorporated by reference, in its entirety, into the present application.

BACKGROUND OF THE INVENTION

1. Field of the Invention

The present invention relates to a near-infrared-absorbing composition, a near-infrared cut-off filter using the same, a manufacturing method therefor, a camera module, and a manufacturing method therefor.

2. Description of the Related Art

A CCD or CMOS image sensor that is a solid-state imaging element for color images has been used for video cameras, digital still cameras, mobile phones equipped with a camera function, and the like. In the solid-state imaging element, since a silicon photodiode having sensitivity to near-infrared rays is used in the light-receiving section, it is necessary to revise the luminosity factor and a near-infrared cut-off filter (hereinafter, also referred to as the IR cut-off filter) is frequently used.

As a material for the above-described near-infrared cut-off filter, a near-infrared-absorbing composition in which a sulfonic acid ester copper complex is used (JP2001-213918A) and a near-infrared-absorbing composition in which a phosphoric acid ester copper complex is used (WO1999/010354A (JP3933392B)) are known.

SUMMARY OF THE INVENTION

An object of the present invention is to provide a near-infrared-absorbing composition capable of forming a cured film having excellent heat resistance while maintaining strong near-infrared shielding properties when a cured film is produced.

As a result of intensive studies on the basis of the above-described circumstances, the present inventors found that, when a copper complex for which two or more kinds of sulfonic acid or salts thereof or sulfonic acid having no (meth)acrylic ester group is used is blended into a near-infrared-absorbing composition, the above-described problems can be solved.

Specifically, the above-described problem has been solved by means <1> described below and preferably means <2> to <27>.

<1> A near-infrared-absorbing composition, including:

a copper complex obtained by reacting two or more kinds of sulfonic acids represented by General Formula (I) described below or salts thereof with a copper component,

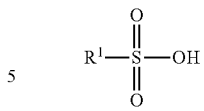

General Formula (I)

(in Formula (I), R¹ represents an organic group.)

<2> A near-infrared-absorbing composition, including:

a copper complex which includes copper as a central metal and includes sulfonic acids represented by General Formula (I) described below having mutually different structures as ligands or a copper complex having structures represented by General Formula (II) described below that are different from each other; and a solvent,

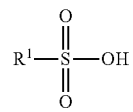

General Formula (I)

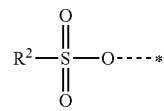

General Formula (II)

(in Formula (I), R¹ represents an organic group, in Formula (II), R² represents an organic group, and "*" indicates a portion at which a coordination bond with copper is formed.)

<3> The near-infrared-absorbing composition according to <1> or <2>, in which each of the R¹ and R² is independently an alkyl group, an aryl group, or an organic group having an unsaturated double bond.

<4> The near-infrared-absorbing composition according to any one of <1> to <3>, in which the R¹ and/or R² are organic groups having a molecular weight of 300 or less.

<5> The near-infrared-absorbing composition according to any one of <1> to <4>, in which the sulfonic acid represented by General Formula (I) is selected from unsubstituted alkyl sulfonic acids, substituted or unsubstituted aryl sulfonic acids, alkyl sulfonic acids substituted with a fluorine atom, and substituted or unsubstituted alkenyl sulfonic acids.

<6> The near-infrared-absorbing composition according to any one of <1> to <5>, in which the copper complex is obtained by reacting three or more kinds of the sulfonic acids represented by General Formula (I) or salts thereof with the copper component or the near-infrared-absorbing composition according to any one of <2> to <5>, including: three or more kinds of copper complexes which include the sulfonic acids represented by General Formula (I) having mutually different structures as ligands or three or more kinds of copper complexes having the structures represented by General Formula (II) that are different from each other.

<7> The near-infrared-absorbing composition according to any one of <2> to <6>, further including: a copper complex which includes the sulfonic acids represented by General Formula (I) all having the same structure as ligands or a copper complex having the structures represented by General Formula (II) that are all identical to each other.

<8> A near-infrared-absorbing composition, including:
a copper complex obtained by reacting sulfonic acids represented by General Formula (III) described below or salts thereof with a copper component; and
a solvent,

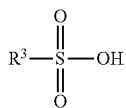

General Formula (III)

(in Formula (III), R³ represents an organic group having no (meth)acrylic ester group).

<9> A near-infrared-absorbing composition, including:
a copper complex which includes copper as a central metal and includes sulfonic acids represented by General Formula (III) described below as ligands or a copper complex which has a structure represented by General Formula (IV) described below; and
a solvent,

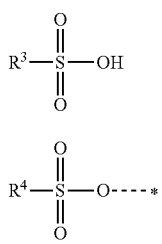

General Formula (III)

General Formula (IV)

(in General Formula (III), R³ represents an organic group having no (meth)acrylic ester group, in General Formula (IV), R⁴ represents an organic group having no (meth)acrylic ester group, and "*" indicates a portion at which a coordination bond with copper is formed).

<10> The near-infrared-absorbing composition according to <8> or <9>, in which each of the R³ and R⁴ is independently an alkyl group or an organic group having an aryl group.

<11> The near-infrared-absorbing composition according to any one of <8> to <10>, in which the R³ and/or R⁴ are organic groups having a molecular weight of 300 or less.

<12> The near-infrared-absorbing composition according to any one of <8> to <11>, in which the sulfonic acid represented by General Formula (III) is selected from unsubstituted alkyl sulfonic acids, substituted or unsubstituted aryl sulfonic acids, alkyl sulfonic acids substituted with a fluorine atom, and substituted or unsubstituted alkenyl sulfonic acids.

<13> The near-infrared-absorbing composition according to any one of <9> to <12>, further including: two or more kinds of copper complexes which include sulfonic acids represented by General Formula (III) all having the same structure as ligands or two or more kinds of copper complexes having the structures represented by General Formula (IV) that are all identical to each other.

<14> The near-infrared-absorbing composition according to any one of <1> to <13>, further including:
a curable compound.

<15> The near-infrared-absorbing composition according to <14>,
in which the curable compound is a tri- or more-functional (meth)acrylate and/or an epoxy resin.

<16> The near-infrared-absorbing composition according to any one of <1> to <15>, in which a solid content of the near-infrared-absorbing composition is in a range of 35 mass % to 90 mass %.

<17> The near-infrared-absorbing composition according to any one of <1> to <16> which is used in a form of a coated film formed on an image sensor for a solid-state imaging element.

<18> A near-infrared-absorbing composition, including:
a copper complex obtained by reacting a compound having two or more acid groups or salts thereof with a copper component.

<19> The near-infrared-absorbing composition according to <18>, in which the acid group included in the compound having two or more acid groups is selected from a sulfonic acid group, a carboxylic acid group, and acid groups including a phosphorous atom.

<20> The near-infrared-absorbing composition according to <18>, in which the compound having two or more acid groups includes at least a sulfonic acid group and a carboxylic acid group.

<21> A near-infrared cut-off filter produced using the near-infrared-absorbing composition according to any one of <1> to <20>.

<22> A camera module, including:
a solid-state imaging element substrate; and
the near-infrared cut-off filter according to <21> disposed on a light-receiving side of the solid-state imaging element substrate.

<23> A method for manufacturing a camera module including a solid-state imaging element substrate and the near-infrared cut-off filter disposed on a light-receiving side of the solid-state imaging element substrate, including:
a step of applying the near-infrared-absorbing composition according to any one of <1> to <20> to the light-receiving side of the solid-state imaging element substrate so as to form a film.

<24> A sulfonic acid copper complex mixture obtained by reacting two or more kinds of sulfonic acids represented by General Formula (I) described below or salts thereof with a copper component,

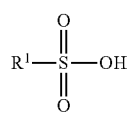

General Formula (I)

(in Formula (I), R¹ represents an organic group).

<25> A sulfonic acid copper complex mixture, including:
a sulfonic acid copper complex which includes copper as a central metal and includes sulfonic acids represented by General Formula (I) described below having mutually different structures as ligands or a sulfonic acid copper complex having structures represented by General Formula (II) described below that are different from each other; and a sulfonic acid copper complex which includes sulfonic acids represented by General Formula (I) described below all having the same structures as ligands or a sulfonic acid copper complex having the structures represented by General Formula (II) described below that are all identical to each other, General Formula (I)

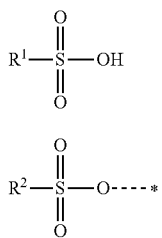

General Formula (II)

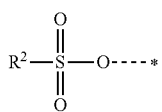

(in General Formula (I), $R^1$ represents an organic group, in Formula (II), $R^2$ represents an organic group, and "*" indicates a portion at which a coordination bond with copper is formed).

<26> A sulfonic acid copper complex obtained by reacting a sulfonic acid represented by General Formula (III) described below or a salt thereof with a copper component, a sulfonic acid copper complex which includes copper as a central metal and includes a sulfonic acid represented by General Formula (III) described below as a ligand, or a sulfonic acid copper complex having a structure represented by General Formula (IV) described below, General Formula (III)

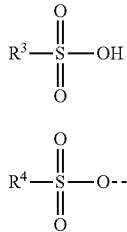

General Formula (IV)

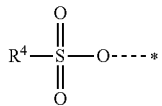

(in Formula (III), $R^3$ represents an organic group having no (meth)acrylic ester group, and, in Formula (IV), $R^4$ represents an organic group having no (meth)acrylic ester group and "*" indicates a portion at which a coordination bond with copper is formed).

<27> The sulfonic acid copper complex according to <26>, in which the copper complex is a sulfonic acid copper complex mixture including two or more kinds of sulfonic acid copper complexes which include sulfonic acids represented by General Formula (III) all having the same structures as ligands or two or more kinds of sulfonic acid copper complexes having structures represented by General Formula (IV) that are all identical to each other.

According to the present invention, it is possible to provide a near-infrared-absorbing composition capable of forming a cured film having excellent heat resistance while maintaining strong near-infrared shielding properties when a cured film is produced.

DESCRIPTION OF THE PREFERRED EMBODIMENTS

Figure 1:
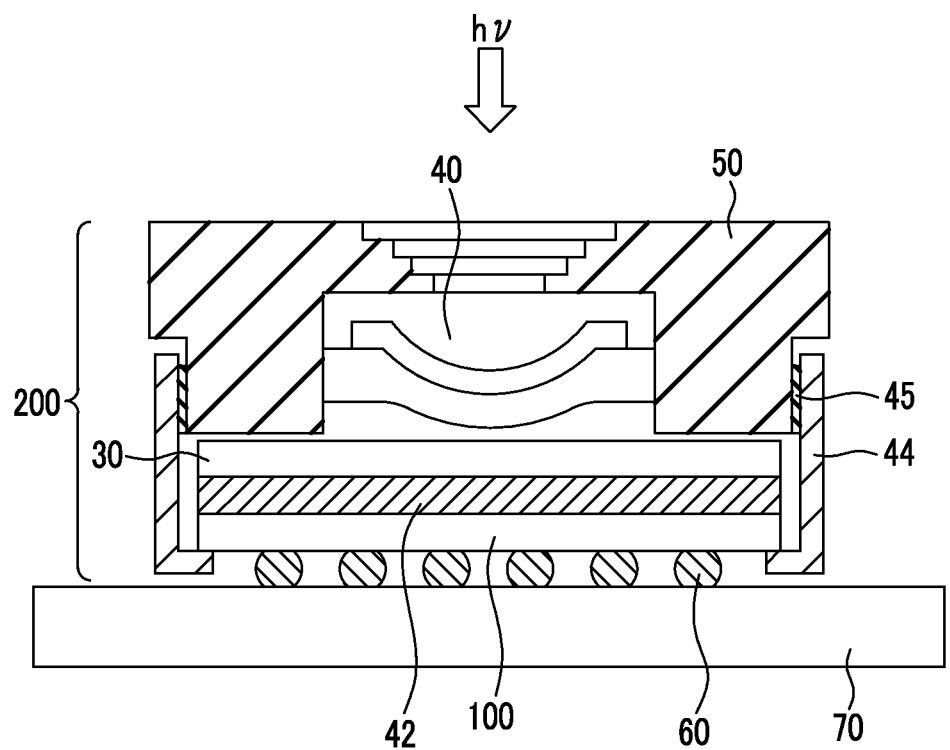
FIG. 1 is a schematic sectional view illustrating a configuration of a camera module including a solid-state imaging element according to an embodiment of the present invention.

Hereinafter, the contents of the present invention will be described in detail. In the present specification, "to" used to express numerical ranges will be used with a meaning that numerical values before and after the "to" are included in the numerical ranges as the lower limit value and the upper limit value.

In the present specification, "(meth)acrylates" represent acrylates and methacrylates, "(meth)acrylic" represents acrylic and methacrylic, and "(meth)acryloyl" represents acryloyl and methacryloyl. In addition, in the present specification, "monomers" and "monomers" refer to the same thing. In the present invention, the monomers are classified into oligomers and polymers and refer to compounds having a weight-average molecular weight of 2,000 or less.

In the present specification, polymerizing compounds refer to compounds having a polymerizable functional group and may be monomers or polymers. Polymerizable functional groups refer to groups that participate in polymerization reactions.

Regarding the denotation of groups (atomic groups) in the present specification, groups with no denotation of 'substituted' and 'unsubstituted' include both groups (atomic groups) having no substituent and groups (atomic groups) having a substituent.

In the present invention, near-infrared rays refer to light rays having a maximum absorption wavelength range of 700 nm to 2500 nm.

<Sulfonic Acid Copper Complex>

Hereinafter, first and second embodiments of a sulfonic acid copper complex of the present invention will be described. The first embodiment is a sulfonic acid copper complex obtained by reacting two or more kinds of sulfonic acids or salts thereof with a copper component. The second embodiment is a sulfonic acid copper complex which includes a sulfonic acid having no (meth)acrylic ester group and copper.

The sulfonic acid copper complex of the present invention is capable of improving heat resistance while maintaining strong near-infrared shielding properties when a cured film is produced using a near-infrared-absorbing composition in which the sulfonic acid copper complex of the present invention is blended. When the sulfonic acid copper complex of the present invention is used in place of a phosphorous acid ester copper complex, it is possible to provide a near-infrared-absorbing composition capable of forming a cured film having excellent heat resistance while maintaining strong near-infrared shielding properties when a cured film is produced.

First Embodiment

The sulfonic acid copper complex of the present invention is obtained by reacting two or more kinds of sulfonic acids represented by General Formula (I) described below or salts thereof with a copper component. When the above-described sulfonic acid copper complex of the present invention is used, it is possible to improve solubility in a solvent (particularly an organic solvent) in the near-infrared-absorbing composition in which the sulfonic acid copper complex of the present invention is blended.

The sulfonic acid copper complex of the present invention is preferably a sulfonic acid copper complex obtained by reacting three or more kinds (more preferably three kinds or four kinds) of sulfonic acids represented by General Formula (I) described below or salts thereof with a copper component. Therefore, it is possible to further improve solubility in a solvent (particularly, an organic solvent) in the near-infrared-absorbing composition in which the sulfonic acid copper complex of the present invention is blended.

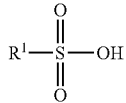

General Formula (I)

(In Formula (I), $R^1$ represents an organic group.)

The sulfonic acid represented by General Formula (I) and a salt thereof act as ligands coordinating copper. Here, the ligand refers to another neutral molecule or the like which is stereoscopically disposed around a copper atom in the copper complex and is bonded to the copper atom.

In the sulfonic acid copper complex of the present invention, the sulfonic acid represented by General Formula (I) is preferably selected from unsubstituted alkyl sulfonic acids, substituted or unsubstituted aryl sulfonic acids, alkyl sulfonic acids substituted with a fluorine atom, and substituted or unsubstituted alkenyl sulfonic acids.

Examples of the unsubstituted alkyl sulfonic acids include the above-described sulfonic acids having an unsubstituted alkyl group as $R^1$ in General Formula (I).

Examples of the substituted or unsubstituted aryl sulfonic acids include the above-described sulfonic acids having a substituted or unsubstituted aryl group as $R^1$ in General Formula (I).

Examples of the alkyl sulfonic acids substituted with fluorine atoms include the above-described sulfonic acids having an alkyl group substituted with fluorine atoms as $R^1$ in General Formula (I).

Examples of the substituted or unsubstituted alkenyl sulfonic acids include the above-described sulfonic acids having an alkyl group including a carbon-carbon double bond as $R^1$ in General Formula (I).

In General Formula (I), $R^1$ represents an organic group, is preferably selected from hydrocarbon groups, specifically, an alkyl group, an aryl group, a heteroaryl group, and organic groups having an unsaturated double bond, and is preferably an alkyl group, an aryl group, or an organic group having an unsaturated double bond.

The alkyl group as $R^1$ may be substituted. In addition, the alkyl group as $R^1$ may have any of a linear shape, a branched shape, and a cyclic shape, but preferably has a linear shape. The alkyl group is preferably an alkyl group having 1 to 30 carbon atoms, more preferably an alkyl group having 1 to 20 carbon atoms, still more preferably an alkyl group having 1 to 10 carbon atoms, and most preferably an alkyl group having 1 to 5 carbon atoms.

The aryl group as $R^1$ is preferably a substituted or unsubstituted aryl group having 6 to 25 carbon atoms, more preferably a substituted or unsubstituted aryl group having 6 to 10 carbon atoms, and still more preferably an aryl group having 6 to 10 carbon atoms and a substituent. In addition, the aryl group as $R^1$ is preferably a six-membered ring. In addition, the aryl group as $R^1$ may be a single ring or a condensed ring, but is preferably a single ring. In a case in which the aryl group as $R^1$ is a condensed ring, the condensed ring preferably has 2 to 8 condensations and more preferably has 2 to 4 condensations. Particularly, the aryl group as $R^1$ is preferably a phenyl group having a substituent.

The heteroaryl group as $R^1$ is preferably a 5-membered ring or a 6-membered ring. In addition, the heteroaryl group is a single ring or a condensed ring, is preferably a single ring or a condensed ring having 2 to 8 condensations, and more preferably a single ring or a condensed ring having 2 to 4 condensations. Specifically, a single ring containing at least one of nitrogen, oxygen, and sulfur atoms or a heteroaryl group derived from a polycyclic aromatic ring is used. Examples of a heteroaryl ring in the heteroaryl group include an oxazol ring, a thiophene ring, a thianthrene ring, a furan ring, a pyran ring, an isobenzofuran ring, a chromene ring, a xanthene ring, a pyrrol ring, a pyrazole ring, an isothiazole ring, an isoxazole ring, a pyrazine ring, a pyrimidine ring, a pyridazine ring, an indolizine ring, an isoindolizine ring, an indole ring, an indazole ring, a purine ring, a quinolizine ring, an isoquinoline ring, a naphthyridine ring, a quinazoline ring, a sinoline ring, a pteridine ring, a carbazole ring, a carboline ring, a phenanthrene ring, an acridine ring, a perimidine ring, a phenanthroline ring, a phthalazine ring, a phenalxazine ring, a phenoxazine ring, a furazan ring, and the like.

Examples of the above-described substituent in the alkyl group, the aryl group and the heteroaryl group include a polymerizable group (preferably a polymerizable group having a carbon-carbon double bond), a halogen atom (a fluorine atom, a chlorine atom, a bromine atom, or an iodine atom), an alkyl group, a carboxylic ester group, a halogenated alkyl group, an alkoxy group, a methacryloyloxy group, an acryloyloxy group, an ether group, a sulfonyl group, a sulfide group, an amide group, an acyl group, a hydroxyl group, a carboxyl group, and the like.

Examples of the polymerizable group include polymerizable groups having a carbon-carbon double bond (preferably vinyl groups and (meth)acryloyloxy groups), (meth)acryloyl groups, epoxy groups, aziridinyl groups, and the like. Among these, vinyl groups, (meth)acryloyloxy groups, and (meth)acryloyl groups are preferred and vinyl groups and (meth)acryloyloxy groups are more preferred.

Meanwhile, the above-described organic groups having an unsaturated double bond may be alkyl groups having the polymerizable group as the substituent or aryl groups having the polymerizable group as the substituent. Examples of the organic groups having an unsaturated double bond include -L-C=C. Here, L is preferably —$(CH_2)_m$— (m is an integer from 1 to 10, preferably an integer from 1 to 6, and more preferably an integer from 1 to 4), a cyclic alkylene group having 5 to 10 carbon atoms, an aryl group having 6 to 10 carbon atoms, or a group obtained by combining the above-described group and at least one of —O—, —COO—, —S—, —NH—, and —CO—. The halogen atom is preferably a fluorine atom.

The halogenated alkyl group is preferably an alkyl group substituted with a fluorine atom. Particularly, the halogenated alkyl group is preferably an alkyl group having two or more fluorine atoms and 1 to 10 carbon atoms and may have any of a linear shape, a branched shape, and a ring shape and preferably has a linear shape or a branched shape. The number of carbon atoms in the alkyl group substituted with fluorine atoms is more preferably in a range of 1 to 10 and still more preferably in a range of 1 to 5, and most preferably in a range of 1 to 3. In the alkyl group substituted with a fluorine atom, the structure at the terminal is preferably (—$CF_3$). The fluorine atom substitution ratio of the alkyl group substituted with fluorine atoms is preferably in a range of 50% to 100% and still more preferably in a range of 80% to 100%. Here, the fluorine atom substitution ratio refers to the ratio (%) of hydrogen atoms substituted with fluorine atoms in the alkyl group substituted with fluorine atoms.

Particularly, the halogenated alkyl group is more preferably a perfluoroalkyl group, still more preferably a perfluoroalkyl group having 1 to 10 carbon atoms, and most preferably a trifluoroethyl group or a trifluoromethyl group.

Examples of the carboxylic acid ester group include methyl carboxylic acid groups, ethyl carboxylic acid groups, propyl carboxylic acid groups, butyl carboxylic acid groups, and the like and methyl carboxylic acid groups are preferred.

In addition, the above-described alkyl group, aryl group, and heteroaryl group may have the above-described substituent and/or a divalent linking group. The divalent linking group is preferably $-(CH_2)_m-$ (m is an integer from 1 to 10, preferably an integer from 1 to 6, and more preferably an integer from 1 to 4), a cyclic alkylene group having 5 to 10 carbon atoms, or a group obtained by combining the above-described group and at least one of $-O-$, $-COO-$, $-S-$, $-NH-$, and $-CO-$.

In the sulfonic acid copper complex in the present invention, in a case in which the alkyl group has a substituent as $R^1$, the substituent is preferably the above-described halogen atom (preferably a fluorine atom), a vinyl group, a (meth) acryloyloxy group, or (meth)acryloyl group and more preferably a vinyl group or a (meth)acryloyloxy group.

In addition, in a case in which the aryl group has a substituent as $R^1$, the substituent is preferably a halogen atom (preferably a fluorine atom), a vinyl group, an unsubstituted alkyl group (preferably a methyl group), a carboxylic acid ester group (preferably methyl carboxylic acid ester group), or a (meth)acryloyl group and more preferably a vinyl group, a (meth)acryloyl group, or a methyl group.

In General Formula (I), $R^1$ is preferably an organic group having a molecular weight of 300 or less, more preferably an organic group having a molecular weight in a range of 50 to 200, and still more preferably an organic group having a molecular weight in a range of 60 to 100.

Hereinafter, preferred aspects (1A) to (1D) of the sulfonic acid copper complex of the present invention will be exemplified, but the present invention is not limited thereto.

(1A) A copper complex including copper as the central metal and the sulfonic acids represented by General Formula (I) as ligands in which the ligands are different from each other (in other words, a copper complex including copper as the central metal and the sulfonic acids represented by General Formula (I) described below having mutually different structures, hereinafter, also referred to as copper complex (I-A)) or a copper complex having structures represented by General Formula (II) described below in which the structures are different from each other (hereinafter, also referred to as copper complex (II-A)). Here, when copper is represented by Cu and the mutually different ligands (sulfonic acids) are represented by A and B, the copper complex (I-A) and the copper complex (II-A) have a structure like A-Cu—B, that is, an asymmetrical structure with respect to copper.

(In General Formula (II), $R^2$ represents an organic group. "*" indicates a portion at which a coordination bond with copper is formed.)

In General Formula (II), $R^2$ has the same meaning and preferred range as $R^1$ in Formula (I).

(1B) In the aspect (1A), furthermore, the sulfonic acid copper complex includes the sulfonic acids represented by General Formula (I) as ligands and the ligands are all identical to each other (hereinafter, also referred to as copper complex (I-B)) or a sulfonic acid copper complex mixture including a sulfonic acid copper complex having structures represented by General Formula (II) in which the structures are all identical to each other (hereinafter, also referred to as copper complex (II-B)).

That is, a sulfonic acid copper complex mixture including the copper complex (I-A) or the copper complex (II-A) and the copper complex (I-B) or the copper complex (II-B). Here, when copper is represented by Cu and ligands (sulfonic acids) are represented by A and B, the copper complex (I-B) and the copper complex (II-B) have a structure like A-Cu-A or B—Cu—B, that is, an asymmetrical structure with respect to copper.

(1C) A sulfonic acid copper complex mixture including three or more kinds (preferably three or four kinds) of the copper complex (I-A) or the copper complex (II-A).

(1D) In the aspect (1C), furthermore, the sulfonic acid copper complex mixture including the copper complex (I-A) or the copper complex (II-A) and the copper complex (I-B) or the copper complex (II-B). That is, a sulfonic acid copper complex mixture including three or more kinds (preferably three or four kinds) of the copper complex (I-A) or the copper complex (II-A) and the copper complex (I-B) or the copper complex (II-B).

Second Embodiment

The sulfonic acid copper complex of the present invention may be a sulfonic acid copper complex obtained by reacting a sulfonic acid represented by General Formula (III) described below or a salt thereof with a copper component, a sulfonic acid copper complex including copper as the central metal and the sulfonic acid represented by General Formula (III) described below, or a sulfonic acid copper complex having a structure represented by General Formula (IV) described below.

When the above-described sulfonic acid copper complex of the present invention is used, it is possible to further improve the solubility of the near-infrared-absorbing composition in which the sulfonic acid copper complex of the present invention is blended in a solvent (particularly, water).

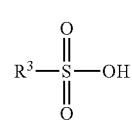

General Formula (III)

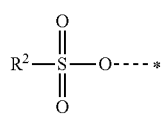

General Formula (II)

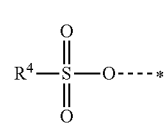

General Formula (IV)

(In General Formula (III), $R^3$ represents an organic group having no (meth)acrylic ester group.

In General Formula (IV), $R^4$ represents an organic group having no (meth)acrylic ester group. "*" indicates a portion at which a coordination bond with copper is formed.)

Here, in General Formulae (III) and (IV), $R^3$ and $R^4$ have the same meaning as $R^1$ and $R^2$ in General Formulae (I) and (II) except for the fact that an organic group having a (meth)acrylic ester group is excluded.

In General Formulae (III) and (IV), $R^3$ and $R^4$ are preferably alkyl groups (particularly, unsubstituted alkyl groups having 1 to 10 carbon atoms), aryl groups having a substituent (particularly, aryl groups having an alkyl group having 1 to 5 carbon atoms as the substituent), organic groups having an unsubstituted double bond (particularly, alkyl groups having 1 to 10 carbon atoms which have a vinyl group as the substituent, aryl groups having 6 to 10 carbon atoms which have a vinyl group as the substituent, and alkyl groups having 1 to 10 carbon atoms which have a divalent linking group (particularly, a group obtained by combining —$(CH_2)_m$— (m is an integer from 1 to 10), cyclic alkylene groups having 5 to 10 carbon atoms, and —CO—)) all of which are described regarding $R^1$ and $R^2$ in General Formulae (I) and (II).

In addition, the number of kinds of the sulfonic acid that is reacted with the copper component or salts thereof is generally one or more, preferably two or more, more preferably three or more, and particularly preferably three or four.

Hereinafter, preferred aspects of the sulfonic acid copper complex of the present invention will be exemplified, but the present invention is not limited thereto.

(2A) A sulfonic acid copper complex including the sulfonic acids represented by General Formula (III) as ligands with respect to the copper component in which the ligands are all identical to each other (hereinafter, also referred to as copper complex (III-A)) or a copper complex including copper as the central metal and having the structures represented by General Formula (IV) in which the structures are all identical to each other (hereinafter, also referred to as copper complex (IV-A)). That is, a sulfonic acid copper complex including one kind of the copper complex (III-A) or the copper complex (IV-A).

(2B) A sulfonic acid copper complex mixture including two or more kinds (preferably three or four kinds) of the copper complexes (III-A) or the copper complexes (IV-A) with respect to the copper component.

First Embodiment and Second Embodiment

Hereinafter, common matters regarding sulfonic acid copper complexes of first and second embodiments will be described.

The molecular weights of the sulfonic acids represented by General Formulae (I) and (III) and the formula weight of the structures represented by General Formulae (II) and (IV) are preferably in a range of 60 to 500, more preferably in a range of 70 to 300, and most preferably in a range of 80 to 200.

Specific examples of the sulfonic acid used in the sulfonic acid copper complex of the present invention include exemplary compounds described the following tables, but are not limited thereto. In addition, it is also possible to use salts of the exemplary compounds described in the following tables.

In the following tables, the organic groups of A-1 to A-130 represent Rs in General Formulae described below. In addition, in the following tables, "*s" in the organic groups of A-1 to A-130 indicate bonding portions with sulfur atoms in the general formulae described below.

TABLE 1

$$R-\underset{\underset{O}{\|}}{\overset{\overset{O}{\|}}{S}}-OH$$

| | R |
|---|---|
| A-1 | —$CH_3$ |
| A-2 | —$CH_2CH_3$ |
| A-3 | —$CH_2CH_2CH_3$ |
| A-4 | —$CH(CH_3)_2$ |
| A-5 | *~~~ |
| A-6 | *~Y |
| A-7 | *~Y |
| A-8 | *~⊥ |
| A-9 | *~~~ |
| A-10 | *~Y |

TABLE 1-continued $$R-\underset{\underset{O}{\overset{O}{\|}}}{\overset{\|}{S}}-OH$$

| | R |
|---|---|
| A-11 | (structure: branched alkyl chain) |
| A-12 | (structure: branched alkyl chain) |
| A-13 | (structure: branched alkyl chain) |
| A-14 | (structure: branched alkyl chain) |
| A-15 | (structure: branched alkyl chain) |
| A-16 | (structure: branched alkyl chain) |
| A-17 | (structure: branched alkyl chain) |
| A-18 | (structure: branched alkyl chain) |
| A-19 | (structure: alkyl chain with double bond) |
| A-20 | (structure: long alkyl chain with terminal isopropyl) |
| A-21 | —CH$_2$CH$_2$OH |
| A-22 | —CH$_2$CH$_2$OCH$_3$ |
| A-23 | —(CH$_2$CH$_2$O)$_4$CH$_3$ |
| A-24 | —(CH$_2$CH$_2$O)$_9$CH$_3$ |
| A-25 | —(CH$_2$CH$_2$O)$_{23}$CH$_3$ |
| A-26 | (structure: —(CH$_2$CH$_2$O)$_4$-2-ethylhexyl) |
| A-27 | —(CH$_2$CH$_2$O)$_4$C$_6$H$_5$ |
| A-28 | —CH$_2$CH$_2$Cl |
| A-29 | —CH$_2$CH$_2$Br |
| A-30 | —CH$_2$CH$_2$NHCH$_3$ |
| A-31 | —CH$_2$CH(CH$_3$)OCH$_3$ |
| A-32 | —(CH$_2$CH(CH$_3$)O)$_4$CH$_3$ |
| A-33 | —(CH$_2$CH(CH$_3$)O)$_9$CH$_3$ |
| A-34 | —(CH$_2$CH(CH$_3$)O)$_{23}$CH$_3$ |
| A-35 | (structure: —(CH$_2$CH(CH$_3$)O)$_4$-2-ethylhexyl) |
| A-36 | —(CH$_2$CH(CH$_3$)O)$_4$C$_6$H$_5$ |
| A-37 | —(CH$_2$CH(CH$_3$)O)$_2$(CH$_2$CH$_2$O)$_2$CH$_3$ |
| A-38 | —(CH$_2$CH$_2$CH$_2$CH$_2$O)$_2$CH$_3$ |
| A-39 | —CH$_2$CH$_2$OC(=O)CH$_3$ |
| A-40 | —(CH$_2$CH$_2$O)$_4$C(=O)CH$_3$ |
| A-41 | —(CH$_2$CH$_2$O)$_9$C(=O)CH$_3$ |
| A-42 | —CH(CH$_3$)CH$_2$OC(=O)CH$_3$ |
| A-43 | —CH$_2$CH(CH$_3$)OC(=O)CH$_3$ |
| A-44 | —(CH(CH$_3$)CH$_2$O)$_4$C(=O)CH$_3$ |
| A-45 | —(CH$_2$CH(CH$_3$)O)$_4$C(=O)CH$_3$ |
| A-46 | —CH$_2$CH(CH$_3$)OC(=O)CH$_2$CH$_3$ |

TABLE 1-continued $$R-\underset{\underset{O}{\overset{O}{\|}}}{\overset{\|}{S}}-OH$$

| | R |
|---|---|
| A-47 | —CH$_2$CH(CH$_3$)OC(=O)CH$_2$CH$_3$ |
| A-48 | —CH(CH$_2$CH$_3$)CH$_2$OC(=O)CH$_3$ |
| A-49 | —CH$_2$CH(CH$_2$CH$_3$)OC(=O)CH$_3$ |
| A-50 | —CH(CH$_2$CH$_3$)CH$_2$OC(=O)CH$_3$ |
| A-51 | —CH(CH$_2$CH$_3$)CH$_2$OC(=O)CH$_2$CH$_3$ |
| A-52 | —CH$_2$CH(CH$_2$CH$_3$)OC(=O)CH$_2$CH$_3$ |
| A-53 | —CH(CH$_2$CH$_3$)CH$_2$OC(=O)CH$_2$CH$_3$ |
| A-54 | —CH(CH$_3$)CH$_2$OC(=O)CH(CH$_3$)$_2$ |
| A-55 | —CH$_2$CH(CH$_3$)OC(=O)CH(CH$_3$)$_2$ |
| A-56 | —CH$_2$CH(CH$_3$)OC(=O)CH(CH$_3$)$_2$ |
| A-57 | —CH(CH$_2$CH$_3$)CH$_2$OC(=O)CH(CH$_3$)$_2$ |

TABLE 2

A-58, A-59, A-60, A-61, A-62, A-63, A-64, A-65, A-66, A-67, A-68, A-69, A-70, A-71, A-72, A-73, A-74, A-75

TABLE 3
A-76 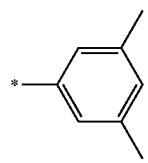
A-77 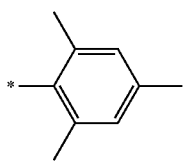
A-78 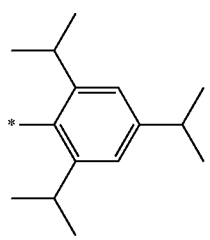
A-79 
A-80 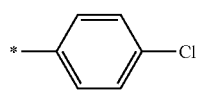
A-81 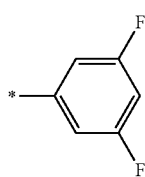
A-82 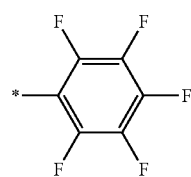 [SMILES: *c1c(F)c(F)c(F)c(F)c1F]
A-83 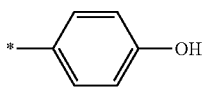
A-84 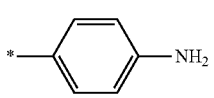 [SMILES: *c1ccc(N)cc1]
A-85 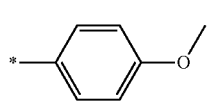
A-86 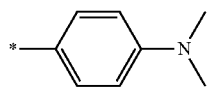 [SMILES: *c1ccc(N(C)C)cc1]
A-87 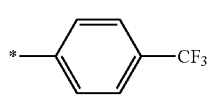 [SMILES: *c1ccc(C(F)(F)F)cc1]
TABLE 3-continued
A-88 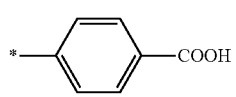 [SMILES: *c1ccc(C(=O)O)cc1]
A-89 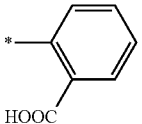
TABLE 4
A-90 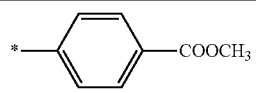
A-91 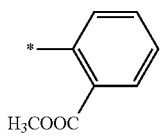
A-92 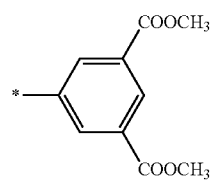 [SMILES: *c1cc(C(=O)OC)cc(C(=O)OC)c1]
A-93 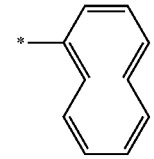 [SMILES: *c1ccccccccc1]
A-94 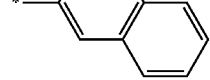
A-95 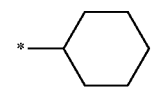
| | |
|---|---|
| A-96 | —$CF_3$ |
| A-97 | —$CF_2CF_3$ |
| A-98 | —$(CF_2)_2CF_3$ |
| A-99 | —$(CF_2)_3CF_3$ |
| A-100 | —$(CF_2)_4CF_3$ |
| A-101 | —$(CF_2)_5CF_3$ |
| A-102 | —$(CF_2)_6CF_3$ |
| A-103 | —$(CF_2)_7CF_3$ |
| A-104 | —$(CF_2)_9CF_3$ |
A-105 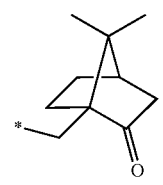

TABLE 4-continued

| | |
|---|---|
| A-106 | [structure: camphor-like bicyclic ketone with *] |
| A-107 | [structure: vinyl, *-CH=CH2] |
| A-108 | [structure: allyl, *-CH2-CH=CH2] |
| A-109 | [structure: 2-methylallyl, *-CH2-C(CH3)=CH2] |
| A-110 | [structure: *-CH2CH2CH2-O-C(=O)-CH=CH2] |
| A-111 | [structure: *-CH2CH2CH2-O-C(=O)-C(CH3)=CH2] |
| A-112 | [structure: *-CH2-C(CH3)2-NH-C(=O)-CH=CH2] |
| A-113 | [structure: *-C6H4-CH=CH2 (para)] |
| A-114 | [structure: *-C6H4-C(CH3)=CH2 (para)] |
| A-115 | [structure: 3-pyridyl-*] |

TABLE 5

| | |
|---|---|
| A-116 | [structure: 2-thienyl-CH2-*] |
| A-117 | [structure: 2-furyl-CH2-*] |
| A-118 | [structure: 5-indolyl-*] |
| A-119 | [structure: 3,5-dimethoxyphenyl-*] |
| A-120 | [structure: 2-fluorophenyl-*] |
| A-121 | [structure: 3,5-bis(trifluoromethyl)phenyl-*] |
| A-122 | [structure: 2-trifluoromethyl-4-fluorophenyl-*] (CF3 ortho, F para to *) |
| A-123 | [structure: 2,3,5,6-tetrafluoro-4-(trifluoromethyl)phenyl-*] |
| A-124 | [structure: 4-(CF2CF3)-phenyl-*] |
| A-125 | [structure: 2-(CF2CF3)-phenyl-*] |
| A-126 | [structure: 3-(CF2CF3)-phenyl-*] |
| A-127 | [structure: 4-(CF2CF2CF3)-phenyl-*] |
| A-128 | [structure: 2-(CF2CF2CF3)-phenyl-*] |
| A-129 | [structure: 3-(CF2CF2CF3)-phenyl-*] |

TABLE 5-continued

A-130 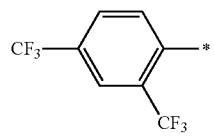

TABLE 6

A-131 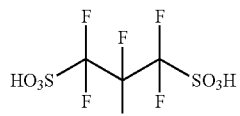

A-132 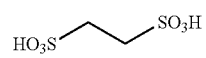

A-133 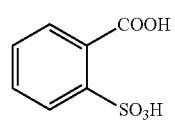 [SMILES: O=C(O)c1ccccc1S(=O)(=O)O]

A-134 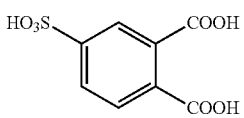

Specific examples of the sulfonic acid copper complex of the present invention include sulfonic acid copper complexes in which one or more compounds selected from the exemplary compounds (A-1) to A-(130) of the sulfonic acid are used and examples thereof include exemplary compounds (Cu-1) to (Cu-789) described below. The present invention is not limited to the exemplary compounds described below.

Meanwhile, in the above-described sulfonic acid copper complex of the second embodiment (that is, a copper complex in which only any one of the exemplary compounds of the sulfonic acid is used), sulfonic acid copper complexes obtained by reacting only the exemplary compound (A-110) or (A-111) are excluded.

In the following tables, compounds (i) to (iv) correspond to $R^1$ to $R^4$ in the sulfonic acids represented by General Formulae (I) and (II) or the structures represented by General Formulae (II) and (IV). For example, the copper complex (Cu-1) represents a copper complex in which the exemplary compounds (A-1) and (A-2) are used as the sulfonic acid, that is, a copper complex obtained by reacting two kinds of sulfonic acids.

In addition, (A-1) and the like in the following tables correspond to the exemplary compounds (A-1) to (A-130) of the sulfonic acid.

TABLE 7

| Copper complex | Sulfonic acid | | | |
|---|---|---|---|---|
| | Compound i | Compound ii | Compound iii | Compound iv |
| Cu-1 | A-1 | A-2 | — | — |
| Cu-2 | A-2 | A-13 | — | — |
| Cu-3 | A-2 | A-62 | — | — |
| Cu-4 | A-2 | A-74 | — | — |
| Cu-5 | A-2 | A-77 | — | — |
| Cu-6 | A-2 | A-82 | — | — |
| Cu-7 | A-2 | A-91 | — | — |

TABLE 7-continued

| Copper complex | Sulfonic acid | | | |
|---|---|---|---|---|
| | Compound i | Compound ii | Compound iii | Compound iv |
| Cu-8 | A-2 | A-96 | — | — |
| Cu-9 | A-2 | A-105 | — | — |
| Cu-10 | A-2 | A-107 | — | — |
| Cu-11 | A-2 | A-111 | — | — |
| Cu-12 | A-2 | A-112 | — | — |
| Cu-13 | A-2 | A-113 | — | — |
| Cu-14 | A-2 | A-13 | A-62 | — |
| Cu-15 | A-2 | A-52 | A-105 | — |
| Cu-16 | A-2 | A-52 | A-107 | — |
| Cu-17 | A-2 | A-52 | A-107 | — |
| Cu-18 | A-2 | A-52 | A-112 | — |
| Cu-19 | A-2 | A-13 | A-62 | A-105 |
| Cu-20 | A-2 | A-13 | A-62 | A-107 |
| Cu-21 | A-2 | A-13 | A-62 | A-107 |
| Cu-22 | A-2 | A-13 | A-62 | A-112 |
| Cu-23 | A-1 | — | — | — |
| Cu-24 | A-13 | — | — | — |
| Cu-25 | A-77 | — | — | — |
| Cu-26 | A-105 | — | — | — |
| Cu-27 | A-107 | — | — | — |
| Cu-28 | A-112 | — | — | — |
| Cu-29 | A-113 | — | — | — |
| Cu-30 | A-2 | — | — | — |
| Cu-31 | A-3 | — | — | — |
| Cu-32 | A-4 | — | — | — |
| Cu-33 | A-5 | — | — | — |
| Cu-34 | A-6 | — | — | — |
| Cu-34 | A-7 | — | — | — |
| Cu-36 | A-8 | — | — | — |
| Cu-37 | A-9 | — | — | — |
| Cu-38 | A-10 | — | — | — |
| Cu-39 | A-11 | — | — | — |
| Cu-40 | A-12 | — | — | — |
| Cu-41 | A-14 | — | — | — |
| Cu-42 | A-15 | — | — | — |
| Cu-43 | A-16 | — | — | — |
| Cu-44 | A-17 | — | — | — |
| Cu-45 | A-18 | — | — | — |
| Cu-46 | A-19 | — | — | — |
| Cu-47 | A-20 | — | — | — |
| Cu-48 | A-21 | — | — | — |
| Cu-49 | A-22 | — | — | — |
| Cu-50 | A-23 | — | — | — |
| Cu-51 | A-24 | — | — | — |
| Cu-52 | A-25 | — | — | — |
| Cu-53 | A-26 | — | — | — |
| Cu-54 | A-27 | — | — | — |
| Cu-55 | A-28 | — | — | — |
| Cu-56 | A-29 | — | — | — |
| Cu-57 | A-30 | — | — | — |
| Cu-58 | A-31 | — | — | — |
| Cu-59 | A-32 | — | — | — |
| Cu-60 | A-33 | — | — | — |

TABLE 8

| Copper complex | Sulfonic acid | | | |
|---|---|---|---|---|
| | Compound i | Compound ii | Compound iii | Compound iv |
| Cu-61 | A-34 | — | — | — |
| Cu-62 | A-35 | — | — | — |
| Cu-63 | A-36 | — | — | — |
| Cu-64 | A-37 | — | — | — |
| Cu-65 | A-38 | — | — | — |
| Cu-66 | A-39 | — | — | — |
| Cu-67 | A-40 | — | — | — |
| Cu-68 | A-41 | — | — | — |
| Cu-69 | A-42 | — | — | — |
| Cu-70 | A-43 | — | — | — |
| Cu-71 | A-44 | — | — | — |
| Cu-72 | A-45 | — | — | — |
| Cu-73 | A-46 | — | — | — |

TABLE 8-continued

| Copper complex | Sulfonic acid Compound i | Compound ii | Compound iii | Compound iv |
|---|---|---|---|---|
| Cu-74 | A-47 | — | — | — |
| Cu-75 | A-48 | — | — | — |
| Cu-76 | A-49 | — | — | — |
| Cu-77 | A-50 | — | — | — |
| Cu-78 | A-51 | — | — | — |
| Cu-79 | A-52 | — | — | — |
| Cu-80 | A-53 | — | — | — |
| Cu-81 | A-54 | — | — | — |
| Cu-82 | A-55 | — | — | — |
| Cu-83 | A-56 | — | — | — |
| Cu-84 | A-57 | — | — | — |
| Cu-85 | A-58 | — | — | — |
| Cu-86 | A-59 | — | — | — |
| Cu-87 | A-60 | — | — | — |
| Cu-88 | A-61 | — | — | — |
| Cu-89 | A-62 | — | — | — |
| Cu-90 | A-63 | — | — | — |
| Cu-91 | A-64 | — | — | — |
| Cu-92 | A-65 | — | — | — |
| Cu-93 | A-66 | — | — | — |
| Cu-94 | A-67 | — | — | — |
| Cu-95 | A-68 | — | — | — |
| Cu-96 | A-69 | — | — | — |
| Cu-97 | A-70 | — | — | — |
| Cu-98 | A-71 | — | — | — |
| Cu-99 | A-72 | — | — | — |
| Cu-100 | A-73 | — | — | — |
| Cu-101 | A-74 | — | — | — |
| Cu-102 | A-75 | — | — | — |
| Cu-103 | A-76 | — | — | — |
| Cu-104 | A-78 | — | — | — |
| Cu-105 | A-79 | — | — | — |
| Cu-106 | A-80 | — | — | — |
| Cu-107 | A-81 | — | — | — |
| Cu-108 | A-82 | — | — | — |
| Cu-109 | A-83 | — | — | — |
| Cu-110 | A-84 | — | — | — |
| Cu-111 | A-85 | — | — | — |
| Cu-112 | A-86 | — | — | — |
| Cu-113 | A-87 | — | — | — |
| Cu-114 | A-88 | — | — | — |
| Cu-115 | A-89 | — | — | — |
| Cu-116 | A-90 | — | — | — |
| Cu-117 | A-91 | — | — | — |
| Cu-118 | A-92 | — | — | — |
| Cu-119 | A-93 | — | — | — |
| Cu-120 | A-94 | — | — | — |

TABLE 9

| Copper complex | Sulfonic acid Compound i | Compound ii | Compound iii | Compound iv |
|---|---|---|---|---|
| Cu-121 | A-95 | — | — | — |
| Cu-122 | A-96 | — | — | — |
| Cu-123 | A-97 | — | — | — |
| Cu-124 | A-98 | — | — | — |
| Cu-125 | A-99 | — | — | — |
| Cu-126 | A-100 | — | — | — |
| Cu-127 | A-101 | — | — | — |
| Cu-128 | A-102 | — | — | — |
| Cu-129 | A-103 | — | — | — |
| Cu-130 | A-104 | — | — | — |
| Cu-131 | A-106 | — | — | — |
| Cu-132 | A-108 | — | — | — |
| Cu-133 | A-109 | — | — | — |
| Cu-134 | A-110 | — | — | — |
| Cu-135 | A-111 | — | — | — |
| Cu-136 | A-112 | — | — | — |
| Cu-137 | A-114 | — | — | — |
| Cu-138 | A-115 | — | — | — |
| Cu-139 | A-116 | — | — | — |

TABLE 9-continued

| Copper complex | Sulfonic acid Compound i | Compound ii | Compound iii | Compound iv |
|---|---|---|---|---|
| Cu-140 | A-117 | — | — | — |
| Cu-141 | A-118 | — | — | — |
| Cu-142 | A-119 | — | — | — |
| Cu-143 | A-120 | — | — | — |
| Cu-144 | A-121 | — | — | — |
| Cu-145 | A-122 | — | — | — |
| Cu-146 | A-123 | — | — | — |
| Cu-147 | A-124 | — | — | — |
| Cu-148 | A-125 | — | — | — |
| Cu-149 | A-126 | — | — | — |
| Cu-150 | A-127 | — | — | — |
| Cu-151 | A-128 | — | — | — |
| Cu-152 | A-129 | — | — | — |
| Cu-153 | A-130 | — | — | — |
| Cu-154 | A-1 | A-3 | — | — |
| Cu-155 | A-1 | A-4 | — | — |
| Cu-156 | A-1 | A-5 | — | — |
| Cu-157 | A-1 | A-6 | — | — |
| Cu-158 | A-1 | A-7 | — | — |
| Cu-159 | A-1 | A-8 | — | — |
| Cu-160 | A-1 | A-9 | — | — |
| Cu-161 | A-1 | A-10 | — | — |
| Cu-162 | A-1 | A-11 | — | — |
| Cu-163 | A-1 | A-12 | — | — |
| Cu-164 | A-1 | A-13 | — | — |
| Cu-165 | A-1 | A-14 | — | — |
| Cu-166 | A-1 | A-15 | — | — |
| Cu-167 | A-1 | A-16 | — | — |
| Cu-168 | A-1 | A-17 | — | — |
| Cu-169 | A-1 | A-18 | — | — |
| Cu-170 | A-1 | A-19 | — | — |
| Cu-171 | A-1 | A-20 | — | — |
| Cu-172 | A-1 | A-21 | — | — |
| Cu-173 | A-1 | A-22 | — | — |
| Cu-174 | A-1 | A-23 | — | — |
| Cu-175 | A-1 | A-24 | — | — |
| Cu-176 | A-1 | A-25 | — | — |
| Cu-177 | A-1 | A-26 | — | — |
| Cu-178 | A-1 | A-27 | — | — |
| Cu-179 | A-1 | A-28 | — | — |
| Cu-180 | A-1 | A-29 | — | — |

TABLE 10

| Copper complex | Sulfonic acid Compound i | Compound ii | Compound iii | Compound iv |
|---|---|---|---|---|
| Cu-181 | A-1 | A-30 | — | — |
| Cu-182 | A-1 | A-31 | — | — |
| Cu-183 | A-1 | A-32 | — | — |
| Cu-184 | A-1 | A-33 | — | — |
| Cu-185 | A-1 | A-34 | — | — |
| Cu-186 | A-1 | A-35 | — | — |
| Cu-187 | A-1 | A-36 | — | — |
| Cu-188 | A-1 | A-37 | — | — |
| Cu-189 | A-1 | A-38 | — | — |
| Cu-190 | A-1 | A-39 | — | — |
| Cu-191 | A-1 | A-40 | — | — |
| Cu-192 | A-1 | A-41 | — | — |
| Cu-193 | A-1 | A-42 | — | — |
| Cu-194 | A-1 | A-43 | — | — |
| Cu-195 | A-1 | A-44 | — | — |
| Cu-196 | A-1 | A-45 | — | — |
| Cu-197 | A-1 | A-46 | — | — |
| Cu-198 | A-1 | A-47 | — | — |
| Cu-199 | A-1 | A-48 | — | — |
| Cu-200 | A-1 | A-49 | — | — |
| Cu-201 | A-1 | A-50 | — | — |
| Cu-202 | A-1 | A-51 | — | — |
| Cu-203 | A-1 | A-52 | — | — |
| Cu-204 | A-1 | A-53 | — | — |
| Cu-205 | A-1 | A-54 | — | — |

TABLE 10-continued

| Copper complex | Compound i | Compound ii | Compound iii | Compound iv |
|---|---|---|---|---|
| Cu-206 | A-1 | A-55 | — | — |
| Cu-207 | A-1 | A-56 | — | — |
| Cu-208 | A-1 | A-57 | — | — |
| Cu-209 | A-1 | A-58 | — | — |
| Cu-210 | A-1 | A-59 | — | — |
| Cu-211 | A-1 | A-60 | — | — |
| Cu-212 | A-1 | A-61 | — | — |
| Cu-213 | A-1 | A-62 | — | — |
| Cu-214 | A-1 | A-63 | — | — |
| Cu-215 | A-1 | A-64 | — | — |
| Cu-216 | A-1 | A-65 | — | — |
| Cu-217 | A-1 | A-66 | — | — |
| Cu-218 | A-1 | A-67 | — | — |
| Cu-219 | A-1 | A-68 | — | — |
| Cu-220 | A-1 | A-69 | — | — |
| Cu-221 | A-1 | A-70 | — | — |
| Cu-222 | A-1 | A-71 | — | — |
| Cu-223 | A-1 | A-72 | — | — |
| Cu-224 | A-1 | A-73 | — | — |
| Cu-225 | A-1 | A-74 | — | — |
| Cu-226 | A-1 | A-75 | — | — |
| Cu-227 | A-1 | A-76 | — | — |
| Cu-228 | A-1 | A-77 | — | — |
| Cu-229 | A-1 | A-78 | — | — |
| Cu-230 | A-1 | A-79 | — | — |
| Cu-231 | A-1 | A-80 | — | — |
| Cu-232 | A-1 | A-81 | — | — |
| Cu-233 | A-1 | A-82 | — | — |
| Cu-234 | A-1 | A-83 | — | — |
| Cu-235 | A-1 | A-84 | — | — |
| Cu-236 | A-1 | A-85 | — | — |
| Cu-237 | A-1 | A-86 | — | — |
| Cu-238 | A-1 | A-87 | — | — |
| Cu-239 | A-1 | A-88 | — | — |
| Cu-240 | A-1 | A-89 | — | — |

TABLE 11

| Copper complex | Compound i | Compound ii | Compound iii | Compound iv |
|---|---|---|---|---|
| Cu- | A-1 | A-90 | — | — |
| Cu- | A-1 | A-91 | — | — |
| Cu- | A-1 | A-92 | — | — |
| Cu- | A-1 | A-93 | — | — |
| Cu- | A-1 | A-94 | — | — |
| Cu- | A-1 | A-95 | — | — |
| Cu- | A-1 | A-96 | — | — |
| Cu- | A-1 | A-97 | — | — |
| Cu- | A-1 | A-98 | — | — |
| Cu- | A-1 | A-99 | — | — |
| Cu- | A-1 | A-100 | — | — |
| Cu- | A-1 | A-101 | — | — |
| Cu- | A-1 | A-102 | — | — |
| Cu- | A-1 | A-103 | — | — |
| Cu- | A-1 | A-104 | — | — |
| Cu- | A-1 | A-105 | — | — |
| Cu- | A-1 | A-106 | — | — |
| Cu- | A-1 | A-107 | — | — |
| Cu- | A-1 | A-108 | — | — |
| Cu- | A-1 | A-109 | — | — |
| Cu- | A-1 | A-110 | — | — |
| Cu- | A-1 | A-111 | — | — |
| Cu- | A-1 | A-112 | — | — |
| Cu- | A-1 | A-113 | — | — |
| Cu- | A-1 | A-114 | — | — |
| Cu- | A-1 | A-115 | — | — |
| Cu- | A-1 | A-116 | — | — |
| Cu- | A-1 | A-117 | — | — |
| Cu- | A-1 | A-118 | — | — |
| Cu- | A-1 | A-119 | — | — |
| Cu-271 | A-1 | A-120 | — | — |
| Cu-272 | A-1 | A-121 | — | — |
| Cu-273 | A-1 | A-122 | — | — |
| Cu-274 | A-1 | A-123 | — | — |
| Cu-275 | A-1 | A-124 | — | — |
| Cu-276 | A-1 | A-125 | — | — |
| Cu-277 | A-1 | A-126 | — | — |
| Cu-278 | A-1 | A-127 | — | — |
| Cu-279 | A-1 | A-128 | — | — |
| Cu-280 | A-1 | A-129 | — | — |
| Cu-281 | A-1 | A-130 | — | — |
| Cu-282 | A-2 | A-3 | — | — |
| Cu-283 | A-2 | A-4 | — | — |
| Cu-284 | A-2 | A-5 | — | — |
| Cu-285 | A-2 | A-6 | — | — |
| Cu-286 | A-2 | A-7 | — | — |
| Cu-287 | A-2 | A-8 | — | — |
| Cu-288 | A-2 | A-9 | — | — |
| Cu-289 | A-2 | A-10 | — | — |
| Cu-290 | A-2 | A-11 | — | — |
| Cu-291 | A-2 | A-12 | — | — |
| Cu-292 | A-2 | A-14 | — | — |
| Cu-293 | A-2 | A-15 | — | — |
| Cu-294 | A-2 | A-16 | — | — |
| Cu-295 | A-2 | A-17 | — | — |
| Cu-296 | A-2 | A-18 | — | — |
| Cu-297 | A-2 | A-19 | — | — |
| Cu-298 | A-2 | A-20 | — | — |
| Cu-299 | A-2 | A-21 | — | — |
| Cu-300 | A-2 | A-22 | — | — |

TABLE 12

| Copper complex | Compound i | Compound ii | Compound iii | Compound iv |
|---|---|---|---|---|
| Cu-301 | A-2 | A-23 | — | — |
| Cu-302 | A-2 | A-24 | — | — |
| Cu-303 | A-2 | A-25 | — | — |
| Cu-304 | A-2 | A-26 | — | — |
| Cu-305 | A-2 | A-27 | — | — |
| Cu-306 | A-2 | A-28 | — | — |
| Cu-307 | A-2 | A-29 | — | — |
| Cu-308 | A-2 | A-30 | — | — |
| Cu-309 | A-2 | A-31 | — | — |
| Cu-310 | A-2 | A-32 | — | — |
| Cu-311 | A-2 | A-33 | — | — |
| Cu-312 | A-2 | A-34 | — | — |
| Cu-313 | A-2 | A-35 | — | — |
| Cu-314 | A-2 | A-36 | — | — |
| Cu-315 | A-2 | A-37 | — | — |
| Cu-316 | A-2 | A-38 | — | — |
| Cu-317 | A-2 | A-39 | — | — |
| Cu-318 | A-2 | A-40 | — | — |
| Cu-319 | A-2 | A-41 | — | — |
| Cu-320 | A-2 | A-42 | — | — |
| Cu-321 | A-2 | A-43 | — | — |
| Cu-322 | A-2 | A-44 | — | — |
| Cu-323 | A-2 | A-45 | — | — |
| Cu-324 | A-2 | A-46 | — | — |
| Cu-325 | A-2 | A-47 | — | — |
| Cu-326 | A-2 | A-48 | — | — |
| Cu-327 | A-2 | A-49 | — | — |
| Cu-328 | A-2 | A-50 | — | — |
| Cu-329 | A-2 | A-51 | — | — |
| Cu-330 | A-2 | A-52 | — | — |
| Cu-331 | A-2 | A-53 | — | — |
| Cu-332 | A-2 | A-54 | — | — |
| Cu-333 | A-2 | A-55 | — | — |
| Cu-334 | A-2 | A-56 | — | — |
| Cu-335 | A-2 | A-57 | — | — |
| Cu-336 | A-2 | A-58 | — | — |
| Cu-337 | A-2 | A-59 | — | — |

TABLE 12-continued

| Copper complex | Compound i | Sulfonic acid Compound ii | Compound iii | Compound iv |
|---|---|---|---|---|
| Cu-338 | A-2 | A-60 | — | — |
| Cu-339 | A-2 | A-61 | — | — |
| Cu-340 | A-2 | A-63 | — | — |
| Cu-341 | A-2 | A-64 | — | — |
| Cu-342 | A-2 | A-65 | — | — |
| Cu-343 | A-2 | A-66 | — | — |
| Cu-344 | A-2 | A-67 | — | — |
| Cu-345 | A-2 | A-68 | — | — |
| Cu-346 | A-2 | A-69 | — | — |
| Cu-347 | A-2 | A-70 | — | — |
| Cu-348 | A-2 | A-71 | — | — |
| Cu-349 | A-2 | A-72 | — | — |
| Cu-350 | A-2 | A-73 | — | — |
| Cu-351 | A-2 | A-75 | — | — |
| Cu-352 | A-2 | A-76 | — | — |
| Cu-353 | A-2 | A-78 | — | — |
| Cu-354 | A-2 | A-79 | — | — |
| Cu-355 | A-2 | A-80 | — | — |
| Cu-356 | A-2 | A-81 | — | — |
| Cu-357 | A-2 | A-83 | — | — |
| Cu-358 | A-2 | A-84 | — | — |
| Cu-359 | A-2 | A-85 | — | — |
| Cu-360 | A-2 | A-86 | — | — |

TABLE 13

| Copper complex | Compound i | Sulfonic acid Compound ii | Compound iii | Compound iv |
|---|---|---|---|---|
| Cu-361 | A-2 | A-87 | — | — |
| Cu-362 | A-2 | A-88 | — | — |
| Cu-363 | A-2 | A-89 | — | — |
| Cu-364 | A-2 | A-90 | — | — |
| Cu-365 | A-2 | A-92 | — | — |
| Cu-366 | A-2 | A-93 | — | — |
| Cu-367 | A-2 | A-94 | — | — |
| Cu-368 | A-2 | A-95 | — | — |
| Cu-369 | A-2 | A-97 | — | — |
| Cu-370 | A-2 | A-98 | — | — |
| Cu-371 | A-2 | A-99 | — | — |
| Cu-372 | A-2 | A-100 | — | — |
| Cu-373 | A-2 | A-101 | — | — |
| Cu-374 | A-2 | A-102 | — | — |
| Cu-375 | A-2 | A-103 | — | — |
| Cu-376 | A-2 | A-104 | — | — |
| Cu-377 | A-2 | A-106 | — | — |
| Cu-378 | A-2 | A-108 | — | — |
| Cu-379 | A-2 | A-109 | — | — |
| Cu-380 | A-2 | A110 | — | — |
| Cu-381 | A-2 | A-114 | — | — |
| Cu-382 | A-2 | A-115 | — | — |
| Cu-383 | A-2 | A-116 | — | — |
| Cu-384 | A-2 | A-117 | — | — |
| Cu-385 | A-2 | A-118 | — | — |
| Cu-386 | A-2 | A-119 | — | — |
| Cu-387 | A-2 | A-120 | — | — |
| Cu-388 | A-2 | A-121 | — | — |
| Cu-389 | A-2 | A-122 | — | — |
| Cu-390 | A-2 | A-123 | — | — |
| Cu-391 | A-2 | A-124 | — | — |
| Cu-392 | A-2 | A-125 | — | — |
| Cu-393 | A-2 | A-126 | — | — |
| Cu-394 | A-2 | A-127 | — | — |
| Cu-395 | A-2 | A-128 | — | — |
| Cu-396 | A-2 | A-129 | — | — |
| Cu-397 | A-2 | A-130 | — | — |
| Cu-398 | A-2 | A-13 | A-1 | — |
| Cu-399 | A-2 | A-13 | A-2 | — |
| Cu-400 | A-2 | A-13 | A-3 | — |
| Cu-401 | A-2 | A-13 | A-4 | — |
| Cu-402 | A-2 | A-13 | A-5 | — |
| Cu-403 | A-2 | A-13 | A-6 | — |

TABLE 13-continued

| Copper complex | Compound i | Sulfonic acid Compound ii | Compound iii | Compound iv |
|---|---|---|---|---|
| Cu-404 | A-2 | A-13 | A-7 | — |
| Cu-405 | A-2 | A-13 | A-8 | — |
| Cu-406 | A-2 | A-13 | A-9 | — |
| Cu-407 | A-2 | A-13 | A-10 | — |
| Cu-408 | A-2 | A-13 | A-11 | — |
| Cu-409 | A-2 | A-13 | A-12 | — |
| Cu-410 | A-2 | A-13 | A-13 | — |
| Cu-411 | A-2 | A-13 | A-14 | — |
| Cu-412 | A-2 | A-13 | A-15 | — |
| Cu-413 | A-2 | A-13 | A-16 | — |
| Cu-414 | A-2 | A-13 | A-17 | — |
| Cu-415 | A-2 | A-13 | A-18 | — |
| Cu-416 | A-2 | A-13 | A-19 | — |
| Cu-417 | A-2 | A-13 | A-20 | — |
| Cu-418 | A-2 | A-13 | A-21 | — |
| Cu-419 | A-2 | A-13 | A-22 | — |
| Cu-420 | A-2 | A-13 | A-23 | — |

TABLE 14

| Copper complex | Compound i | Sulfonic acid Compound ii | Compound iii | Compound iv |
|---|---|---|---|---|
| Cu-421 | A-2 | A-13 | A-24 | — |
| Cu-422 | A-2 | A-13 | A-25 | — |
| Cu-423 | A-2 | A-13 | A-26 | — |
| Cu-424 | A-2 | A-13 | A-27 | — |
| Cu-425 | A-2 | A-13 | A-28 | — |
| Cu-426 | A-2 | A-13 | A-29 | — |
| Cu-427 | A-2 | A-13 | A-30 | — |
| Cu-428 | A-2 | A-13 | A-31 | — |
| Cu-429 | A-2 | A-13 | A-32 | — |
| Cu-430 | A-2 | A-13 | A-33 | — |
| Cu-431 | A-2 | A-13 | A-34 | — |
| Cu-432 | A-2 | A-13 | A-35 | — |
| Cu-433 | A-2 | A-13 | A-36 | — |
| Cu-434 | A-2 | A-13 | A-37 | — |
| Cu-435 | A-2 | A-13 | A-38 | — |
| Cu-436 | A-2 | A-13 | A-39 | — |
| Cu-437 | A-2 | A-13 | A-40 | — |
| Cu-438 | A-2 | A-13 | A-41 | — |
| Cu-439 | A-2 | A-13 | A-42 | — |
| Cu-440 | A-2 | A-13 | A-43 | — |
| Cu-441 | A-2 | A-13 | A-44 | — |
| Cu-442 | A-2 | A-13 | A-45 | — |
| Cu-443 | A-2 | A-13 | A-46 | — |
| Cu-444 | A-2 | A-13 | A-47 | — |
| Cu-445 | A-2 | A-13 | A-48 | — |
| Cu-446 | A-2 | A-13 | A-49 | — |
| Cu-447 | A-2 | A-13 | A-50 | — |
| Cu-448 | A-2 | A-13 | A-51 | — |
| Cu-449 | A-2 | A-13 | A-52 | — |
| Cu-450 | A-2 | A-13 | A-53 | — |
| Cu-451 | A-2 | A-13 | A-54 | — |
| Cu-452 | A-2 | A-13 | A-55 | — |
| Cu-453 | A-2 | A-13 | A-56 | — |
| Cu-454 | A-2 | A-13 | A-57 | — |
| Cu-455 | A-2 | A-13 | A-58 | — |
| Cu-456 | A-2 | A-13 | A-59 | — |
| Cu-457 | A-2 | A-13 | A-61 | — |
| Cu-458 | A-2 | A-13 | A-62 | — |
| Cu-459 | A-2 | A-13 | A-63 | — |
| Cu-460 | A-2 | A-13 | A-64 | — |
| Cu-461 | A-2 | A-13 | A-65 | — |
| Cu-462 | A-2 | A-13 | A-66 | — |
| Cu-463 | A-2 | A-13 | A-67 | — |
| Cu-464 | A-2 | A-13 | A-68 | — |
| Cu-465 | A-2 | A-13 | A-69 | — |
| Cu-466 | A-2 | A-13 | A-70 | — |
| Cu-467 | A-2 | A-13 | A-71 | — |
| Cu-468 | A-2 | A-13 | A-72 | — |
| Cu-469 | A-2 | A-13 | A-73 | — |

TABLE 14-continued

| Copper complex | Sulfonic acid | | | |
|---|---|---|---|---|
| | Compound i | Compound ii | Compound iii | Compound iv |
| Cu-470 | A-2 | A-13 | A-74 | — |
| Cu-471 | A-2 | A-13 | A-75 | — |
| Cu-472 | A-2 | A-13 | A-76 | — |
| Cu-473 | A-2 | A-13 | A-77 | — |
| Cu-474 | A-2 | A-13 | A-78 | — |
| Cu-475 | A-2 | A-13 | A-79 | — |
| Cu-476 | A-2 | A-13 | A-80 | — |
| Cu-477 | A-2 | A-13 | A-81 | — |
| Cu-478 | A-2 | A-13 | A-82 | — |
| Cu-479 | A-2 | A-13 | A-83 | — |
| Cu-480 | A-2 | A-13 | A-84 | — |

TABLE 15

| Copper complex | Sulfonic acid | | | |
|---|---|---|---|---|
| | Compound i | Compound ii | Compound iii | Compound iv |
| Cu-481 | A-2 | A-13 | A-85 | — |
| Cu-482 | A-2 | A-13 | A-86 | — |
| Cu-483 | A-2 | A-13 | A-87 | — |
| Cu-484 | A-2 | A-13 | A-88 | — |
| Cu-485 | A-2 | A-13 | A-89 | — |
| Cu-486 | A-2 | A-13 | A-90 | — |
| Cu-487 | A-2 | A-13 | A-91 | — |
| Cu-488 | A-2 | A-13 | A-92 | — |
| Cu-489 | A-2 | A-13 | A-93 | — |
| Cu-490 | A-2 | A-13 | A-94 | — |
| Cu-491 | A-2 | A-13 | A-95 | — |
| Cu-492 | A-2 | A-13 | A-96 | — |
| Cu-493 | A-2 | A-13 | A-97 | — |
| Cu-494 | A-2 | A-13 | A-98 | — |
| Cu-495 | A-2 | A-13 | A-99 | — |
| Cu-496 | A-2 | A-13 | A-100 | — |
| Cu-497 | A-2 | A-13 | A-101 | — |
| Cu-498 | A-2 | A-13 | A-102 | — |
| Cu-499 | A-2 | A-13 | A-103 | — |
| Cu-500 | A-2 | A-13 | A-104 | — |
| Cu-501 | A-2 | A-13 | A-105 | — |
| Cu-502 | A-2 | A-13 | A-106 | — |
| Cu-503 | A-2 | A-13 | A-107 | — |
| Cu-504 | A-2 | A-13 | A-108 | — |
| Cu-505 | A-2 | A-13 | A-109 | — |
| Cu-506 | A-2 | A-13 | A-110 | — |
| Cu-507 | A-2 | A-13 | A-111 | — |
| Cu-508 | A-2 | A-13 | A-112 | — |
| Cu-509 | A-2 | A-13 | A-113 | — |
| Cu-510 | A-2 | A-13 | A-114 | — |
| Cu-511 | A-2 | A-13 | A-115 | — |
| Cu-512 | A-2 | A-13 | A-116 | — |
| Cu-513 | A-2 | A-13 | A-117 | — |
| Cu-514 | A-2 | A-13 | A-118 | — |
| Cu-515 | A-2 | A-13 | A-119 | — |
| Cu-516 | A-2 | A-13 | A-120 | — |
| Cu-517 | A-2 | A-13 | A-121 | — |
| Cu-518 | A-2 | A-13 | A-122 | — |
| Cu-519 | A-2 | A-13 | A-123 | — |
| Cu-520 | A-2 | A-13 | A-124 | — |
| Cu-521 | A-2 | A-13 | A-125 | — |
| Cu-522 | A-2 | A-13 | A-126 | — |
| Cu-523 | A-2 | A-13 | A-127 | — |
| Cu-524 | A-2 | A-13 | A-128 | — |
| Cu-525 | A-2 | A-13 | A-129 | — |
| Cu-526 | A-2 | A-13 | A-130 | — |
| Cu-527 | A-2 | A-62 | A-1 | — |
| Cu-528 | A-2 | A-62 | A-2 | — |
| Cu-529 | A-2 | A-62 | A-3 | — |
| Cu-530 | A-2 | A-62 | A-4 | — |
| Cu-531 | A-2 | A-62 | A-5 | — |
| Cu-532 | A-2 | A-62 | A-6 | — |
| Cu-533 | A-2 | A-62 | A-7 | — |
| Cu-534 | A-2 | A-62 | A-8 | — |
| Cu-535 | A-2 | A-62 | A-9 | — |
| Cu-536 | A-2 | A-62 | A-10 | — |
| Cu-537 | A-2 | A-62 | A-11 | — |
| Cu-538 | A-2 | A-62 | A-12 | — |
| Cu-539 | A-2 | A-62 | A-13 | — |
| Cu-540 | A-2 | A-62 | A-14 | — |

TABLE 16

| Copper complex | Sulfonic acid | | | |
|---|---|---|---|---|
| | Compound i | Compound ii | Compound iii | Compound iv |
| Cu-541 | A-2 | A-62 | A-15 | — |
| Cu-542 | A-2 | A-62 | A-16 | — |
| Cu-543 | A-2 | A-62 | A-17 | — |
| Cu-544 | A-2 | A-62 | A-18 | — |
| Cu-545 | A-2 | A-62 | A-19 | — |
| Cu-546 | A-2 | A-62 | A-20 | — |
| Cu-547 | A-2 | A-62 | A-21 | — |
| Cu-578 | A-2 | A-62 | A-22 | — |
| Cu-549 | A-2 | A-62 | A-23 | — |
| Cu-550 | A-2 | A-62 | A-24 | — |
| Cu-551 | A-2 | A-62 | A-25 | — |
| Cu-552 | A-2 | A-62 | A-26 | — |
| Cu-553 | A-2 | A-62 | A-27 | — |
| Cu-554 | A-2 | A-62 | A-28 | — |
| Cu-555 | A-2 | A-62 | A-29 | — |
| Cu-556 | A-2 | A-62 | A-30 | — |
| Cu-557 | A-2 | A-62 | A-31 | — |
| Cu-558 | A-2 | A-62 | A-32 | — |
| Cu-559 | A-2 | A-62 | A-33 | — |
| Cu-560 | A-2 | A-62 | A-34 | — |
| Cu-561 | A-2 | A-62 | A-35 | — |
| Cu-562 | A-2 | A-62 | A-36 | — |
| Cu-563 | A-2 | A-62 | A-37 | — |
| Cu-564 | A-2 | A-62 | A-38 | — |
| Cu-565 | A-2 | A-62 | A-39 | — |
| Cu-566 | A-2 | A-62 | A-40 | — |
| Cu-567 | A-2 | A-62 | A-41 | — |
| Cu-568 | A-2 | A-62 | A-42 | — |
| Cu-569 | A-2 | A-62 | A-43 | — |
| Cu-570 | A-2 | A-62 | A-44 | — |
| Cu-571 | A-2 | A-62 | A-45 | — |
| Cu-572 | A-2 | A-62 | A-46 | — |
| Cu-573 | A-2 | A-62 | A-47 | — |
| Cu-574 | A-2 | A-62 | A-48 | — |
| Cu-575 | A-2 | A-62 | A-49 | — |
| Cu-576 | A-2 | A-62 | A-50 | — |
| Cu-577 | A-2 | A-62 | A-51 | — |
| Cu-578 | A-2 | A-62 | A-52 | — |
| Cu-579 | A-2 | A-62 | A-53 | — |
| Cu-580 | A-2 | A-62 | A-54 | — |
| Cu-581 | A-2 | A-62 | A-55 | — |
| Cu-582 | A-2 | A-62 | A-56 | — |
| Cu-583 | A-2 | A-62 | A-57 | — |
| Cu-584 | A-2 | A-62 | A-58 | — |
| Cu-585 | A-2 | A-62 | A-59 | — |
| Cu-586 | A-2 | A-62 | A-60 | — |
| Cu-587 | A-2 | A-62 | A-61 | — |
| Cu-588 | A-2 | A-62 | A-62 | — |
| Cu-589 | A-2 | A-62 | A-63 | — |
| Cu-590 | A-2 | A-62 | A-64 | — |
| Cu-591 | A-2 | A-62 | A-65 | — |
| Cu-592 | A-2 | A-62 | A-66 | — |
| Cu-593 | A-2 | A-62 | A-67 | — |
| Cu-594 | A-2 | A-62 | A-68 | — |
| Cu-595 | A-2 | A-62 | A-69 | — |
| Cu-596 | A-2 | A-62 | A-70 | — |
| Cu-597 | A-2 | A-62 | A-71 | — |
| Cu-598 | A-2 | A-62 | A-72 | — |
| Cu-599 | A-2 | A-62 | A-73 | — |
| Cu-600 | A-2 | A-62 | A-74 | — |

TABLE 17

| Copper complex | Compound i | Sulfonic acid Compound ii | Compound iii | Compound iv |
|---|---|---|---|---|
| Cu-601 | A-2 | A-62 | A-75 | — |
| Cu-602 | A-2 | A-62 | A-76 | — |
| Cu-603 | A-2 | A-62 | A-77 | — |
| Cu-604 | A-2 | A-62 | A-78 | — |
| Cu-605 | A-2 | A-62 | A-79 | — |
| Cu-606 | A-2 | A-62 | A-80 | — |
| Cu-607 | A-2 | A-62 | A-81 | — |
| Cu-608 | A-2 | A-62 | A-82 | — |
| Cu-609 | A-2 | A-62 | A-83 | — |
| Cu-610 | A-2 | A-62 | A-84 | — |
| Cu-611 | A-2 | A-62 | A-85 | — |
| Cu-612 | A-2 | A-62 | A-86 | — |
| Cu-613 | A-2 | A-62 | A-87 | — |
| Cu-614 | A-2 | A-62 | A-88 | — |
| Cu-615 | A-2 | A-62 | A-89 | — |
| Cu-616 | A-2 | A-62 | A-90 | — |
| Cu-617 | A-2 | A-62 | A-91 | — |
| Cu-618 | A-2 | A-62 | A-92 | — |
| Cu-619 | A-2 | A-62 | A-93 | — |
| Cu-620 | A-2 | A-62 | A-94 | — |
| Cu-621 | A-2 | A-62 | A-95 | — |
| Cu-622 | A-2 | A-62 | A-96 | — |
| Cu-623 | A-2 | A-62 | A-97 | — |
| Cu-624 | A-2 | A-62 | A-98 | — |
| Cu-625 | A-2 | A-62 | A-99 | — |
| Cu-626 | A-2 | A-62 | A-100 | — |
| Cu-627 | A-2 | A-62 | A-101 | — |
| Cu-628 | A-2 | A-62 | A-102 | — |
| Cu-629 | A-2 | A-62 | A-103 | — |
| Cu-630 | A-2 | A-62 | A-104 | — |
| Cu-631 | A-2 | A-62 | A-106 | — |
| Cu-632 | A-2 | A-62 | A-108 | — |
| Cu-633 | A-2 | A-62 | A-109 | — |
| Cu-634 | A-2 | A-62 | A-110 | — |
| Cu-635 | A-2 | A-62 | A-111 | — |
| Cu-636 | A-2 | A-62 | A-113 | — |
| Cu-637 | A-2 | A-62 | A-114 | — |
| Cu-638 | A-2 | A-62 | A-115 | — |
| Cu-639 | A-2 | A-62 | A-116 | — |
| Cu-640 | A-2 | A-62 | A-117 | — |
| Cu-641 | A-2 | A-62 | A-118 | — |
| Cu-642 | A-2 | A-62 | A-119 | — |
| Cu-643 | A-2 | A-62 | A-120 | — |
| Cu-644 | A-2 | A-62 | A-121 | — |
| Cu-645 | A-2 | A-62 | A-122 | — |
| Cu-646 | A-2 | A-62 | A-123 | — |
| Cu-647 | A-2 | A-62 | A-124 | — |
| Cu-648 | A-2 | A-62 | A-125 | — |
| Cu-649 | A-2 | A-62 | A-126 | — |
| Cu-650 | A-2 | A-62 | A-127 | — |
| Cu-651 | A-2 | A-62 | A-128 | — |
| Cu-652 | A-2 | A-62 | A-129 | — |
| Cu-653 | A-2 | A-62 | A-130 | — |
| Cu-654 | A-2 | A-13 | A-62 | A-1 |
| Cu-655 | A-2 | A-13 | A-62 | A-2 |
| Cu-656 | A-2 | A-13 | A-62 | A-3 |
| Cu-657 | A-2 | A-13 | A-62 | A-4 |
| Cu-658 | A-2 | A-13 | A-62 | A-5 |
| Cu-659 | A-2 | A-13 | A-62 | A-6 |
| Cu-660 | A-2 | A-13 | A-62 | A-7 |

TABLE 18

| Copper complex | Compound i | Sulfonic acid Compound ii | Compound iii | Compound iv |
|---|---|---|---|---|
| Cu-661 | A-2 | A-13 | A-62 | A-8 |
| Cu-662 | A-2 | A-13 | A-62 | A-9 |
| Cu-663 | A-2 | A-13 | A-62 | A-10 |
| Cu-664 | A-2 | A-13 | A-62 | A-11 |
| Cu-665 | A-2 | A-13 | A-62 | A-12 |
| Cu-666 | A-2 | A-13 | A-62 | A-13 |
| Cu-667 | A-2 | A-13 | A-62 | A-14 |
| Cu-668 | A-2 | A-13 | A-62 | A-15 |
| Cu-669 | A-2 | A-13 | A-62 | A-16 |
| Cu-670 | A-2 | A-13 | A-62 | A-17 |
| Cu-671 | A-2 | A-13 | A-62 | A-18 |
| Cu-672 | A-2 | A-13 | A-62 | A-19 |
| Cu-673 | A-2 | A-13 | A-62 | A-20 |
| Cu-674 | A-2 | A-13 | A-62 | A-21 |
| Cu-675 | A-2 | A-13 | A-62 | A-22 |
| Cu-676 | A-2 | A-13 | A-62 | A-23 |
| Cu-677 | A-2 | A-13 | A-62 | A-24 |
| Cu-678 | A-2 | A-13 | A-62 | A-25 |
| Cu-679 | A-2 | A-13 | A-62 | A-26 |
| Cu-680 | A-2 | A-13 | A-62 | A-27 |
| Cu-681 | A-2 | A-13 | A-62 | A-28 |
| Cu-682 | A-2 | A-13 | A-62 | A-29 |
| Cu-683 | A-2 | A-13 | A-62 | A-30 |
| Cu-684 | A-2 | A-13 | A-62 | A-31 |
| Cu-685 | A-2 | A-13 | A-62 | A-32 |
| Cu-686 | A-2 | A-13 | A-62 | A-33 |
| Cu-687 | A-2 | A-13 | A-62 | A-34 |
| Cu-688 | A-2 | A-13 | A-62 | A-35 |
| Cu-689 | A-2 | A-13 | A-62 | A-36 |
| Cu-690 | A-2 | A-13 | A-62 | A-37 |
| Cu-700 | A-2 | A-13 | A-62 | A-38 |
| Cu-701 | A-2 | A-13 | A-62 | A-39 |
| Cu-702 | A-2 | A-13 | A-62 | A-40 |
| Cu-703 | A-2 | A-13 | A-62 | A-41 |
| Cu-704 | A-2 | A-13 | A-62 | A-42 |
| Cu-705 | A-2 | A-13 | A-62 | A-43 |
| Cu-706 | A-2 | A-13 | A-62 | A-44 |
| Cu-707 | A-2 | A-13 | A-62 | A-45 |
| Cu-708 | A-2 | A-13 | A-62 | A-46 |
| Cu-709 | A-2 | A-13 | A-62 | A-47 |
| Cu-710 | A-2 | A-13 | A-62 | A-48 |
| Cu-711 | A-2 | A-13 | A-62 | A-49 |
| Cu-712 | A-2 | A-13 | A-62 | A-50 |
| Cu-713 | A-2 | A-13 | A-62 | A-51 |
| Cu-714 | A-2 | A-13 | A-62 | A-52 |
| Cu-715 | A-2 | A-13 | A-62 | A-53 |
| Cu-716 | A-2 | A-13 | A-62 | A-54 |
| Cu-717 | A-2 | A-13 | A-62 | A-55 |
| Cu-718 | A-2 | A-13 | A-62 | A-56 |
| Cu-719 | A-2 | A-13 | A-62 | A-57 |
| Cu-720 | A-2 | A-13 | A-62 | A-58 |
| Cu-721 | A-2 | A-13 | A-62 | A-59 |
| Cu-722 | A-2 | A-13 | A-62 | A-60 |
| Cu-723 | A-2 | A-13 | A-62 | A-61 |
| Cu-724 | A-2 | A-13 | A-62 | A-62 |
| Cu-725 | A-2 | A-13 | A-62 | A-63 |
| Cu-726 | A-2 | A-13 | A-62 | A-64 |
| Cu-727 | A-2 | A-13 | A-62 | A-65 |
| Cu-728 | A-2 | A-13 | A-62 | A-66 |
| Cu-729 | A-2 | A-13 | A-62 | A-67 |

TABLE 19

| Copper complex | Compound i | Sulfonic acid Compound ii | Compound iii | Compound iv |
|---|---|---|---|---|
| Cu-730 | A-2 | A-13 | A-62 | A-68 |
| Cu-731 | A-2 | A-13 | A-62 | A-69 |
| Cu-732 | A-2 | A-13 | A-62 | A-70 |
| Cu-733 | A-2 | A-13 | A-62 | A-71 |
| Cu-734 | A-2 | A-13 | A-62 | A-72 |
| Cu-735 | A-2 | A-13 | A-62 | A-73 |
| Cu-736 | A-2 | A-13 | A-62 | A-74 |
| Cu-737 | A-2 | A-13 | A-62 | A-75 |
| Cu-738 | A-2 | A-13 | A-62 | A-76 |
| Cu-739 | A-2 | A-13 | A-62 | A-77 |
| Cu-740 | A-2 | A-13 | A-62 | A-78 |
| Cu-741 | A-2 | A-13 | A-62 | A-79 |

TABLE 19-continued

| Copper complex | Sulfonic acid | | | |
|---|---|---|---|---|
| | Compound i | Compound ii | Compound iii | Compound iv |
| Cu-742 | A-2 | A-13 | A-62 | A-80 |
| Cu-743 | A-2 | A-13 | A-62 | A-81 |
| Cu-744 | A-2 | A-13 | A-62 | A-82 |
| Cu-745 | A-2 | A-13 | A-62 | A-83 |
| Cu-746 | A-2 | A-13 | A-62 | A-84 |
| Cu-747 | A-2 | A-13 | A-62 | A-85 |
| Cu-748 | A-2 | A-13 | A-62 | A-86 |
| Cu-749 | A-2 | A-13 | A-62 | A-87 |
| Cu-750 | A-2 | A-13 | A-62 | A-88 |
| Cu-751 | A-2 | A-13 | A-62 | A-89 |
| Cu-752 | A-2 | A-13 | A-62 | A-90 |
| Cu-753 | A-2 | A-13 | A-62 | A-91 |
| Cu-754 | A-2 | A-13 | A-62 | A-92 |
| Cu-755 | A-2 | A-13 | A-62 | A-93 |
| Cu-756 | A-2 | A-13 | A-62 | A-94 |
| Cu-757 | A-2 | A-13 | A-62 | A-95 |
| Cu-758 | A-2 | A-13 | A-62 | A-96 |
| Cu-759 | A-2 | A-13 | A-62 | A-97 |
| Cu-760 | A-2 | A-13 | A-62 | A-98 |
| Cu-761 | A-2 | A-13 | A-62 | A-99 |
| Cu-762 | A-2 | A-13 | A-62 | A-100 |
| Cu-763 | A-2 | A-13 | A-62 | A-101 |
| Cu-764 | A-2 | A-13 | A-62 | A-102 |
| Cu-765 | A-2 | A-13 | A-62 | A-103 |
| Cu-766 | A-2 | A-13 | A-62 | A-104 |
| Cu-767 | A-2 | A-13 | A-62 | A-106 |
| Cu-768 | A-2 | A-13 | A-62 | A-108 |
| Cu-769 | A-2 | A-13 | A-62 | A-109 |
| Cu-770 | A-2 | A-13 | A-62 | A-110 |
| Cu-771 | A-2 | A-13 | A-62 | A-111 |
| Cu-772 | A-2 | A-13 | A-62 | A-113 |
| Cu-773 | A-2 | A-13 | A-62 | A-114 |
| Cu-774 | A-2 | A-13 | A-62 | A-115 |
| Cu-775 | A-2 | A-13 | A-62 | A-116 |
| Cu-776 | A-2 | A-13 | A-62 | A-117 |
| Cu-777 | A-2 | A-13 | A-62 | A-118 |
| Cu-778 | A-2 | A-13 | A-62 | A-119 |
| Cu-779 | A-2 | A-13 | A-62 | A-120 |
| Cu-780 | A-2 | A-13 | A-62 | A-121 |
| Cu-781 | A-2 | A-13 | A-62 | A-122 |
| Cu-782 | A-2 | A-13 | A-62 | A-123 |
| Cu-783 | A-2 | A-13 | A-62 | A-124 |
| Cu-784 | A-2 | A-13 | A-62 | A-125 |
| Cu-785 | A-2 | A-13 | A-62 | A-126 |
| Cu-786 | A-2 | A-13 | A-62 | A-127 |
| Cu-787 | A-2 | A-13 | A-62 | A-128 |
| Cu-788 | A-2 | A-13 | A-62 | A-129 |
| Cu-789 | A-2 | A-13 | A-62 | A-130 |

The copper in the sulfonic acid copper complex of the present invention is generally divalent copper.

As the above-described copper component, it is possible to use copper or a copper-containing compound. As the copper-containing compound, it is possible to use, for example, copper oxide or a copper salt. The copper salt is preferably monovalent or divalent copper and more preferably divalent copper. The copper salt is more preferably copper acetate, copper chloride, copper formate, copper stearate, copper benzoate, copper ethyl acetoacetate, copper pyrophosphate, copper naphthenate, copper citrate, cupric nitrate, copper sulfate, copper carbonate, copper chlorate, copper (meth)acrylate, or copper perchlorate and still more preferably copper acetate, copper chloride, copper sulfate, copper benzoate, or copper (meth)acrylate.

The salt of the sulfonic acid used in the present invention is preferably, for example, a metal salt and specific examples thereof include sodium salts, potassium salts, magnesium salts, calcium salts, borate salts, and the like.

The reaction ratio during the reaction between the copper component and the above-described sulfonic acid or salt thereof is preferably set to a range of 1:1 to 1:6 (the copper component:the sulfonic acid or salt thereof) in terms of molar ratio.

In addition, the reaction conditions during the reaction between the copper component and the above-described sulfonic acid or salt thereof are preferably, for example, 0° C. to 140° C. and 10 minutes or longer.

The sulfonic acid copper complex of the present invention has the maximum absorption wavelength in a near-infrared wavelength range of 700 nm to 2500 nm, preferably has the maximum absorption wavelength in a range of 720 nm to 950 nm, still more preferably has the maximum absorption wavelength in a range of 750 nm to 900 nm, and particularly preferably has the maximum absorption wavelength in a range of 790 nm to 880 nm. The maximum absorption wavelength can be measured using, for example, a Cary 5000 UV-Vis-NIR (spectrophotometer, manufactured by Agilent Technologies Japan, Ltd.).

<Near-Infrared-Absorbing Composition>

The near-infrared-absorbing composition of the present invention (hereinafter, also referred to as the composition of the present invention) includes the above-described sulfonic acid copper complex.

The composition of the present invention includes a copper complex obtained by reacting two or more kinds of the sulfonic acids represented by General Formula (I) or salts thereof with the copper component and a solvent.

In addition, the composition of the present invention may include a copper complex which includes copper as the central metal and includes the sulfonic acids represented by General Formula (I) as ligands or a copper complex having the structures represented by General Formula (II) that are different from each other and a solvent.

The composition of the present invention preferably includes the copper complex obtained by reacting three or more kinds of the sulfonic acids represented by General Formula (I) or salts thereof with the copper component, three or more kinds of copper complexes which include the sulfonic acids represented by General Formula (I) as ligands that are different from each other, or three or more kinds of copper complexes having the structures represented by General Formula (II) that are different from each other.

When the above-described sulfonic acid copper complex of the present invention is used, the composition of the present invention is capable of improving heat resistance while maintaining strong near-infrared shielding properties when a cured film is produced using the near-infrared-absorbing composition. In addition, when the above-described sulfonic acid copper complex of the first embodiment is used, the composition of the present invention is capable of further improving the solubility of the near-infrared-absorbing composition in a solvent (particularly, an organic solvent). In addition, when the above-described sulfonic acid copper complex of the second embodiment is used, the composition of the present invention is capable of further improving the solubility of the near-infrared-absorbing composition in a solvent (particularly, water).

Hereinafter, particularly preferred aspects of the composition of the present invention will be exemplified but the composition is not limited thereto.

<1> A composition including the sulfonic acid copper complex (1A), a composition including the sulfonic acid copper complex (1B), a composition including the sulfonic acid copper complex (1C), a composition including the sulfonic acid copper complex (1D), a composition including the sulfonic acid copper complex (2A), and a composition including the sulfonic acid copper complex (2B).

<2> In a composition including a copper complex obtained by reacting two kinds of the sulfonic acids represented by General Formula (I), $R^1$ in at least one kind of the sulfonic acid represented by General Formula (I) is an unsubstituted alkyl group and $R^1$ in at least one kind of the other sulfonic acid represented by General Formula (I) is a group described below.

An aryl group having a substituent,
an alkyl group substituted with a fluorine atom, or
—$(CH_2)_m$— (m is an integer from 1 to 10), a cyclic alkylene group having 5 to 10 carbon atoms, or a group obtained by combining the above-described group and at least one of —O—, —COO—, —NH—, and —CO—.

The sulfonic acid copper complex used in the composition of the present invention, as described above, is in a form of a copper complex (copper compound) in which the sulfonic acid or a salt thereof coordinates copper which is the central metal. In the sulfonic acid copper complex, the copper is generally divalent copper and the copper can be obtained by, for example, mixing and reacting the above-described sulfonic acid or a salt thereof with a copper component (copper or a compound including copper). Here, when the copper component and the sulfonic acid can be detected from the composition of the present invention, it is possible to say that the sulfonic acid copper complex is formed in the composition of the present invention. For example, as a method for detecting copper and the sulfonic acid from the composition of the present invention, ICP emission spectrometry can be used and copper and the sulfonic acid can be detected using this method.

Regarding the amount of the sulfonic acid copper complex blended in the composition of the present invention, the composition of the present invention preferably includes the sulfonic acid copper complex at a ratio in a range of 5% by mass to 60% by mass and more preferably includes the sulfonic acid copper complex at a ratio in a range of 10% by mass to 40% by mass.

The amount of the sulfonic acid copper complex blended in the solid content of the composition of the present invention is preferably in a range of 30% by mass to 90% by mass, more preferably in a range of 35% by mass to 85% by mass, and still more preferably in a range of 40% by mass to 80% by mass.

The composition of the present invention may, substantially, include two or more kinds of the above-described sulfonic acid copper complexes. Here, the expression of "substantially including" means that the amount of the sulfonic acid copper complex represented by Formula (I) or (II) blended in the composition of the present invention is 1 mass % or less and the amount thereof is preferably 0.1 mass % or less and particularly preferably 0 mass %.

In addition, the composition of the present invention preferably includes a copper complex obtained by reacting a compound having two or more acid groups or a salt thereof with a copper component.

The compound having two or more acid groups or a salt thereof is preferably represented by General Formula (i) described below.

$R^1$—$(X^1)_n$  General Formula (i)

(In General Formula (i), $R^1$ represents an n-valent organic group, $X^1$ represents an acid group, and n represents an integer from 2 to 6.)

In General Formula (i), the n-valent organic group is preferably a hydrocarbon group or an oxyalkylene group and more preferably an aliphatic hydrocarbon group or an aromatic hydrocarbon group. The hydrocarbon group may have a substituent and examples of the substituent include a halogen atom (preferably a fluorine atom), a (meth)acryloyl group, and groups having an unsaturated double bond.

In the case of a divalent hydrocarbon group, an alkylene group, an arylene group, or an oxyalkylene group is preferred and an arylene group is more preferred. In addition, in the case of a tri- or more-valent hydrocarbon group, trivalent hydrocarbon groups that correspond to the above-described hydrocarbon groups are preferred.

The number of carbon atoms in the alkyl group and the alkylene group is preferably in a range of 1 to 20 and more preferably in a range of 1 to 10.

The number of carbon atoms in the aryl group and the arylene group is preferably in a range of 6 to 18 and more preferably in a range of 6 to 12.

In General Formula (i), $X^1$ is preferably at least one of a sulfonic acid group, a carboxylic acid group, and an acid group having a phosphorous atom. The number of $X^1$s may be one or more and is preferably two or more.

In General Formula (i), n is preferably in a range of 1 to 3, more preferably 2 or 3, and still more preferably 3.

The molecular weight of the compound having two or more acid groups or a salt thereof is preferably 1000 or less, more preferably in a range of 70 to 1000, and still more preferably 70 to 500.

A preferred aspect of the compound having two or more acid groups is (1) an aspect in which the acid groups are selected from sulfonic acid groups, carboxylic acid groups, and acid groups having a phosphorous atom and more preferably (2) an aspect having sulfonic acid groups and carboxylic acid groups. In the above-described aspects, an infrared absorbing function is more effectively exhibited. Furthermore, when a compound having sulfonic acid groups and carboxylic acid groups is used, it is possible to further improve color valency.

(1) Specific examples of the compound in which the acid groups are selected from sulfonic acid groups, carboxylic acid groups, and acid groups having a phosphorous atom include the following compounds. In addition, the above-described sulfonic acid copper complexes A-131 to A-134 can also be preferred examples.

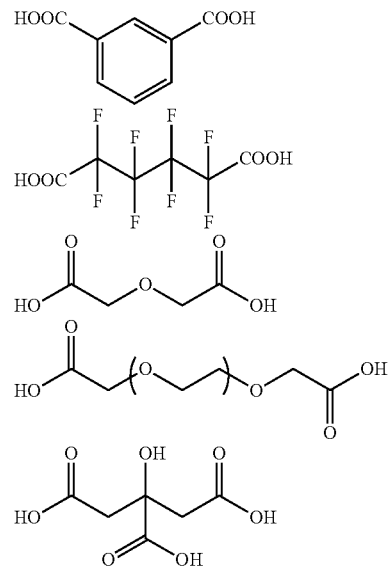

(2) Specific examples of the compound having sulfonic acid groups and carboxylic acid groups include the above-described sulfonic acid copper complexes A-133 and A-134 as preferred examples.

(Inorganic Fine Particles)

The composition of the present invention may include inorganic fine particles as a near-infrared-absorbing substance other than the above-described copper complex. Only one kind of inorganic fine particles may be used or two or more kinds of inorganic fine particles may be used.

The inorganic fine particles refer to particles that play a role of shielding (absorbing) infrared rays. The inorganic fine particles are preferably at least one selected from the group consisting of metal oxide particles and metal particles in terms of more favorable infrared shielding properties.

Examples of the inorganic fine particles include metal oxide particles such as indium tin oxide (ITO) particles, antimony tin oxide (ATO) particles, particles of zinc oxide which may be doped with aluminum (ZnO which may be doped with aluminum), fluorine-doped tin dioxide (F-doped $SnO_2$) particles, and niobium-doped titanium dioxide (Nb-doped $TiO_2$) and metal particles such as silver (Ag) particles, gold (Au) particles, copper (Cu) particles, and nickel (Ni) particles. Meanwhile, in order to satisfy both infrared shielding properties and photolithographic properties, inorganic fine particles having a high transmissivity at an exposure wavelength (365 nm to 405 nm) are desired and indium tin oxide (ITO) particles or antimony tin oxide (ATO) particles are preferred.

The shapes of the inorganic fine particles are not particularly limited, may be any of non-spherical and spherical, and may be sheet shapes, wire shapes, or tube shapes.

In addition, as the inorganic fine particles, a tungsten oxide-based compound can be used and, specifically, the inorganic fine particles are more preferably a tungsten oxide-based compound represented by General Formula (Composition Formula) (I) described below.

$$M_xW_yO_z \quad (I)$$

M represents metal, W represents tungsten, and O represents oxygen.

$$0.001 \leq x/y \leq 1.1$$

$$2.2 \leq z/y \leq 3.0$$

Examples of the metal M include alkali metals, alkali earth metals, Mg, Zr, Cr, Mn, Fe, Ru, Co, Rh, Ir, Ni, Pd, Pt, Cu, Ag, Au, Zn, Cd, Al, Ga, In, Tl, Sn, Pb, Ti, Nb, V, Mo, Ta, Re, Be, Hf, Os, and Bi. The metal M is preferably an alkali metal, more preferably Rb or Cs, and still more preferably Cs. The number of the metals M may be one or more.

When x/y is 0.001 or more, it is possible to sufficiently shield infrared rays and, when x/y is 1.1 or less, it is possible to more reliably avoid the generation of impurity phases in the tungsten oxide-based compound.

When z/y is 2.2 or more, it is possible to further improve chemical stability as a material and, when z/y is 3.0 or less, it is possible to sufficiently shield infrared rays.

The metal oxide is preferably cesium tungsten oxide.

Specific examples of the tungsten oxide-based compound represented by Formula (I) include $Cs_{0.33}WO_3$, $Rb_{0.33}WO_3$, $K_{0.33}WO_3$, $Ba_{0.33}WO_3$, and the like, $Cs_{0.33}WO_3$ or $Rb_{0.33}WO_3$ is preferred, and $Cs_{0.33}WO_3$ is more preferred.

The metal oxide preferably has a fine particle form. The average particle diameter of the metal oxide is preferably 800 nm or less, more preferably 400 nm or less, and still more preferably 200 nm or less. When the average particle diameter is in the above-described range, the metal oxide is not capable of easily shielding visible light through light scattering and thus it is possible to more reliably transmit light in the visible light range. From the viewpoint of avoiding light scattering, the average particle diameter is preferably small; however, in consideration of ease of handling during the manufacturing of the metal oxide, the average particle diameter of the metal oxide is generally 1 nm or more.

The tungsten oxide-based compound can be produced in a form of, for example, a dispersion of tungsten fine particles such as YMF-02 manufactured by Sumitomo Metal mining Co., Ltd.

The content of the metal oxide is preferably in a range of 0.01% by mass to 30% by mass, more preferably in a range of 0.1% by mass to 20% by mass, and still more preferably in a range of 1% by mass to 10% by mass in relation to the total solid content mass of the composition including the metal oxide.

<Solvent>

The composition of the present invention includes a solvent. The number of the solvents may be one or more and, in a case in which two or more solvents are used, the total amount thereof needs to be in the above-described range. In the composition of the present invention, the solid content of the near-infrared-absorbing composition is preferably in a range of 35% by mass to 90% by mass and more preferably in a range of 38% by mass to 80% by mass. That is, the fraction of the solvent in the composition of the present invention is preferably in a range of 10% by mass to 65% by mass, more preferably in a range of 20% by mass to 62% by mass, and particularly preferably in a range of 30% by mass to 60% by mass.

Regarding the solvent used in the present invention, there is no particular limitation and any solvent can be appropriately selected depending on the purpose as long as the solvent is capable of uniformly dissolving or dispersing the respective components of the composition of the present invention. Preferred examples thereof include water, organic solvents, alcohols, ketones, esters, aromatic hydrocarbons, halogenated hydrocarbons, dimethylformamide, dimethylacetoamide, dimethylsulfoxide, sulfolane, and the like. These solvents may be used singly or two or more solvents may be jointly used. In this case, a mixed solution made up of two or more solvents selected from 3-ethoxy methyl propionate, 3-ethoxy ethyl propionate, ethyl cellosolve acetate, ethyl lactate, diethylene glycol dimethyl ether, butyl lactate, 3-methoxy methyl propionate, 2-heptanone, cyclohexanone, ethyl carbitol acetate, butyl carbitol acetate, ethylene glycol monobutyl ether acetate, propylene glycol monomethyl ether, and propylene glycol monomethyl ether acetate is particularly preferred.

Specific examples of the alcohols, the aromatic hydrocarbons, and the halogenated hydrocarbons include those described in Paragraph <0136> and the like in JP2012-194534A and the content thereof is incorporated into the specification of the present application by reference. In addition, specific examples of the esters, the ketones, and the ethers include those described in Paragraph <0497> in JP2012-208494A (Paragraph <0609> in the corresponding US2012/0235099A) and further include n-amyl acetate, ethyl propionate, dimethyl phthalate, ethyl benzoate, methyl sulfate, acetone, methyl isobutyl ketone, diethyl ether, ethylene glycol monobutyl ether acetate, and the like.

<Curable Compound>

The composition of the present invention may further include a curable compound. However, in a case in which the copper complex is a curable compound having a polymerizable group, the composition does not necessarily include the curable compound. The curable compound may be a polymerizing compound or a non-polymerizing compound such as a binder. In addition, the curable compound may be a thermosetting compound or a photocrosslinkable compound and is preferably a thermosetting composition due to its high reaction rate.

<Compound Having Polymerizable Group>

The composition of the present invention preferably includes a compound having a polymerizable group (hereinafter, in some cases, referred to as the "polymerizing compound"). The above-described compound group is widely known in the corresponding industrial field and, in the present invention, the above-described compounds can be used without any particular limitation. The compounds may have any chemical form of, for example, a monomer, an oligomer, a prepolymer, a polymer, and the like.

The polymerizing compound may be monofunctional or polyfunctional and is preferably polyfunctional. The inclusion of the polyfunctional compound makes it possible to improve near-infrared shielding properties and heat resistance. The number of the functional groups is not particularly specified, but is preferably in a range of 2 to 8.

In a case in which the composition of the present invention includes the curable composition together with the sulfonic acid copper complex, a preferred aspect of the curable compound includes the following. The present invention is not limited to the following aspects.

(1) The curable compound included in the composition of the present invention is a (meth)acrylate.

(2) The curable compound included in the composition of the present invention is a polyfunctional (meth)acrylate.

(3) The curable compound included in the composition of the present invention is a tri- to hexafunctional (meth)acrylate.

(4) The curable compound included in the composition of the present invention is a polybasic acid-denatured (meth)acrylate.

(5) The curable compound included in the composition of the present invention is an epoxy resin.

(6) The curable compound included in the composition of the present invention is a polyfunctional epoxy resin.

<<A: Polymerizing Monomer and Polymerizing Oligomer>>

A first preferred embodiment of the composition of the present invention includes a monomer having a polymerizable group (polymerizing monomer) or an oligomer having a polymerizable group (polymerizing oligomer) (hereinafter, in some cases, the polymerizing monomer and the polymerizing oligomer will be collectively referred to as "the polymerizing monomer and the like") as the polymerizing compound.

Examples of the polymerizing monomer and the like include unsaturated carboxylic acids (for example, acrylic acid, methacrylic acid, itaconic acid, crotonic acid, isocrotonic acid, maleic acid, and the like), esters thereof, and amides thereof and esters of an unsaturated carboxylic acid and an aliphatic polyvalent alcohol compound and amides of an unsaturated carboxylic acid and an aliphatic polyvalent amine compound are preferred. In addition, addition reactants of an unsaturated carboxylic ester or amide having a nucleopetal substituent such as a hydroxyl group, an amino group, or a mercapto group and a monofunctional or polyfunctional isocyanate or epoxy, dehydration and condensation reactants of the unsaturated carboxylic ester or amide and a monofunctional or polyfunctional carboxylic acid, and the like are also preferably used. In addition, addition reactants of an unsaturated carboxyl ester or an amide having an electrophilic substituent such as an isocyanate group or an epoxy group and a monofunctional or polyfunctional alcohol, amine, or thiol and, furthermore, substitution reactants of an unsaturated carboxylic ester or amide having a desorbable substituent such as a halogen group or a tosyloxy group and a monofunctional or polyfunctional alcohol, amine, or thiol are also preferred.

As additional examples, it is also possible to use a compound group in which the above-described unsaturated carboxylic acid is substituted with an unsaturated phosphonic acid, a vinyl benzene derivative such as styrene, a vinyl ether, an aryl ether, or the like.

As the specific compounds thereof, the compounds described in Paragraphs <0095> to <0108> in JP2009-288705A can be preferably used even in the present invention.

In addition, the polymerizing monomer and the like are also preferably compounds having an ethylenic unsaturated group which has at least one addition-polymerizing ethylene group and a boiling point of 100° C. or higher at normal pressure and monofunctional (meth)acrylates, difunctional (meth)acrylates, and tri- or more-functional (meth)acrylates (for example, tri- to hexafunctional (meth)acrylate) are preferred.

Examples thereof include monofunctional acrylates or methacrylates such as polyethylene glycol mono(meth)acrylate, polypropylene glycol mono(meth)acrylate, and phenoxyethyl(meth)acrylate;

monomers and oligomers obtained by adding ethylene oxide or propylene oxide to a polyfunctional alcohol such as polyethylene glycol di(meth)acrylate, trimethylolethane tri(meth)acrylate, neopentyl glycol di(meth)acrylate, pentaerythritol tri(meth)acrylate, pentaerythritol tetra(meth)acrylate, dipentaerythritol penta(meth)acrylate, dipentaerythritol hexa(meth)acrylate, hexanediol(meth)acrylate, trimethylolpropane tri(acryloyloxypropyl)ether, tri(acryloyloxyethyl)isocyanurate, glycerin, or trimethylolethane and then (meth)acrylating the mixture;

polyfunctional acrylate or methacrylate such as urethane (meth)acrylates as respectively described in JP1973-41708B (JP-S48-41708B), and JP1975-6034B (JP-S50-6034B), JP1976-37193B (JP-S51-37193B), polyester acrylates respectively described in JP1973-64183B (JP-S48-64183B), JP1974-43191B (JP-S49-43191B), and JP1977-30490B (JP-S52-30490B), epoxy acrylates that are reaction products of an epoxy polymer and (meth)acrylic acid and mixtures thereof.

Among these, the polymerizing compound is preferably ethyleneoxy-denatured pentaerythritol tetraacrylate (NK ester ATM-35E as a commercially available product: manufactured by Shin-Nakamura Chemical Co., Ltd.), dipentaerythritol triacrylate (KAYARAD D-330 as a commercially available product; manufactured by Nippon Kayaku Co., Ltd.), dipentaerythritol tetraacrylate (KAYARAD D-320 as a commercially available product; manufactured by Nippon Kayaku Co., Ltd.), dipentaerythritol penta(meth)acrylate (KAYARAD D-310 as a commercially available product; manufactured by Nippon Kayaku Co., Ltd.), dipentaerythritol hexa(meth)acrylate (KAYARAD DPHA as a commercially available product; manufactured by Nippon Kayaku Co., Ltd.), and structures in which the above-described (meth)acryloyl groups are through ethylene glycol and propylene glycol residues. In addition, the oligomer types thereof can also be used.

Examples thereof include polyfunctional (meth)acrylates and the like obtained by reacting a polyfunctional carboxylic acid and a compound having a cyclic ether group such as glycidyl(meth)acrylate and an ethylenic unsaturated group.

In addition, as other preferred polymerizing monomers and the like, it is also possible to use compounds and curled polymers having a fluorene ring and a di- or more-functional ethylenic polymerizable group which are described in JP2010-160418A, JP2010-129825A, JP4364216B, and the like.

In addition, the compounds having a boiling point of 100° C. or higher at normal pressure and having at least one addition-polymerizing ethylenic unsaturated group are also preferably the compounds described in Paragraphs <0254> to <0257> in JP2008-292970A.

In addition, the compounds obtained by adding an ethylene oxide or propylene oxide to the polyfunctional alcohol, which are described as General Formulae (1) and (2) together with specific examples thereof in JP1998-62986A (JP-H10-62986A), can also be used as the polymerizing monomer.

Furthermore, the polymerizing monomer used in the present invention is preferably a polymerizing monomer represented by General Formulae (MO-1) to (MO-6).

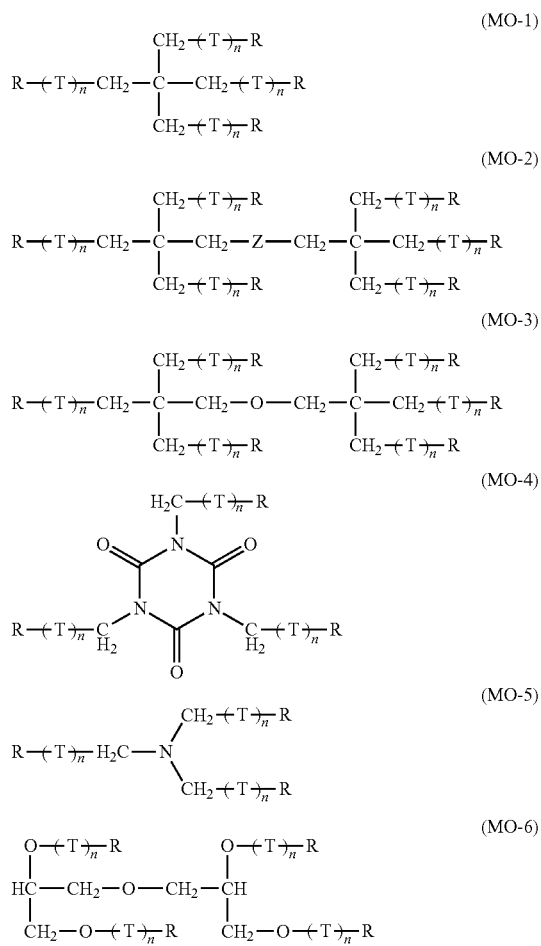

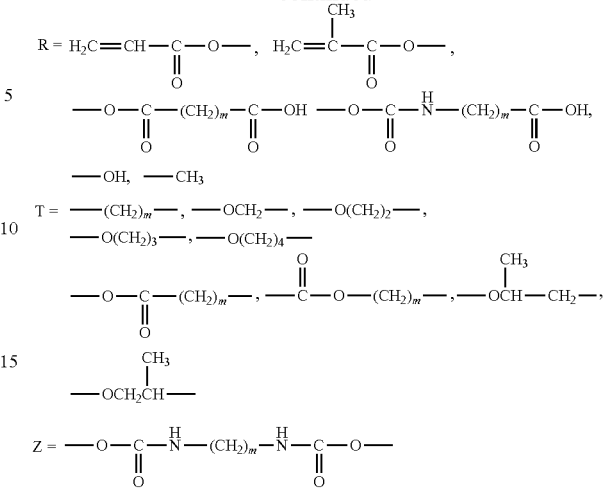

(In the formulae, ns are 0 to 14 respectively and ms are 1 to 8 respectively. The multiple R, T, and Z present in a molecule may be identical to or different from each other. In a case in which T is an oxyalkylene group, the terminal on the carbon atom side is bonded to R. At least one of the Rs is a polymerizable group.)

n is preferably 0 to 5 and more preferably 1 to 3.
m is preferably 1 to 5 and more preferably 1 to 3.
Rs are preferably groups represented by the following formulae.

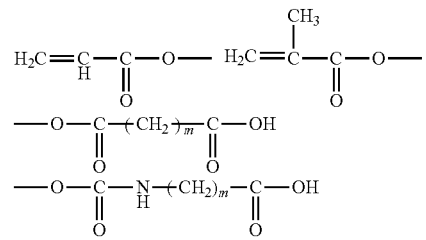

Particularly, Rs are more preferably groups represented by the following formulae.

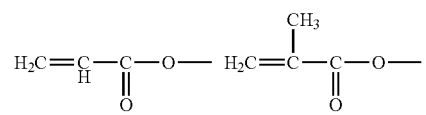

As specific examples of a radical polymerizing monomer represented by General Formulae (MO-1) to (MO-6), the compounds described in Paragraphs <0248> to <0251> in JP2007-269779A can also be preferably used in the present invention.

Among these, examples of the polymerizing monomer and the like include the polymerizing monomer and the like described in Paragraph <0477> in JP2012-208494A (Paragraph <0585> in the corresponding US2012/0235099A) and the content thereof is incorporated into the specification of the present application. In addition, diglycerin E0 (ethylene oxide)-denatured (meth)acrylate (M-460 as a commercially available product; manufactured by Toagosei Co., Ltd.) is preferred. Pentaerythritol tetraacrylate (manufactured by Shin-Nakamura Chemical Co., Ltd., A-TMMT) and 1,6-hexanediol diacrylate (manufactured by Nippon Kayaku Co., Ltd., KAYARAD HDDA) are also preferred. The oligomer types thereof can also be used.

Examples thereof include RP-1040 (manufactured by Nippon Kayaku Co., Ltd.).

The polymerizing monomer and the like are polyfunctional monomers and may have an acid group such as a carboxylic group, a sulfonic acid group, or a phosphorous acid group. Therefore, an ethylenic compound can be used as it is as long as the compound has an unreacted carboxylic group like a mixture-form compound as described above. If necessary, it is also possible to introduce an acid group by reacting a hydroxyl group into the above-described ethylenic compound and a non-aromatic carboxy anhydride. In this case, specific examples of the non-aromatic carboxy anhydride being used include anhydrous tetrahydrophthalic acid, alkylated anhydrous tetrahydrophthalic acid, anhydrous hexahydrophthalic acid, alkylated anhydrous hexahydrophthalic acid, anhydrous succinic acid, and anhydrous maleic acid.

In the present invention, the monomer having an acid group is preferably an ester of an aliphatic polyhydroxy compound and an unsaturated carboxylic acid which is a polyfunctional monomer provided with an acid group by reacting an unreacted hydroxyl group in an aromatic polyhydroxy compound and a non-aromatic carboxy anhydride and particularly preferably the ester in which the aliphatic polyhydroxy compound is pentaerythritol and/or dipentaerythritol. Examples of commercially available products thereof include ARONIX series M-305, M-510, M-520, and the like which are polybasic acid-denatured acryl oligomers manufactured by Toagosei Co., Ltd.

The acid value of the polyfunctional monomer having an acid group is preferably in a range of 0.1 mg-KOH/g to 40 mg-KOH/g and particularly preferably in a range of 5 mg-KOH/g to 30 mg-KOH/g. In a case in which two or more polyfunctional monomers having different acid groups are jointly used or polyfunctional monomers having no acid group are jointly used, it is necessary to adjust the polyfunctional monomer so that the acid value of the polyfunctional monomer falls in the above-described range as a whole.

In addition, the polymerizing monomer and the like preferably include a polyfunctional monomer having a caprolactam-denatured structure.

The polyfunctional monomer having a caprolactam-denatured structure is not particularly limited as long as the polyfunctional monomer has a caprolactam-denatured structure in the molecule. Examples of the polyfunctional monomer having a caprolactam-denatured structure include ∈-caprolactam-denatured polyfunctional (meth)acrylates obtained by esterifying a polyvalent alcohol such as trimethylol ethane, ditrimethylol ethane, trimethylol propane, ditrimethylol propane, pentaerythritol, dipentaerythritol, tripentaerythritol, glycerin, diglycerol, or trimethylol melamine, (meth)acrylic acid, and ∈-caprolactone. Among these, polyfunctional monomers having a caprolactam-denatured structure represented by Formula (1) described below are preferred.

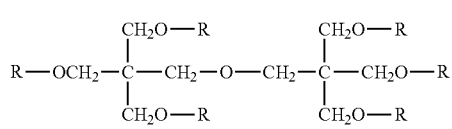

(In the formula, all of the six Rs are groups represented by Formula (2) described below or one to five of the six Rs are the groups represented by Formula (2) described below and the remaining Rs are groups represented by Formula (3) described below.)

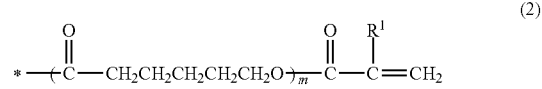

(In the formula, $R^1$ represents a hydrogen atom or a methyl group, m represents a number of 1 or 2, and "*" indicates a direct bond.)

(In the formula, $R^1$ represents a hydrogen atom or a methyl group and "*" indicates a direct bond.)

The above-described polyfunctional monomer having a caprolactam-denatured structure is commercially available under the name of, for example, KAYARAD DPCA series manufactured by Nippon Kayaku Co., Ltd. and examples thereof include DPCA-20 (compound in which m=1 in Formulae (1) to (3), the number of the groups represented by Formula (2)=2, and all the $R^1$s are hydrogen atoms), DPCA-30 (compound in which m=1 in the same formulae, the number of the groups represented by Formula (2)=3, and all the $R^1$s are hydrogen atoms), DPCA-60 (compound in which m=1 in the same formulae, the number of the groups represented by Formula (2)=6, and all the $R^1$s are hydrogen atoms), DPCA-120 (compound in which m=2 in the same formulae, the number of the groups represented by Formula (2)=6, and all the $R^1$s are hydrogen atoms), and the like.

In the present invention, the polyfunctional monomer having a caprolactam-denatured structure can be used singly or a mixture of two or more monomers can be used.

In addition, the polymerizing monomer and the like in the present invention are preferably at least one selected from the group of compounds represented by General Formula (i) or (ii).

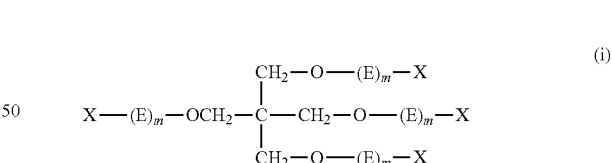

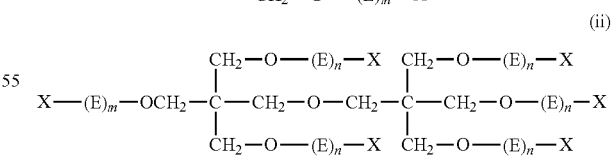

In General Formulae (i) and (ii), each of the Es independently represents $-((CH_2)_yCH_2O)-$ or $((CH_2)_yCH(CH_3)O)-$, each of the ys independently represents an integer from 0 to 10, and each of the Xs independently represents an acryloyl group, a methacryloyl group, a hydrogen atom, or a carboxyl group.

In General Formula (i), the total number of the acryloyl groups and the methacryloyl groups is 3 or 4, each of the ms independently represents an integer from 0 to 10, and the total number of the respective ms is an integer from 0 to 40. In a case in which the total number of the respective ms is 0, any one of the Xs is a carboxyl group.

In General Formula (ii), the total number of the acryloyl groups and the methacryloyl groups is 5 or 6, each of ns independently represents an integer from 0 to 10, and the total number of the respective ns is an integer from 0 to 60. In a case in which the total number of the respective ns is 0, any one of the Xs is a carboxyl group.

In General Formula (i), m is preferably an integer from 0 to 6 and more preferably an integer of 0 to 4. In addition, the total number of the respective ms is preferably an integer from 2 to 40, more preferably an integer from 2 to 16, and particularly preferably an integer from 4 to 8.

In General Formula (ii), n is preferably an integer from 0 to 6 and more preferably an integer of 0 to 4. In addition, the total number of the respective ns is preferably an integer from 3 to 60, more preferably an integer from 3 to 24, and particularly preferably an integer from 6 to 12.

In addition, —$((CH_2)_yCH_2O)$— or $((CH_2)_yCH(CH_3)O)$— in General Formulae (i) and (ii), the terminal on the oxygen atom side is preferably bonded to X.

The compound represented by General Formula (i) or (ii) may be used singly or two or more compounds may be jointly used. Particularly, in General Formula (ii), all of the six Xs are preferably acryloyl groups.

The compound represented by General Formula (i) or (ii) can be synthesized through a step of bonding a ring-opened skeleton using a ring-opening addition reaction between pentaerythritol or dipentaerythritol and ethylene oxide or propylene oxide, which is a well-known step in the related art, and a step of introducing a (meth)acryloyl group using a reaction between a terminal hydroxyl group in the ring-opened skeleton and, for example, (meth)acryloyl chloride. The respective steps are well-known steps and a person skilled in the art can easily synthesize the compound represented by General Formula (i) or (ii).

Among the compounds represented by General Formula (i) or (ii), pentaerythritol derivatives and/or dipentaerythritol derivatives are more preferred.

Specific examples thereof include compounds represented by Formulae (a) to (f) described below (hereinafter, referred to as "Exemplary Compounds (a) to (f)") and, among these, Exemplary Compounds (a), (b), (e), and (f) are preferred.

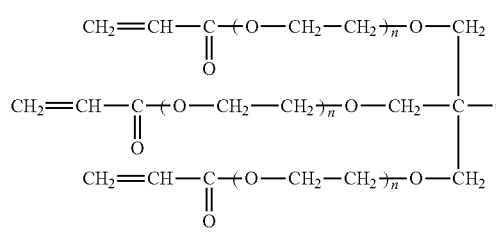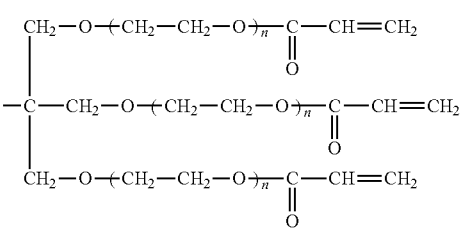

(a)

(Total of individual ns is 6)

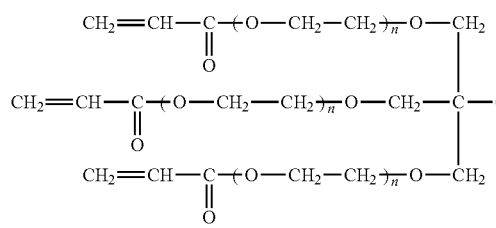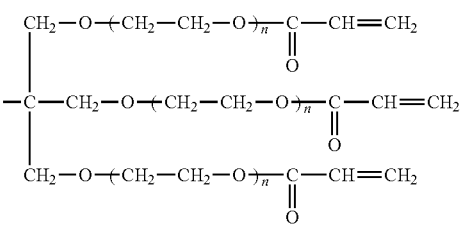

(b)

(Total of individual ns is 12)

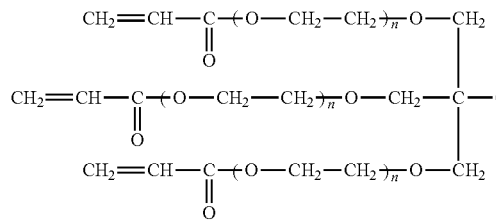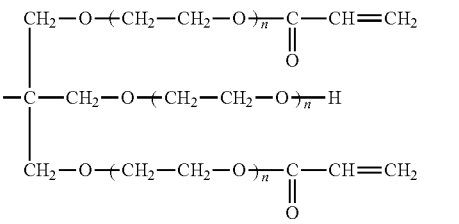

(c)

(Total of individual ns is 12)

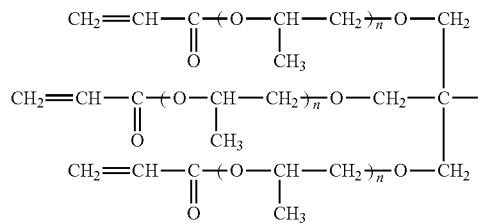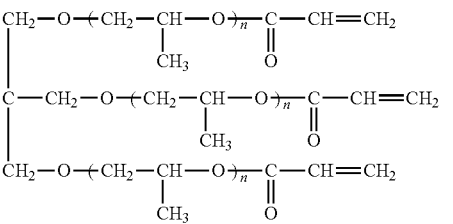

(d)

(Total of individual ns is 6)

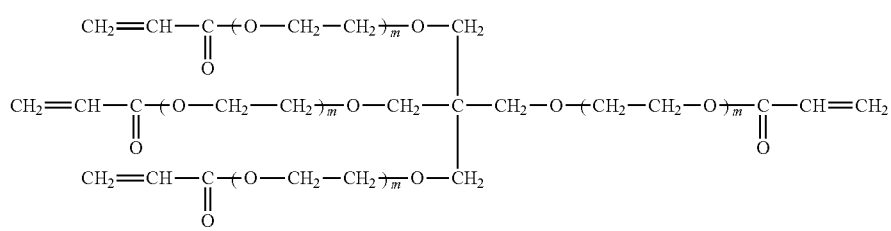
(e)

(Total of individual ms is 4)

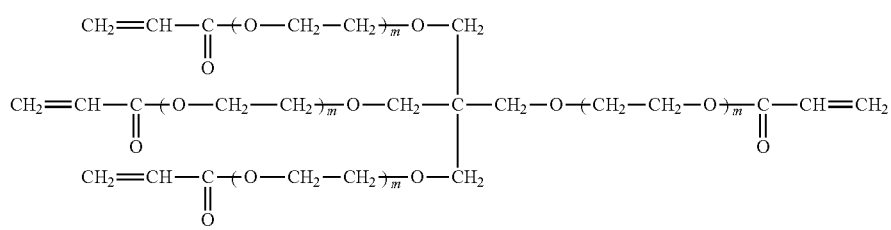
(f)

(Total of individual ms is 12)

Examples of the commercially available products of the polymerizing monomer and the like represented by General Formula (i) or (ii) include SR-494 manufactured by Sartomer Company, Inc. which is a tetrafunctional acrylate having four ethyleneoxy chains, DPCA-60 which is a hexafunctional acrylate having six pentyleneoxy chains, and TPA-330 which is a trifunctional acrylate having three isobutyleneoxy chains both of which are manufactured by Nippon Kayaku Co., Ltd.

In addition, the polymerizing monomer and the like are also preferably urethane acrylates as described in JP1973-41708B (JP-S48-41708B), JP1976-37193A (JP-S51-37193A), JP1990-32293B (JP-H2-32293B), and JP1990-16765B (JP-H2-16765B) and urethane compounds having an ethylene oxide-based skeleton described in JP1983-49860B (JP-S58-49860B), JP1981-17654B (JP-S56-17654B), JP1987-39417B (JP-S62-39417B), and JP1987-39418B (JP-S62-39418B). Furthermore, as the polymerizing monomer and the like, it is possible to obtain curable compositions having an extremely excellent photosensitive speed using an addition-polymerizing monomer having an amino structure or a sulfide structure in the molecule described in JP1988-277653A (JP-S63-277653A), JP1988-260909A (JP-S63-260909A), and JP1989-105238A (JP-H1-105238A).

Examples of the commercially available products of the polymerizing monomer and the like include urethane oligomers UAS-10, UAB-140 (manufactured by Sanyo-Kokusaku Pulp Co., Ltd.), UA-7200 (manufactured by Shin-Nakamura Chemical Co., Ltd.), DPHA-40H (manufactured by Nippon Kayaku Co., Ltd.), UA-306H, UA-306T, UA-306I, AH-600, T-600, AI-600 (manufactured by Kyoeisha Chemical Co., Ltd.), and the like.

The polymerizing monomer and the like are preferably polyfunctional thiol compounds having two or more mercapto (SH) groups in the same molecule. Particularly, polyfunctional thiol compounds represented by General Formula (I) described below are preferred.

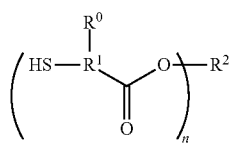
(I)

(In the formula, $R^1$ represents an alkyl group, $R^2$ represents an n-valent aliphatic group which may have an atom other than carbon, $R^0$ represents an alkyl group which is not hydrogen (H), and n represents 2 to 4.)

Specific examples of the polyfunctional thiol compounds represented by General Formula (I) include 1,4-bis(3-mercapto butyloxy)buthane having the following structural formula [Formula (II)], 1,3,5-tris(3-mercapto butyloxyethyl)-1,3,5-triazine-2,4,6(1H,3H,5H)-trione [Formula (III)], pentaerythtol tetrakis(3-mercaptobutylate) [Formula (IV)], and the like. The above-described polyfunctional thiols can be used singly or a combination of multiple polyfunctional thiols can be used.

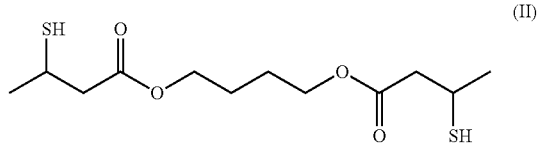
(II)

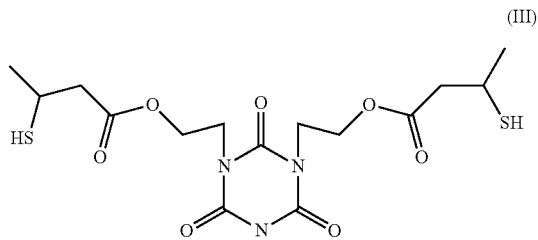
(III)

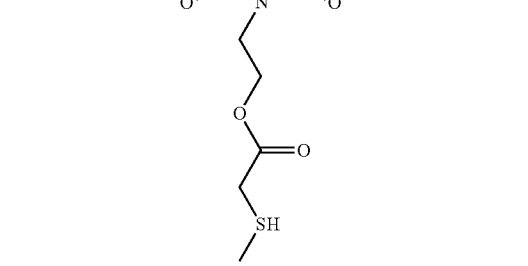

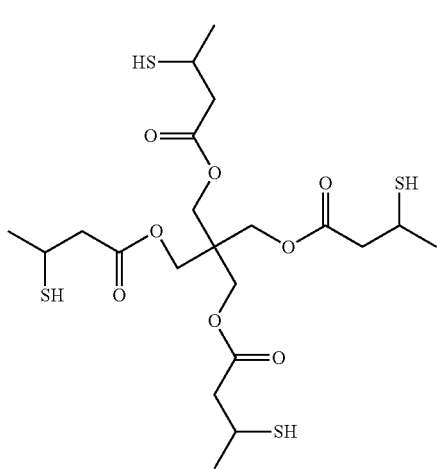

(IV)

In the present invention, as the polymerizing monomer and the like, a polymerizing monomer or oligomer having two or more epoxy groups or oxetanyl groups in the molecule is preferably used. Specific examples thereof are summarized in the section of compounds having an epoxy group or oxetanyl group described below.

<<B: Polymer Having Polymerizable Group at Side Chain>>

A second preferred aspect of the composition of the present invention includes a polymer having a polymerizable group at the side chain as the polymerizing compound.

Examples of the polymerizable group include an ethylenic unsaturated double bond group and an epoxy group or an oxetanyl group.

The polymer having the latter group will be collectively described in the section of a compound having an epoxy group or an oxetanyl group described below.

The polymer having an ethylenic unsaturated bond at the side chain is preferably a macromolecular compound having at least one selected from functional groups represented by any one of General Formulae (1) to (3) described below as the unsaturated double bond portion.

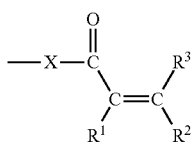

General Formula (1)

In General Formula (1), each of $R^1$ to $R^3$ independently represents a hydrogen atom or a monovalent organic group. Preferred examples of $R^1$ include a hydrogen atom, an alkyl group, and the like and, among these, a hydrogen atom and a methyl group are preferred due to their high radical reactivity. In addition, each of $R^2$ and $R^3$ independently represents a hydrogen atom, a halogen atom, an amino group, a carboxylic group, an alkoxycarbonyl group, a sulfo group, a nitro group, a cyano group, an alkyl group, an aryl group, an alkoxy group, an aryloxy group, an akylamino group, an arylamino group, an alkylsulfonyl group, an arylsulfonyl group, and the like and, among these, a hydrogen atom, a carboxylic group, an alkoxycarbonyl group, an alkyl group, and an aryl group are preferred due to their high radical reactivity.

X represents an oxygen atom, a sulfur atom, or —N($R^{12}$)— and $R^{12}$ represents a hydrogen atom or a monovalent organic group. Examples of $R^{12}$ include an alkyl group and the like and, among these, $R^{12}$ is preferably a hydrogen atom, a methyl group, an ethyl group, or an isopropyl group due to their high radical reactivity.

Here, examples of an introducible substituent include an alkyl group, an alkenyl group, an alkynyl group, an aryl group, an alkoxy group, an aryloxy group, a halogen atom, an amino group, an alkylamino group, an arylamino group, a carboxyl group, an alkoxy carbonyl group, a sulfo group, a nitro group, a cyano group, an amide group, an alkyl sulfonyl group, an aryl sulfonyl group, and the like.

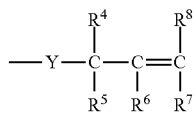

General Formula (2)

In General Formula (2), each of $R^4$ to $R^8$ independently represents a hydrogen atom or a monovalent organic group. Each of $R^4$ to $R^8$ is preferably a hydrogen atom, a halogen atom, an amino group, a dialkylamino group, a carboxyl group, an alkoxy carbonyl group, a sulfo group, a nitro group, a cyano group, an alkyl group, an aryl group, an alkoxy group, an aryloxy group, an alkylamino group, an arylamino group, an alkyl sulfonyl group, an aryl sulfonyl group, and the like and, among these, a hydrogen atom, a carboxyl group, an alkoxy carbonyl group, an alkyl group, and an aryl group are more preferred.

Examples of an introducible substituent include the same substituents as General Formula (1). In addition, Y represents an oxygen atom, a sulfur atom, or —N($R^{12}$)—. $R^{12}$ is identical to $R^{12}$ in General Formula (1) and the preferred range is also identical.

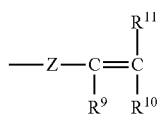

General Formula (3)

In General Formula (3), preferred examples of $R^9$ include a hydrogen atom, an alkyl group which may have a substituent, and the like and, among these, a hydrogen atom and a methyl group are preferred due to their high radical reactivity. Examples of each of $R^{10}$ and $R^{11}$ independently include a hydrogen atom, a halogen atom, an amino group, a dialkylamino group, a carboxyl group, an alkoxy carbonyl group, a sulfo group, a nitro group, a cyano group, an alkyl group, an aryl group, an alkoxy group, an aryloxy group, an alkylamino group, an arylamino group, an alkyl sulfonyl group, an aryl sulfonyl group, and the like and, among these, a hydrogen atom, a carboxyl group, an alkoxy carbonyl group, an alkyl group, and an aryl group are preferred due to their high radical reactivity.

Here, examples of an introducible substituent include the same substituents as General Formula (1). In addition, Z represents an oxygen atom, a sulfur atom, —N($R^{13}$)—, or a phenylene group. Examples of $R^{13}$ include an alkyl group and the like and, among these, a methyl group, an ethyl group, and an isopropyl group are preferred due to their high radical reactivity.

The polymer having an ethylenic unsaturated bond at the side chain in the present invention is preferably a compound having a configuration unit that includes a functional group represented by General Formulae (1) to (3) in a molecule in a range of 20 mol % to less than 95 mol %. The content of the configuration unit is more preferably in a range of 25 mol % to 90 mol % and still more preferably in a range of 30 mol % to less than 85 mol %.

A macromolecular compound having the configuration unit that includes the group represented by General Formulae (1) to (3) can be synthesized on the basis of the synthesis method described in Paragraphs <0027> to <0057> in JP2003-262958A. Among these, the macromolecular compound is preferably synthesized using the synthesis method 1) in the same publication.

The polymer having an ethylenic unsaturated bond used in the present invention may further include an acid group.

In the present specification, the acid group refers to an acid group having a dissociable group with a pKa of 14 or less, specific examples thereof include —COOH, —SO$_3$H, —PO$_3$H$_2$, —OSO$_3$H, —OPO$_2$H$_2$, -PhOH, —SO$_2$H, —SO$_2$NH$_2$, —SO$_2$NHCO—, —SO$_2$NHSO$_2$—, and the like, and among these, —COOH, —SO$_3$H, and —PO$_3$H$_2$ are preferred, and COOH is more preferred.

A polymer having the acid group and an ethylenic unsaturated bond at the side chain can be obtained by, for example, adding an ethylenic unsaturated group-containing epoxy compound to a carboxyl group in an alkali-soluble polymer having a carboxyl group.

Examples of the polymer having a carboxyl group include 1) polymers obtained by radical-polymerizing or ion-polymerizing monomers having a carboxyl group, 2) polymers obtained by radical or ion-polymerizing monomers having an acid anhydride and hydrolyzing or half-esterifying an acid anhydride unit, 3) epoxy acrylates obtained by denaturing an epoxy polymer using an unsaturated monocarboxylic acid and an acid anhydride, and the like.

Specific examples of a vinyl-based polymer having a carboxyl group include polymers obtained by singly polymerizing unsaturated carboxylic acids such as (meth)acrylic acid, 2-succinoyloxyethyl methacrylate, 2-maleinoyloxyethyl methacrylate, 2-phthaloyloxyethyl methacrylate, 2-hexahydrophthaloyloxyethyl methacrylate, maleic acid, fumaric acid, itaconic acid, or crotonic acid, which is a monomer having a carboxyl group, and polymers obtained by copolymerizing the above-described unsaturated carboxyl acid with a vinyl monomer having no carboxyl group such as styrene, α-methylstyrene, methyl(meth)acrylate, ethyl(meth)acrylate, propyl(meth)acrylate, isopropyl(meth)acrylate, butyl(meth)acrylate, vinyl acetate, acrylonitrile, (meth)acrylamide, glycidyl(meth)acrylate, allyl glycidyl ether, ethyl glycidyl acrylate, glycidyl crotonate ester, (meth)acrylic acid chloride, benzyl(meth)acrylate, hydroxyethyl(meth)acrylate, N-methylol acrylamide, N,N-dimethylacrylamide, N-methacryloylmopholine, N,N-dimethylaminoethyl(meth)acrylate, or N,N-dimethylaminoethylacrylamide.

In addition, examples thereof also include polymers obtained by copolymerizing anhydrous maleic acid and styrene, α-methyl styrene, or the like and half esterifying the anhydrous maleic acid unit portion with a monovalent alcohol such as methanol, ethanol, propanol, butanol, or hydroxyethyl(meth)acrylate or hydrolyzing the anhydrous maleic acid unit portion with water.

Among these, polymers having a carboxyl group, particularly, (meth)acrylic acid-(co)polymerized polymers including (meth)acrylate are preferred and specific examples of the copolymers include methyl methacrylate/methacrylic acid copolymers described in JP1985-208748A (JP-S60-208748A), methyl methacrylate/methyl acrylate/methacrylic acid copolymers described in JP1985-214354A (JP-S60-214354A), benzyl methacrylate/methyl methacrylate/methacrylic acid/2-ethylhexyl acrylate copolymers described in JP1993-36581A (JP-H5-36581A), methyl methacrylate/n-butyl methacrylate/2-ethylhexyl acrylate/methacrylic acid copolymers described in JP1993-333542A (JP-H5-333542A), styrene/methyl methacrylate/methyl acrylate/methacrylic acid copolymers described in JP1995-261407A (JP-H7-261407A), methyl methacrylate/n-butyl methacrylate/2-ethylhexyl methacrylate/methacrylic acid copolymers described in JP1998-110008A (JP-H10-110008A), methyl methacrylate/n-butyl methacrylate/2-ethylhexyl methacrylate/styrene/methacrylic acid copolymers described in JP1998-198031A (JP-H10-198031A), and the like.

A polymer including the acid group and the polymerizable group at the side chain in the present invention is preferably a macromolecular compound having at least one selected from configuration units represented by any one of General Formulae (1-1) to (3-1) described below as the unsaturated double bond portion.

General Formula (1-1)

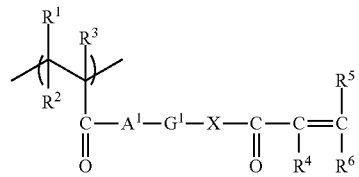

General Formula (2-1)

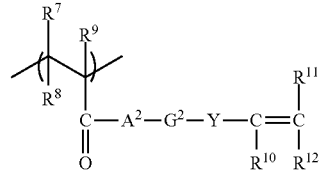

General Formula (3-1)

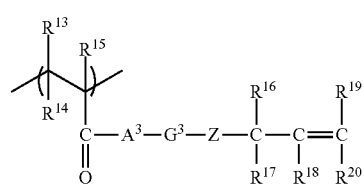

In General Formulae (1-1) to (3-1), each of $A^1$, $A^2$, and $A^3$ independently represents an oxygen atom, a sulfur atom, or —N($R^{21}$)— and $R^{21}$ represents an alkyl group. Each of $G^1$, $G^2$, and $G^3$ independently represents a divalent organic group. Each of X and Z independently represents an oxygen atom, a sulfur atom, or —N($R^{22}$)— and $R^{22}$ represents an alkyl group. Y represents an oxygen atom, a sulfur atom, a phenylene group, or —N($R^{23}$)— and $R^{23}$ represents an alkyl group. Each of $R^1$ to $R^{20}$ independently represents a monovalent substituent.

In General Formula (1-1), each of $R^1$ to $R^3$ independently represents a monovalent substituent. Examples of $R^1$ to $R^3$ include alkyl groups and the like which may further have a hydrogen atom and a substituent and, among these, $R^1$ and $R^2$ are preferably hydrogen atoms and $R^3$ is preferably a hydrogen atom or a methyl group.

Each of $R^4$ to $R^6$ independently represents a monovalent substituent. Examples of $R^4$ include alkyl groups and the like which may further have a hydrogen atom and a substituent and, among these, a hydrogen atom, a methyl group, and an ethyl group are preferred. Examples of each of $R^5$ and $R^6$ independently include a hydrogen atom, a halogen atom, an alkoxy carbonyl group, a sulfo group, a nitro group, a cyano group, an alkyl group which may further have a substituent, an aryl group which may further have a substituent, an alkoxy group which may further have a substituent, an aryloxy group which may further have a substituent, an alkyl sulfonyl group which may further have a substituent, an aryl sulfonyl group which may further have a substituent, and the like and, among these, a hydrogen atom, an alkoxy carbonyl group, an alkyl group which may further have a substituent, and an aryl group which may further have a substituent are preferred.

Here, examples of an introducible substituent include a methoxy carbonyl group, an ethoxy carbonyl group, anisopropioxy carbonyl group, a methyl group, an ethyl group, a phenyl group, and the like.

$A^1$ represents an oxygen atom, a sulfur atom, or —N($R^{21}$)— and X represents an oxygen atom, a sulfur atom, or —N($R^{22}$)—. Here, examples of $R^{21}$ and $R^{22}$ include an alkyl group.

$G^1$ represents a divalent organic group and is preferably an alkylene group. More preferred examples of $G^1$ include an alkylene group having 1 to 20 carbon atoms, a cycloalkylene group having 3 to 20 carbon atoms, an aromatic group having 6 to 20 carbon atoms, and the like and, among these, a linear or branched alkylene group having 1 to 10 carbon atoms, a cycloalkylene group having 3 to 10 carbon atoms, and an aromatic group having 6 to 12 carbon atoms are still more preferred in terms of performance such as strength and developing properties.

Here, the substituent in $G^1$ is preferably a hydroxyl group.

In General Formula (2-1), each of $R^7$ to $R^9$ independently represents a monovalent substituent. Examples of $R^7$ to $R^9$ include alkyl groups and the like which may further have a hydrogen atom and a substituent and, among these, $R^7$ and $R^8$ are preferably hydrogen atoms and $R^9$ is preferably a hydrogen atom or a methyl group.

Each of $R^{10}$ to $R^{12}$ independently represents a monovalent substituent. Specific examples of $R^{10}$ to $R^{12}$ include a hydrogen atom, a halogen atom, a dialkyl amino group, an alkoxy carbonyl group, a sulfo group, a nitro group, a cyano group, an alkyl group which may further have a substituent, an aryl group which may further have a substituent, an alkoxy group which may further have a substituent, an aryloxy group which may further have a substituent, an alkyl sulfonyl group which may further have a substituent, an aryl sulfonyl group which may further have a substituent, and the like and, among these, a hydrogen atom, an alkoxy carbonyl group, an alkyl group which may further have a substituent, and an aryl group which may further have a substituent are preferred.

Here, examples of an introducible substituent include the same substituents as represented by General Formula (1-1).

$A^2$ represents an oxygen atom, a sulfur atom, or —N($R^{21}$)— and, here, examples of $R^{21}$ include a hydrogen atom, an alkyl group, and the like.

$G^2$ represents a divalent organic group and is preferably an alkylene group. Preferred examples of $G^2$ include an alkylene group having 1 to 20 carbon atoms, a cycloalkylene group having 3 to 20 carbon atoms, an aromatic group having 6 o 20 carbon atoms, and the like and, among these, a linear or branched alkylene group having 1 to 10 carbon atoms, a cycloalkylene group having 3 to 10 carbon atoms, and an aromatic group having 6 to 12 carbon atoms are more preferred in terms of performance such as strength and developing properties.

Here, the substituent in $G^2$ is preferably a hydroxyl group.

Y represents an oxygen atom, a sulfur atom, —N($R^{23}$)—, or a phenylene group, and examples of $R^{23}$ include a hydrogen atom, an alkyl group, and the like.

In General Formula (3-1), each of $R^{13}$ to $R^{15}$ independently represents a monovalent substituent. Examples of $R^{13}$ to $R^{15}$ include a hydrogen atom, an alkyl group, and the like and, among these, $R^{13}$ and $R^{14}$ are preferably hydrogen atoms and $R^{15}$ is preferably a hydrogen atom or a methyl group.

Each of $R^{16}$ to $R^{20}$ independently represents a monovalent substituent. Examples of $R^{16}$ to $R^{20}$ include a hydrogen atom, a halogen atom, a dialkyl amino group, an alkoxy carbonyl group, a sulfo group, a nitro group, a cyano group, an alkyl group which may further have a substituent, an aryl group which may further have a substituent, an alkoxy group which may further have a substituent, an aryloxy group which may further have a substituent, an alkyl sulfonyl group which may further have a substituent, an aryl sulfonyl group which may further have a substituent, and the like and, among these, a hydrogen atom, an alkoxy carbonyl group, an alkyl group which may further have a substituent, and an aryl group which may further have a substituent are preferred. Examples of an introducible substituent include the same substituents as represented by General Formula (1).

$A^3$ represents an oxygen atom, a sulfur atom, or —N($R^{21}$)— and Z represents an oxygen atom, a sulfur atom, or —N($R^{22}$)—. Examples of $R^{21}$ and $R^{22}$ include the same alkyl groups as represented by General Formula (1).

$G^3$ represents a divalent organic group and is preferably an alkylene group. More preferred examples of $G^3$ include an alkylene group having 1 to 20 carbon atoms, a cycloalkylene group having 3 to 20 carbon atoms, an aromatic group having 6 to 20 carbon atoms, and the like and, among these, a linear or branched alkylene group having 1 to 10 carbon atoms, a cycloalkylene group having 3 to 10 carbon atoms, and an aromatic group having 6 to 12 carbon atoms are still more preferred in terms of performance such as strength and developing properties.

Here, the substituent in $G^3$ is preferably a hydroxyl group.

Regarding preferred examples of the configuration example having an ethylenic unsaturated bond and the acid group, the description of Paragraphs <0060> to <0063> and the like in JP2009-265518A can be referenced and the content thereof is incorporated into the specification of the present application by reference.

Preferably, the acid value of the polymer having the acid group and an ethylenic unsaturated bond at the side chain is in a range of 20 mg-KOH/g to 300 mg-KOH/g, preferably in a range of 40 mg-KOH/g to 200 mg-KOH/g, and more preferably in a range of 60 mg-KOH/g to 150 mg-KOH/g.

The polymer having a polymerizable group at the side chain used in the present invention is also preferably a polymer having an ethylenic unsaturated bond and a urethane group at the side chain (hereinafter, in some cases, referred to as the "urethane polymer").

The urethane polymer is a urethane polymer having a structural unit represented by a reaction product between at least one of the diisocyanate compounds represented by General Formula (4) described below and at least one of the diol compounds represented by General Formula (5) as a basic skeleton (hereinafter, in some cases, appropriately referred to as the "specific polyurethane polymer").

OCN—X⁰—NCO                       General Formula (4)

HO—Y⁰—OH                        General Formula (5)

In General Formulae (4) and (5), each of $X^0$ and $Y^0$ independently represents a divalent organic residue.

When at least any one of the diisocyanate compound represented by General Formula (4) and the diol compound represented by General Formula (5) has at least one of the groups represented by General Formulae (1) to (3) which illustrate the above-described unsaturated double bond portions, the specific polyurethane polymer in which the group represented by one of General Formulae (1) to (3) is introduced into the side chain is generated as a reaction product between the diisocyanate compound and the diol compound. According to the above-described method, it is also possible to easily produce the specific polyurethane polymer according to the present invention by substituting and introducing a desired side chain after the reaction and generation of the polyurethane polymer.

1) Diisocyanate Compound

Examples of the diisocyanate compound represented by General Formula (4) include products obtained through an addition reaction between a triisocyanate compound and 1 equivalent weight of a monofunctional alcohol or a monofunctional amine compound which has an unsaturated group.

Regarding the triisocyanate compound, for example, the compounds described in Paragraphs <0099> to <0105> and the like in JP2009-265518A can be referenced and the content thereof is incorporated into the specification of the present application by reference.

Here, a method for introducing the unsaturated group into the side chain of the polyurethane polymer is preferably a method in which a diisocyanate compound having an unsaturated group at the side chain is used as a raw material for producing the polyurethane polymer. Regarding the diisocyanate compound which can be obtained by an addition reaction between a triisocyanate compound and 1 equivalent weight of a monofunctional alcohol or monofunctional amine compound having an unsaturated group and has an unsaturated group at the side chain, for example, the compounds described in Paragraphs <0107> to <0114> in JP2009-265518A can be referenced and the content thereof is incorporated into the specification of the present application by reference.

As the specific polyurethane polymer used in the present invention, it is possible to copolymerize diisocyanate compounds other than the above-described diisocyanate compound having an unsaturated group from the viewpoint of, for example, improving compatibility with other components in the polymerizing composition and improving preservation stability.

Examples of the diisocyanate compounds being copolymerized include the following compounds. A preferred compound is a diisocyanate compound represented by General Formula (6) described below.

OCN-L¹-NCO                       General Formula (6)

In Formula (6), $L^1$ represents a divalent aliphatic or aromatic hydrocarbon group. If necessary, $L^1$ may include other functional groups that do not react with an isocyanate group, for example, an ester, urethane, an amide, or an ureido group.

Specific examples of the diisocyanate compound represented by General Formula (6) include compounds described below:

That is, examples thereof include aromatic diisocyanate compounds such as 2,4-tolylenediisocyante, dimers of 2,4-tolylenediisocyante, 2,6-tolylenediisocyanate, p-xylenediisocyante, m-xylenediisocyanate, 4,4'-diphenylmethanediisocyanate, 1,5-naphthylenediisocyanate, and 3,3-dimethylbiphenyl-4,4'-diisocyante;

aliphatic diisocyante compounds such as hexamethylene diisocyanate, trimethyl hexamethylenediisocyanate, lysine diisocyanate, and dimer acid diisocyanate; alicyclic diisocyanate compounds such as isophorone diisocyanate, 4,4'-methylene bis(cyclohexylisocyanate), methylcyclohexane-2,4(or 2,6)diisocyanate, and 1,3-(isocyanate methyl) cyclohexane; diisocyanate compounds which are reactants between a diol and diisocyante such as an adduct of 1 mol of 1,3-butylene glycol and 2 mol of tolylene diisocyanate; and the like.

2) Diol Compound

Examples of the diol compound represented by General Formula (5) broadly include polyether diol compounds, polyester diol compounds, polycarbonate diol compounds, and the like.

Here, a method for introducing the unsaturated group into the side chain of the polyurethane polymer is also preferably, in addition to the above-described method, a method in which a diol compound having an unsaturated group at the side chain is used as a raw material for producing the polyurethane polymer. The above-described diol compound may be, for example, a commercially available diol compound such as trimethylol propane monoallyl ether or may be a compound that is easily produced by reacting a halogenated diol compound, a triol compound, or an amino diol compound and carboxylic acid having an unsaturated group, an acid chloride, isocyanate, an alcohol, an amine, a thiol, or a halogenated alkyl compound. Regarding specific examples of the above-described compound, the compounds described in Paragraphs <0122> to <0125> and the like in JP2009-265518A can be referenced and the content thereof is incorporated into the specification of the present application by reference.

In addition, examples of a more preferred polymer in the present invention include polyurethane resins obtained using a diol compound represented by General Formula (G) as at least one of the diol compounds having an ethylenic unsaturated bond group when the polyurethane is synthesized.

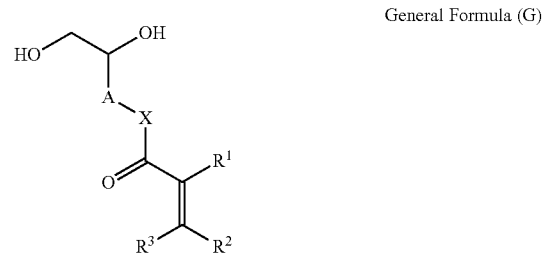

General Formula (G)

In General Formula (G), each of $R^1$ to $R^3$ independently represents a hydrogen atom or a monovalent organic group, A represents a divalent organic residue, X represents an oxygen atom, a sulfur atom, or —N($R^{12}$)—, and $R^{12}$ represents a hydrogen atom or a monovalent organic group.

Meanwhile, $R^1$ to $R^3$ and X in General Formula (G) are identical to $R^1$ to $R^3$ and X in General Formula (1) and the preferred range is also identical.

When the polyurethane polymer derived from the above-described diol compound is used, the excessive molecular movement of the polymer main chain caused by a secondary alcohol having a great steric hindrance is suppressed and thus it is considered that the above-described polyurethane polymer is capable of improving the film strength of layers.

Regarding specific examples of the diol compound represented by General Formula (G) which is preferably used for the synthesis of the specific polyurethane polymer, the compounds described in Paragraphs <0129> to <0131> and the like in JP2009-265518A can be referenced and the content thereof is incorporated into the specification of the present application by reference.

As the specific polyurethane polymer used in the present invention, it is possible to copolymerize diol compounds other than the above-described diol compound having an unsaturated group from the viewpoint of, for example, improving compatibility with other components in the polymerizing composition and improving preservation stability.

Examples of the above-described diol compounds include polyether diol compounds, polyester diol compounds, and polycarbonate diol compounds described above.

Examples of the polyether diol compounds include compounds represented by Formulae (7), (8), (9), (10), and (11) and random copolymers of an ethylene oxide having a hydroxyl group at the terminal and propylene oxide.

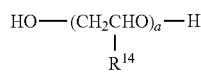  (7)

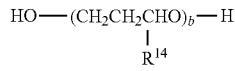  (8)

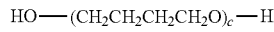  (9)

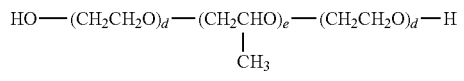  (10)

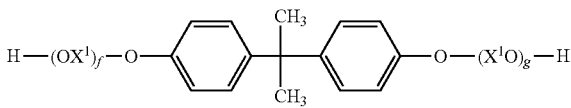  (11)

In Formulae (7) to (11), $R^{14}$ represents a hydrogen atom or a methyl group and $X^1$ represents the following group. In addition, each of a, b, c, d, e, f, and g represents an integer of 2 or more and each is preferably an integer from 2 to 100.

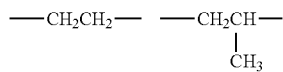

Regarding the polyether diol compounds represented by General Formulae (7) to (11), specifically, the compounds described in Paragraphs <0137> to <0140> and the like in JP2009-265518A can be referenced and the content thereof is incorporated into the specification of the present application by reference.

Specific examples of the random copolymers of an ethylene oxide having a hydroxyl group at the terminal and propylene oxide include the following copolymers.

That is, the examples are NEWPOL (trade name) 50HB-100, NEWPOL 50HB-260, NEWPOL 50HB-400, NEW-POL 50HB-660, NEWPOL 50HB-2000, NEWPOL 50HB-5100, which are manufactured by Sanyo Chemical Industries, Ltd., and the like.

Examples of the polyester diol compounds include compounds represented by Formulae (12) and (13).

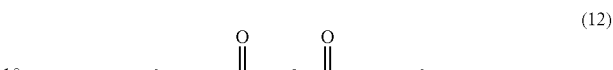  (12)

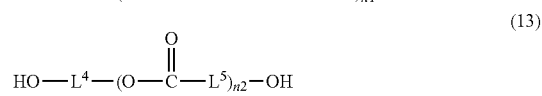  (13)

In Formulae (12) and (13), $L^2$, $L^3$, and $L^4$ may be identical to or different from each other and represent divalent aliphatic or aromatic hydrocarbon groups, and $L^5$ represents a divalent aliphatic hydrocarbon group. Preferably, each of $L^2$ to $L^4$ represents an alkylene group, an alkenyl group, an alkylene group, or an arylene group and $L^5$ represents an alkylene group. In addition, in $L^2$ to $L^5$, other functional groups that do not react with the isocyanate group, for example, ethers, carbonyl, esters, cyano, olefins, urethane, amides, ureido groups or halogen atoms may be present. Each of n1 and n2 is an integer of 2 or more and each is preferably an integer from 2 to 100.

The polycarbonate diol compound is a compound represented by Formula (14).

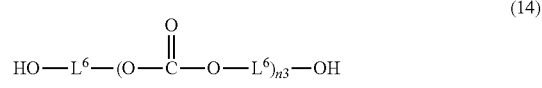  (14)

In Formula (14), $L^6$s may be identical to or different from each other and represent divalent aliphatic or aromatic hydrocarbon groups. Preferably, each of the $L^6$s represents an alkylene group, an alkenyl group, an alkylene group, or an arylene group. In addition, in $L^6$, other functional groups that do not react with the isocyanate group, for example, ethers, carbonyl, esters, cyano, olefins, urethane, amides, ureido groups or halogen atoms may be present. n3 is an integer of 2 or more and is preferably an integer from 2 to 100.

Regarding specific diol compounds represented by General Formula (12), (13), or (14), the compounds described in Paragraphs <0148> to <0150> and the like in JP2009-265518A can be referenced and the content thereof is incorporated into the specification of the present application by reference.

In addition, for the synthesis of the specific polyurethane polymer, it is also possible to jointly use a diol compound having a substituent that does not react with the isocyanate group in addition to the above-described diol compound. Examples of the above-described diol compound include compounds described below.

  (15)

  (16)

In Formulae (15) and (16), $L^7$ and $L^8$ may be identical to or different from each other and represent divalent aliphatic hydrocarbon groups, aromatic hydrocarbon groups, or heterocyclic groups which may have a substituent (for example, an alkyl group, an aralkyl group, an aryl group, an alkoxy group, an aryloxy group, or individual groups of halogen atoms such as —F, —Cl, —Br, and —I). If necessary, in $L^7$ and $L^8$, other functional groups that do not react with the isocyanate group, for example, a carbonyl group, an ester group, an urethane group, an amide group, and an ureido group may be present. Meanwhile, $L^7$ and $L^8$ may form a ring.

Furthermore, for the synthesis of the specific polyurethane polymer, it is also possible to jointly use a diol compound having a carboxyl group in addition to the diol compound.

Examples of the above-described diol compound include compounds represented by Formulae (17) to (19) described below.

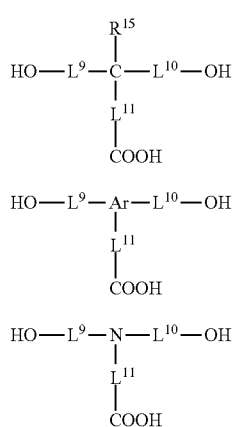

(17)

(18)

(19)

In Formulae (17) to (19), $R^{15}$ represents an alkyl group, an aralkyl group, an aryl group, an alkoxy group, or an aryloxy group which may have a substituent (for example, a cyano group, a nitro group, or individual groups of halogen atoms such as —F, —Cl, —Br, and —I, —CONH$_2$, —COOR$^{16}$, —OR$^{16}$, —NHCONHR$^{16}$, —NHCOOR$^{16}$, —NHCOR$^{16}$, —OCONHR$^{16}$ (here, $R^{16}$ represents an alkyl group having 1 to 10 carbon atoms or an aralkyl group having 7 to 15 carbon atoms)) and preferably represents a hydrogen atom, an alkyl group having 1 to 8 carbon atoms, or an aryl group having 6 to 15 carbon atoms. $L^9$, $L^{10}$, and $L^{11}$ may be identical to or different from each other. $L^9$, $L^{10}$, and $L^{11}$ represent single bonds or divalent aliphatic or aromatic hydrocarbon groups which may have a substituent (for example, individual groups such as alkyl groups, aralkyl groups, aryl groups, alkoxy groups, and halogen groups are preferred), preferably represent alkyl groups having 1 to 20 carbon atoms or arylene group having 6 to 15 carbon atoms, and more preferably represent alkylene groups having 1 to 8 carbon atoms. In addition, if necessary, in $L^9$ to $L^{11}$, other functional groups that do not react with the isocyanate group, for example, carbonyl, esters, urethane, amides, or ether groups may be present. Meanwhile, two or three out of $R^{15}$, $L^7$, $L^8$, and $L^9$ may form a ring.

Ar represents a trivalent aromatic hydrocarbon group and preferably represents an aromatic group having 6 to 15 carbon atoms.

Specific examples of the diol compound having a carboxyl group represented by Formulae (17) to (19) include the following compounds.

That is, the examples are 3,5-dihydroxy benzoate, 2,2-bis(hydroxymethyl)propionate, 2,2-bis(2-hydroxyethyl)propionate, 2,2-bis(3-hydroxypropyl)propionate, bis(hydroxymethyl)acetate, bis(4-hydroxyphenyl)acetate, 2,2-bis(hydroxymethyl)acetate, 4,4-bis(4-hydroxyphenyl)pentanoate, tartaric acid, N,N-dihydroxyethyl glycine, N,N-bis(2-hydroxyethyl)-3-carboxy-propionamide, and the like.

The presence of the above-described carboxyl group is capable of imparting characteristics such as hydrogen-bonding properties and alkali-soluble properties to the polyurethane polymer and is thus preferred. More specifically, the polyurethane polymer having an ethylenic unsaturated bond at the side chain further has a carboxyl group at the side chain and, more specifically, the polyurethane polymer having 0.3 meq/g or more of an ethylenic unsaturated bond group at the side chain and having 0.4 meq/g or more of a carboxyl group at the side chain is particularly preferably used as a binder polymer of the present invention.

In addition, for the synthesis of the specific polyurethane polymer, it is also possible to jointly use a compound in which a tetracarboxylic dianhydride represented by Formulae (20) to (22) described below is ring-opened using a diol compound in addition to the diol compound.

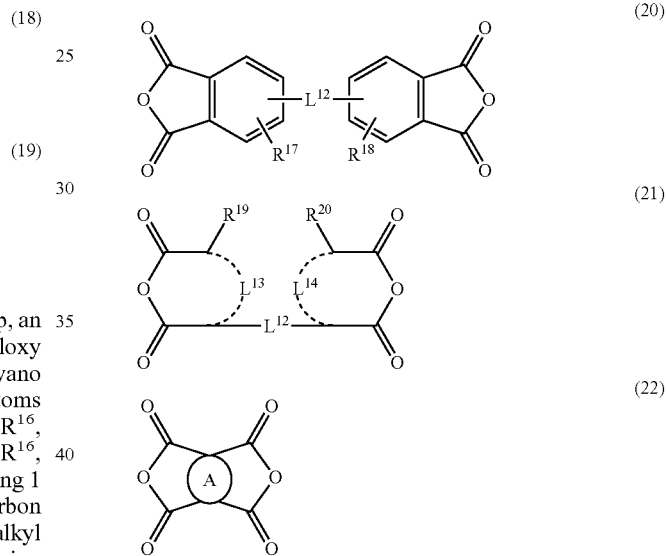

(20)

(21)

(22)

In Formulae (20) to (22), $L^{12}$ represent a single bonds, a divalent aliphatic or aromatic hydrocarbon group which may have a substituent (for example, alkyl groups, aralkyl groups, aryl groups, alkoxy groups, and individual groups of halogens, esters, and amides are preferred), —CO—, —SO—, —SO$_2$—, —O—, or S— and preferably represent a single bonds, a divalent aliphatic hydrocarbon group having 1 to 15 carbon atoms, —CO—, —SO$_2$—, —O—, or S—. $L^{17}$ and $L^{18}$ may be identical to or different from each other and represent hydrogen atoms, alkyl groups, aralkyl groups, aryl groups, alkoxy groups, or halogen groups and preferably represent hydrogen atoms, alkyl groups having 1 to 8 carbon atoms, aryl groups having 6 to 15 carbon atoms, alkoxy groups having 1 to 8 carbon atoms, or halogen groups. In addition, two out of $L^{12}$, $R^{17}$, and $R^{18}$ may be bonded to each other so as to form a ring.

$R^{19}$ and $R^{20}$ may be identical to or different from each other and represent hydrogen atoms, alkyl groups, aralkyl groups, aryl groups, or halogen groups and preferably represents hydrogen atoms, alkyl groups having 1 to 8 carbon atoms, or aryl groups having 6 to 15 carbon atoms. In addition, two out of $L^{12}$, $R^{19}$, and $R^{20}$ may be bonded to each other so as to form a ring. $L^{13}$ and $L^{14}$ may be identical to or different from each other, represent single bonds, double bonds, or divalent aliphatic hydrocarbon groups, and preferably represent single bonds, double bonds, or methylene groups. A represents a mononuclear or polynuclear aromatic ring and preferably represents an aromatic ring having 6 to 18 carbon atoms.

Regarding compounds represented by General Formula (20), (21), or (22), specifically, the description of Paragraphs <0163> and <0164> and the like in JP2009-265518A can be referenced and the content thereof is incorporated into the specification of the present application by reference.

Regarding a method for introducing a compound in which the above-described tetracarboxylic dianhydride is ring-opened using a diol compound into the polyurethane polymer, examples thereof include the following methods.

a) A method in which a compound at the alcohol terminal obtained by ring-opening tetracarboxylic dianhydride using a diol compound and a diisocyanate compound are reacted together.

b) A method in which a urethane compound at the alcohol terminal obtained by reacting diisocyanate compounds under conditions of an excessive amount of a diol compound and are tetracarboxylic dianhydride reacted together.

In addition, regarding the diol compound used in the ring-opening reaction at this time, specifically, the description of Paragraphs <0166> and the like in JP2009-265518A can be referenced and the content thereof is incorporated into the specification of the present application by reference.

The specific polyurethane polymer that can be used in the present invention is synthesized by heating the diisocyanate compound and the diol compound in a non-protonic solvent after the addition of a well-known catalyst having activity in accordance with the reactivity of the components. The molar ratio ($M_a$:$M_b$) between the diisocyanate compound and the diol compound used in the synthesis is preferably in a range of 1:1 to 1.2:1 and, when the diisocyanate compound and the diol compound used in the synthesis are treated using an alcohol, an amine, or the like, a product having desired properties such as molecular weight or viscosity is synthesized in a form in which an isocyanate group does not remain in the end.

Regarding the introduced amount of the ethylenic unsaturated bond included in the specific polyurethane polymer according to the present invention, the amount of the ethylenic unsaturated bond group included at the side chain is preferably 0.3 meq/g or more and more preferably in a range of 0.35 meq/g to 1.50 meq/g in terms of equivalent weight.

The molecular weight of the specific polyurethane polymer according to the present invention is preferably 10,000 or more and more preferably in a range of 40,000 to 200,000 in terms of weight-average molecular weight.

In the present invention, a styrene-based polymer having an ethylenic unsaturated bond at the side chain (hereinafter, in some cases, referred to as "styrene-based polymer") is also preferred and a styrene-based polymer having at least one of the styrenic double bonds represented by General Formula (23) (styrene and cc methyl styrene-based double bond) and vinylpyridinium groups represented by General Formula (24) is more preferred.

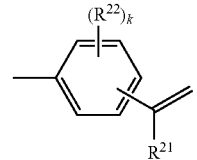

General Formula (23)

In General Formula (23), $R^{21}$ represents a hydrogen atom or a methyl group. $R^{22}$ represents an arbitrary substitutable atom or atomic group. k represents an integer from 0 to 4.

Meanwhile, the styrenic double bond represented by General Formula (23) is linked to the polymer main chain through a single bond or a linking group made of an arbitrary atom or atomic group and there is no particular limitation regarding the manner of bonding.

Regarding preferred examples of the repeating unit of a macromolecular compound having a functional group represented by General Formula (23), the description of Paragraphs <0179> to <0181> and the like in JP2009-265518A can be referenced and the content thereof is incorporated into the specification of the present application by reference.

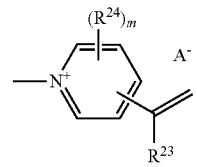

General Formula (24)

In General Formula (24), $R^{23}$ represents a hydrogen atom or a methyl group. $R^{24}$ represents an arbitrary substitutable atom or atomic group. m represents an integer from 0 to 4. $A^-$ represents an anion. In addition, a pyridinium ring may have a benzopyridium form in which a benzene ring is condensed as a substituent and, in this case, the pyridinium ring has a quinolinium group and an isoquinolium group.

Meanwhile, the vinylpyridinium group represented by General Formula (24) is linked to the polymer main chain through a single bond or a linking group made of an arbitrary atom or atomic group and there is no particular limitation regarding the manner of bonding.

Regarding preferred examples of the repeating unit of a macromolecular compound having a functional group represented by General Formula (24), the description of Paragraphs <0184> and the like in JP2009-265518A can be referenced and the content thereof is incorporated into the specification of the present application by reference.

As a method for synthesizing the styrene-based polymer, there is a method in which monomers which have a functional group represented by General Formula (23) or (24) and have a functional group capable of copolymerizing other copolymerization components are copolymerized using a well-known copolymerization method. Here, the styrene-based polymer may be a homopolymer having only one kind of any one of the functional groups represented by General Formulae (23) and (24) or a copolymer having two or more kinds of either or both functional groups.

Furthermore, the styrene-based polymer may also be a copolymer with another copolymerization monomer that does not include the above-described functional group. In this case, for example, for the purpose of making the polymer soluble in an alkali aqueous solution, a carboxyl group-containing monomer is preferably selected as the copolymerization monomer and examples thereof include acrylic acid, methacrylic acid, 2-carboxyethyl acrylate ester, 2-carboxyethyl methacrylate ester, crotonic acid, maleic acid, fumaric acid, monoalkyl maleate ester, monoalkyl fumarate ester, 4-carboxystyrene, and the like.

It is also possible to preferably synthesize and use a (multicomponent) copolymer by introducing a monomer component other than the monomer having a carboxyl group into the copolymer. Regarding monomers that can be incorporated into the copolymer in this case, the description of Paragraphs <0187> and the like in JP2009-265518A can be referenced and the content thereof is incorporated into the specification of the present application by reference.

In a case in which the above-described copolymer is used as the styrene-based polymer, the fraction of the repeating unit having the functional group represented by General Formula (23) and/or General Formula (24) in the total copolymer composition is preferably 20% by mass or more and more preferably 40% by mass or more. In the above-described range, the effects of the present invention are excellent and a high-sensitivity crosslinked system is imparted.

The molecular weight of the styrene-based polymer is preferably in a range of 10000 to 300000, more preferably in a range of 15000 to 200000, and most preferably in a range of 20000 to 150000 in terms of weight-average molecular weight.

Regarding additional examples of the polymer having an ethylenic unsaturated bond at the side chain is as follows. Examples of a novolac polymer having an ethylenic unsaturated group at the side chain include the polymers described in JP1997-269596A (JP-H9-269596A), polymers in which an ethylenic unsaturated bond is introduced into the side chain using the method described in JP2002-62648A, and the like.

In addition, examples of an acetal polymer having an ethylenic unsaturated bond at the side chain include the polymers described in JP2002-162741A and the like.

Furthermore, examples of a polyamide-based polymer having an ethylenic unsaturated bond at the side chain include the polymers described in JP2003-321022, polymers in which an ethylenic unsaturated bond is introduced into the side chain of a polyamide polymer cited in the above-described polymers using the method described in JP2002-62648A, and the like.

Examples of a polyimide polymer having an ethylenic unsaturated bond at the side chain include the polymers described in JP2003-339785A, polymers in which an ethylenic unsaturated bond is introduced into the side chain of a polyimide polymer cited in the above-described polymers using the method described in JP2002-62648A, and the like.

<<C: Compound Having Epoxy Group or Oxetanyl Group>>

A third preferred aspect of the present invention includes a compound having an epoxy group or an oxetanyl group as the polymerizing compound. Examples of the compound having an epoxy group or an oxetanyl group include polymers having an epoxy group at the side chain and polymerizing monomers or oligomers having two or more epoxy groups in the molecule and specific examples thereof include bisphenol A-type epoxy resins, bisphenol F-type epoxy resins, phenol novolac-type epoxy resins, cresol novolac-type epoxy resins, aromatic epoxy resins, and the like. A monofunctional or polyfunctional glycidyl ether compound can also be used as the compound having an epoxy group or an oxetanyl group and a polyfunctional aliphatic glycidyl ether compound is preferred.

As the above-described compound, a commercially available product may be used or the compound can be obtained by introducing an epoxy group into the side chain in the polymer.

In addition, regarding the commercially available product, for example, the description of Paragraphs <0191> and the like in JP2012-155288A can be referenced and the content thereof is incorporated into the specification of the present application by reference.

Examples of the commercially available product include polyfunctional aliphatic glycidyl ether compounds such as DENACOL EX-212L, EX-214L, EX-216L, EX-321L, and EX-850L (all manufactured by Nagase ChemteX Corporation). The above-described products are low-chlorine products and EX-212, EX-214, EX-216, EX-321, EX-850, and the like, which are not low-chlorine products, can also be used in a similar manner.

Additionally, examples thereof include ADEKA RESIN EP-40005, ADEKA RESIN EP-40035, ADEKA RESIN EP-40105, ADEKA RESIN EP-40115 (all manufactured by Adeka Corporation), NC-2000, NC-3000, NC-7300, XD-1000, EPPN-501, EPPN-502 (all manufactured by Adeka Corporation), JER1031S, and the like.

Furthermore, examples of the commercially available product of the phenol novolac-type epoxy resins include JER-157565, JER-152, JER-154, JER-157570 (all manufactured by Mitsubishi Chemical Corporation), and the like.

As a specific example of a polymer having an oxetanyl group at the side chain and the above-described polymerizing monomer or oligomer having two or more oxetanyl groups in the molecule, it is possible to use ARON OXETANE OXT-121, OXT-221, OX-SQ, and PNOX (all manufactured by Toagosei Co., Ltd.).

In a case in which the compound is synthesized by introducing an epoxy group into the side chain in the polymer, the introduction reaction can be carried out by causing a reaction in an organic solvent at a reaction temperature in a range of 50° C. to 150° C. for several hours to several tens of hours using, for example, a ternary amine such as trimethylamine or benzylmethylamine, a quaternary ammonium salt such as dodecyl trimethyl ammonium chloride, tetramethyl ammonium chloride, or tetraethyl ammonium chloride, pyridine, or triphenylphosphine as a catalyst. The introduced amount of an alicyclic epoxy unsaturated compound is preferably controlled so that the acid value of the obtained polymer falls in a range of 5 KOH·mg/g to 200 KOH·mg/g. In addition, the molecular weight is in a range of 500 to 5000000 and, furthermore, preferably in a range of 1000 to 500000 in terms of weight average.

As the epoxy unsaturated compound, it is also possible to use a compound having a glycidyl group as an epoxy group such as glycidyl(meth)acrylate or allyl glycidyl ether and the epoxy unsaturated compound is preferably an unsaturated compound having an alicyclic epoxy group. Regarding the above-described unsaturated compound, the description of Paragraphs <0045> and the like in JP2009-265518A and the like can be referenced and the content thereof is incorporated into the specification of the present application by reference.

The present invention preferably includes a polymer having a crosslinked group such as an unsaturated double bond, an epoxy group, or an oxetanyl group. Therefore, it is possible to further improve film-forming properties (the suppression of cracking or warping) and humidity resistance when a cured film is produced. Specific examples thereof include polymers having a repeating unit described below. The polymer having the following repeating unit is preferably a polymer having an epoxy group.

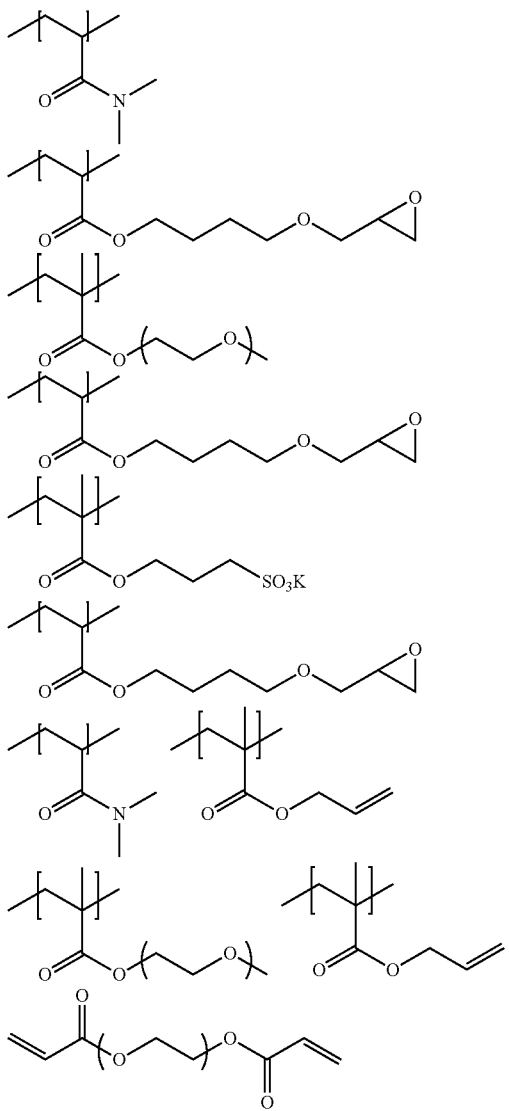

<<Compound Having Partial Structure Represented by Formula (1)>>

The curable compound used in the present invention also preferably has a partial structure represented by Formula (1) and the curable compound may have a crosslinked group such as an unsaturated double bond, an epoxy group, or an oxetanyl group.

General Formula (1)

(In Formula (1), $R^1$ represents a hydrogen atom or an organic group.)

When the above-described compound is included, it is possible to further improve near-infrared shielding properties and further improve moisture resistance when a cured film is produced using the near-infrared-absorbing composition of the present invention.

In Formula (1), $R^1$ represents a hydrogen atom or an organic group. Examples of the organic group include hydrocarbon groups, specifically, alkyl groups and aryl groups and the organic group is preferably an alkyl group having 1 to 20 carbon atoms, an aryl group having 6 to 20 carbon atoms, or a group obtained by combining the above-described group and a divalent linking group.

Specific examples of the above-described organic group include —OR', —SR', and groups obtained by combining the above-described group and at least one of —(CH$_2$)$_m$— (m is an integer from 1 to 10), a cyclic alkylene group having 5 to 10 carbon atoms, —O—, —CO—, —COO—, and —NH—. Here, R' is preferably a hydrogen atom, a linear alkyl group having 1 to 10 carbon atoms, a branched or cyclic alkyl group having 3 to 10 carbon atoms (preferably a linear alkyl group having 1 to 7 carbon atoms or a branched or cyclic alkyl group having 3 to 7 carbon atoms), an aryl group having 6 to 10 carbon atoms, or a group obtained by combining an aryl group having 6 to 10 carbon atoms and an alkylene group having 1 to 10 carbon atoms.

In addition, in Formula (1), $R^1$ and C may be bonded together and thus form a ring structure (heterocyclic structure). A hetero atom in the heterocyclic structure is a nitrogen atom in Formula (1). The heterocyclic structure is preferably a 5- or 6-membered ring structure and more preferably a 5-membered ring structure. The heterocyclic structure may be a condensed ring, but is preferably a single ring.

Specific examples of particularly preferred $R^1$ include a hydrogen atom, an alkyl group having 1 to 3 carbon atoms, groups obtained by combining —OR' (R' is a liner alkyl group having 1 to 5 carbon atoms) and —(CH$_2$)$_m$— (m is an integer from 1 to 10 and preferably an integer from 1 to 5), and groups in which $R^1$ and C in Formula (1) are bonded together and thus form a heterocyclic structure (preferably a 5-membered ring structure).

The compound having the partial structure represented by Formula (1) is preferably represented by (the main chain structure of the polymer-the partial structure (1)-$R^1$) or (A—the partial structure (1)-B). Here, A is a linear alkyl group having 1 to 10 carbon atoms, a branched alkyl group having 3 to 10 carbon atoms, or a cyclic alkyl group having 3 to 10 carbon atoms. In addition, B is a group obtained by combining —(CH$_2$)$_m$— (m is an integer from 1 to 10 and preferably an integer from 1 to 5), the partial structure (1), and a polymerizable group.

In addition, the compound having the partial structure represented by Formula (1) preferably has a structure represented by any one of Formulae (1-1) to (1-5) described below.

General Formula (1-1)

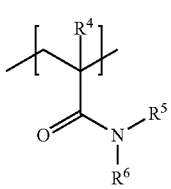

General Formula (1-2)

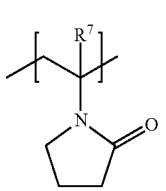

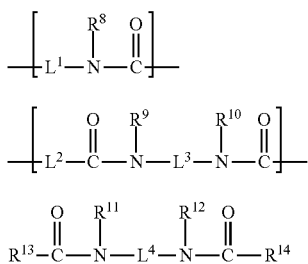

General Formula (1-3)

General Formula (1-4)

General Formula (1-5)

(In Formula (1-1), $R^4$ represents a hydrogen atom or a methyl group and each of $R^5$ and $R^6$ independently represents a hydrogen atom or an organic group. In Formula (1-2), $R^7$ represents a hydrogen atom or a methyl group. In Formula (1-3), $L^1$ represents a divalent linking group and $R^8$ represents a hydrogen atom or an organic group. In Formula (1-4), each of $L^2$ and $L^3$ independently represents a divalent linking group and each of $R^9$ and $R^{10}$ independently represents a hydrogen atom or an organic group. In Formula (1-5), $L^4$ represents a divalent linking group and each of $R^{11}$ to $R^{14}$ independently represents a hydrogen atom or an organic group.)

In Formula (1-1), each of $R^5$ and $R^6$ independently represents a hydrogen atom or an organic group. The organic group is identical to $R^1$ in Formula (1) and the preferred range thereof is also identical.

In Formulae (1-3) to (1-5), $L^1$ to $L^4$ represent divalent linking groups. The divalent linking group is preferably a divalent linking group obtained through a combination with at least one of —(CH$_2$)$_m$— (m is an integer from 1 to 10), a cyclic alkylene group having 5 to 10 carbon atoms, —O—, —CO—, —COO—, and —NH— and more preferably —(CH$_2$)$_m$— (m is an integer from 1 to 8).

In Formulae (1-3) to (1-5), each of $R^8$ to $R^{14}$ independently represents a hydrogen atom or an organic group. The organic group is preferably a hydrocarbon group, specifically, an alkyl group or an alkenyl group.

The alkyl group may be substituted. In addition, the alkyl group may have a linear shape, a branched shape, or a ring shape, but preferably has a linear shape or a ring shape. The alkyl group is preferably an alkyl group having 1 to 10 carbon atoms, more preferably an alkyl group having 1 to 8 carbon atoms, and still more preferably an alkyl group having 1 to 6 carbon atoms.

The alkenyl group may be substituted. The alkenyl group is preferably an alkenyl group having 1 to 10 carbon atoms, more preferably an alkenyl group having 1 to 4 carbon atoms, and particularly preferably a vinyl group.

Examples of the substituent include a polymerizable group, a halogen atom, an alkyl group, a carboxylic ester group, a halogenated alkyl group, an alkoxy group, a methacryloyloxy group, an acryloyloxy group, an ether group, a sulfonyl group, a sulfide group, an amide group, an acyl group, a hydroxyl group, a carboxyl group, or the like. Among the above-described substituents, a polymerizable group (for example, a vinyl group, a (meth)acryloyloxy group, a (meth)acryloyl group, an epoxy group, an aziridinyl group, or the like) is preferred and a vinyl group is more preferred.

In addition, the compound having the partial structure represented by Formula (1) may be a monomer or a polymer, but is preferably a polymer. The compound having the partial structure represented by Formula (1) is preferably a compound represented by Formula (1-1) or (1-2).

In addition, in a case in which the compound having the partial structure represented by Formula (1) is a polymer, the compound preferably has the partial structure at the side chain of the polymer.

The molecular weight of the compound having the partial structure represented by Formula (1) is preferably in a range of 50 to 1000000 and more preferably in a range of 500 to 500000. When the molecular weight is set in the above-described range, it is possible to more effectively achieve the effects of the present invention.

The content of the compound having the partial structure represented by Formula (1) is preferably in a range of 5% by mass to 80% by mass and more preferably in a range of 10% by mass to 60% by mass in the composition of the present invention.

Specific examples of the compound having the partial structure represented by Formula (1) include compounds having structures described below or exemplary compounds described below, but the compound is not limited thereto. In the present invention, particularly, the compound having the partial structure represented by Formula (1) is preferably polyacrylamide.

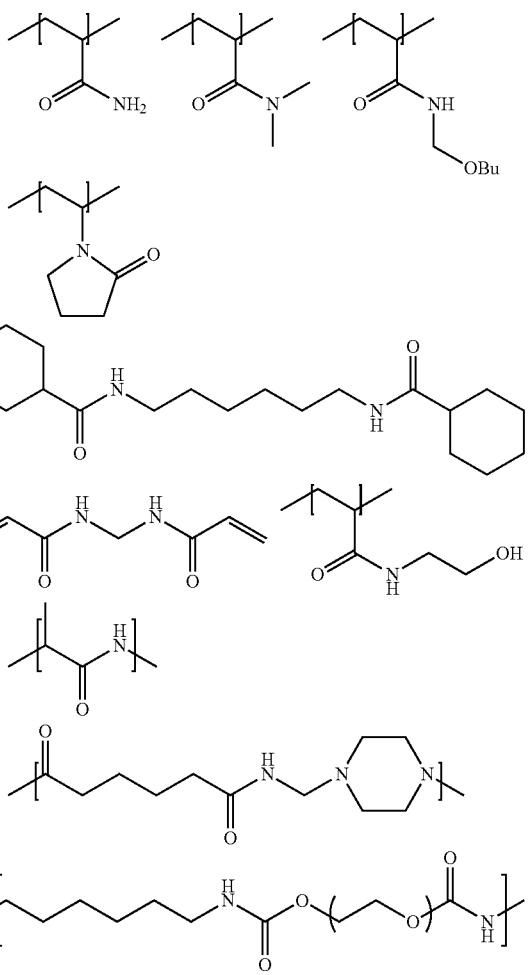

In addition, specific examples of the compound having the partial structure represented by Formula (1) include water-soluble polymers and examples of the preferred main chain structure include polyvinylpyrrolidone, poly(meth) acrylamide, polyamide, polyurethane, and polyuria. The water-soluble polymer may be a copolymer and the copolymer may be a random copolymer.

As the polyvinylpyrrolidone, trade names K-30 (manufactured by Nippon Shokubai Co., Ltd.) can be used.

Examples of the poly(meth)acrylamide include polymers and copolymers of (meth)acrylamide. Specific examples of the acrylamide include acrylamide, N-methylacrylamide, N-ethylacrylamide, N-propylacrylamide, N-butylacrylamide, N-hexylacrylamide, N-hydroxyethylacrylamide, N-phenylacrylamide, N-tolylacrylamide, N-(hydroxyphenyl)acrylamide, N-(sulfamoylphenyl)acrylamide, N-(phenylsulfonyl)acrylamide, N-(tolylsulfonyl)acrylamide, N,N-dimethylacrylamide, N-methyl-N-phenylacrylamide, N-hydroxyethyl-N-methylacrylamide, and the like. In addition, methacrylamides corresponding to the above-described poly(meth)acrylamides can also be used in a similar manner.

Examples of the water-soluble polyamide resin particularly include compounds obtained by copolymerizing a polyamide resin and a hydrophilic compound. A derivative of the water-soluble polyamide resin refers to a compound in which the structure of an amide bond is changed by the substitution or addition reaction of an atom in the water-soluble polyamide resin molecule such as a compound in which a water-soluble polyamide resin is used as a raw material and a hydrogen atom in an amid bond (—CONH—) is substituted with a methoxymethyl group (—$CH_2OCH_3$).

Examples of the polyamide resin include so-called "n-nylon" that is synthesized by the polymerization of ω amino acids and so-called "n,m-nylon" that is synthesized by the copolymerization of a diamine and dicarboxylic acid. Among these, from the viewpoint of imparting hydrophilic properties, a copolymer of a diamine and dicarboxylic acid is preferred and a reaction product of ∈-caprolactam and dicarboxylic acid is more preferred.

Examples of a hydrophilic compound include hydrophilic nitrogen-containing cyclic compounds, polyalkylene glycols, and the like.

Here, the hydrophilic nitrogen-containing cyclic compound refers to a compound including a ternary amine component at the side chain or the main chain and examples thereof include aminoethyl piperazine, bisaminopropyl piperazine, α-dimethylamino ∈-caprolactam, and the like.

Meanwhile, in the compound in which the polyamide resin and the hydrophilic compound are copolymerized together, for example, at least one selected from the group consisting of hydrophilic nitrogen-containing cyclic compounds and polyalkylene glycols is copolymerized at the main chain of the polyamide resin. Therefore, the hydrogen bond capability at the amide-bonded portion in the polyamide resin is strong with respect to N-methoxymethylated nylon.

Among the compounds in which the polyamide resin and the hydrophilic compound are copolymerized together, 1) the reaction products of ∈-caprolactam, the hydrophilic nitrogen-containing cyclic compound, and dicarboxylic acid and 2) the reaction products of ∈-caprolactam, polyalkylene glycol, and dicarboxylic acid are preferred.

The above-described compounds are commercially available under a trademark of, for example, "AQ NYLON" from Toray Fine Chemicals Co., Ltd. The reaction products of ∈-caprolactam, the hydrophilic nitrogen-containing cyclic compound, and dicarboxylic acid can be procured from AQ NYLON A-90 manufactured by Toray Fine Chemicals Co., Ltd., and the reaction products of ∈-caprolactam, polyalkylene glycol, and dicarboxylic acid can be procured from AQ NYLON P-70 manufactured by Toray Fine Chemicals Co., Ltd. AQ NYLON A-90, P-70, P-95, and T-70 (manufactured by Toray Fine Chemicals Co., Ltd.) can be used.

The molar ratio between a repeating unit that includes the partial structure represented by Formula (1) described above and a polymer having a repeating unit that includes an epoxy group is preferably in a range of 10/90 to 90/10 and more preferably in a range of 30/70 to 70/30. The weight-average molecular weight of the copolymer is preferably in a range of 3,000 to 1,000,000 and more preferably in a range of 5,000 to 200,000.

For the above-described polymerizing compounds, the details of the structure and the use method such as whether the polymerizing compounds are used singly or jointly and the amount added can be arbitrarily designed in accordance with the final performance design of the near-infrared-absorbing composition. For example, from the viewpoint of sensitivity, a structure having a large content of an unsaturated group in one molecule is preferred and, in many cases, a di- or more-functional compound is preferred. In addition, from the viewpoint of increasing the strength of the near-infrared cut-off filter, a tri- or more-functional compound is preferred, and, furthermore, when compounds having different functional groups and different polymerizable groups (for example, acrylic acid esters, methacrylic acid esters, styrene-based compounds, or vinyl ether-based compounds) are jointly used, it is also effective to adjust both sensitivity and strength. Regarding the compatibility with other components included in the near-infrared-absorbing composition (for example, metal oxides, pigments, and polymerization initiators) and dispersibility as well, the selection and use method of the polymerizing compound are important factors and, for example, when a low-purity compound is used or two or more compounds are jointly used, compatibility can be improved. In addition, from the viewpoint of improving adhesiveness to the curable surface of a supporter or the like, it is also possible to select a specific structure.

The amount of the polymerizing compound added to the composition of the present invention is in a range of 1% by mass to 80% by mass, more preferably in a range of 5% by mass to 50% by mass, and particularly preferably in a range of 7% by mass to 30% by mass in relation to the total solid content excluding the solvent.

In addition, in a case in which the polymer having a repeating unit that includes a crosslinked group is used as the polymerizing compound, the amount of the polymerizing compound added is set to a range of 10% by mass to 75% by mass, more preferably to a range of 20% by mass to 65% by mass, and particularly preferably to a range of 20% by mass to 60% by mass in relation to the total solid content of the composition of the present invention excluding the solvent.

The number of the polymerizing compounds may be one or more and, in a case in which two or more polymerizing compounds are used, the total amount thereof needs to fall into the above-described range.

<Binder Polymer>

The present invention may further include a binder polymer in addition to the above-described polymerizing compound for the purpose of improving coat characteristics. As the binder polymer, an alkali-soluble resin is preferably used. When the present invention includes an alkali-soluble resin, heat resistance and the like are improved and coating appropriateness can be finely adjusted.

The alkali-soluble resin can be appropriately selected from alkali-soluble resins which are linear organic macromolecular polymers and have at least one group that accelerates alkali soluble properties in the molecule (preferably a molecule including an acryl-based copolymer or a styrene-based copolymer as a main chain). From the viewpoint of heat resistance, polyhydroxystrene-based resins, polysiloxane-based resins, acryl-based resins, acrylamide-based resins, acryl/acrylamide copolymer resins are preferred and, from the viewpoint of the control of developing properties, acryl-based resins, acrylamide-based resins, and acryl/acrylamide copolymer resins are preferred.

Examples of the group that accelerates alkali-soluble properties (hereinafter, also referred to as the acid group) include carboxyl groups, phosphoric acid groups, sulfonic acid groups, phenolic hydroxyl groups, and the like. Groups which are soluble in an organic solvent and can be developed using a weak alkaline aqueous solution are preferred and (meth)acrylic acid groups are particularly preferred. The number of the acid groups may be one or more.

Examples of monomers capable of imparting the acid group after being polymerized include monomers having a hydroxyl group such as 2-hydroxyethyl(meth)acrylates, monomers having an epoxy group such as glycidyl(meth)acrylate, monomers having an isocyanate group such as 2-isocyanatoethyl(meth)acrylate, and the like. The number of kinds of monomers for introducing the acid group may be one or more. In order to introduce the acid group into the alkali-soluble binder, for example, it is possible to polymerize a monomer having the acid group and/or a monomer capable of imparting the acid group after being polymerized (hereinafter, in some cases, referred to as "monomers for introducing the acid group") as monomer components. Meanwhile, in a case in which the acid group is introduced as a monomer component using the monomers capable of imparting the acid group after being polymerized, for example, a treatment for imparting the acid group as described below after the polymerization of the monomers becomes necessary.

For the production of the alkali-soluble resin, for example, it is possible to apply a method in which a well-known radical polymerization method is used. A variety of polymerization conditions when the alkali-soluble resin is produced using the radical polymerization method such as temperature, pressure, the kind and amount of a radical initiator, and the kind of the solvent can be easily set by a person skilled in the art and it is also possible to experimentally specify the conditions.

The linear organic macromolecular polymer used as the alkali-soluble resin is preferably a polymer including carboxylic acid at the side chain and, regarding the above-described polymer, the description in Paragraph <0561> (Paragraph <0691> in the specification of the corresponding US2012/0235099A) and the like in JP2012-208494A can be referenced and the content thereof is incorporated into the specification of the present application by reference.

The alkali-soluble resin also preferably includes a polymer (a) obtained by polymerizing monomer components essentially including a compound (hereinafter, in some cases, also referred to as "ether dimer") represented by General Formula (ED) described below:

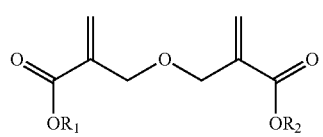

General Formula (ED)

(in Formula (ED), each of $R^1$ and $R^2$ independently represents a hydrogen atom or a hydrocarbon group having 1 to 25 carbon atoms) as a polymer component (A) that is an essential component. Therefore, the composition of the present invention is capable of forming a cured coated film that is excellent in terms of not only heat resistance but also transparency. In General Formula (1) representing the ether dimer, there is no particular limitation regarding the hydrocarbon group having 1 to 25 carbon atoms represented by $R^1$ and $R^2$ and examples thereof include linear or branched alkyl groups such as methyl, ethyl, n-propyl, isopropyl, n-butyl, isobutyl, t-butyl, t-amyl, stearyl, lauryl, and 2-ethylhexyl; aryl groups such as phenyl; alicyclic groups such as cyclohexyl, t-butylcyclohexyl, dicyclopentadienyl, tricyclodecanyl, isobornyl, adamantyl, and 2-methyl-2-adamantyl; alkyl groups substituted with an alkoxy such as 1-methoxyethyl and 1-ethyoxyethyl; alkyl groups substituted with an aryl group such as benzyl; and the like. Among these, substituents of primary or secondary carbon that are not easily detached due to an acid or heat such as methyl, ethyl, cyclohexyl, and benzyl are preferred in terms of heat resistance.

Regarding specific examples of the ether dimer, the description of Paragraph <0565> (Paragraph <0694> in the specification of the corresponding US2012/0235099A) and the like in JP2012-208494A can be referenced and the content thereof is incorporated into the specification of the present application by reference.

In the present invention, the configuration unit derived from the ether dimer is preferably in a range of 1 mol % to 50 mol % and more preferably in a range of 1 mol % to 20 mol % of all.

Together with the ether dimer, another monomer may be copolymerized.

Examples of the monomer that can be copolymerized with the ether dimer include the monomers for introducing the acid group, monomers for introducing a radical polymerizing double bond, monomers for introducing an epoxy group, and copolymerizable monomers other than the above-described monomers. The above-described monomers may be used singly or a combination of two or more monomers may be used.

Examples of the monomers for introducing the acid group include monomers having a carboxyl group such as (meth)acrylic acids and itaconic acid, monomers having a phenolic hydroxyl group such as N-hydroxyphenyl maleimide, monomers having a carboxylic acid anhydride group such as maleic acid anhydride or itaconic acid anhydride, and the like. Among these, (meth)acrylic acids are particularly preferred.

In addition, the monomers for introducing the acid group may be monomers capable of imparting the acid group after being polymerized and examples thereof include monomers having a hydroxyl group such as 2-hydroxyethyl(meth)acrylates, monomers for introducing an epoxy group such as glycidyl(meth)acrylates, monomers having an isocyanate group such as 2-isocyanatoethyl(meth)acrylates, and the like. In a case in which the monomer for introducing a radical polymerizing double bond is used and in a case in which the monomer capable of imparting the acid group after being polymerized is used, it is necessary to carry out a treatment that imparts the acid group after the polymerization. The treatment that imparts the acid group after the polymerization of the monomers varies depending on the kind of the monomer and examples thereof include the following treatments. In a case in which the monomer having hydroxyl group is used, examples of the treatment include a treatment that adds an acid anhydride such as succinic acid anhydride, tetrahydrophthalic acid anhydride, or maleic acid anhydride. In a case in which the monomer having an epoxy group is used, examples of the treatment include a treatment that adds a compound having an amino group and the acid group such as N-methyl amino benzoate or N-methylaminophenol or a treatment that adds an acid anhydride such as succinic acid anhydride, tetrahydrophthalic acid anhydride, or maleic acid anhydride to a hydroxyl group generated after the addition of an acid such as (meth)acrylic acid. In a case in which the monomer having an isocyanate group is used, examples of the treatment include a treatment that adds a compound having a hydroxyl group and the acid group such as 2-hydroxybutyric acid.

In a case in which the polymer obtained by polymerizing monomer components including the compound represented by General Formula (ED) includes a monomer for introducing the acid group, the content ratio thereof is not particularly limited, but is preferably in a range of 5 mass % to 70 mass % and more preferably in a range of 10 mass % to 60 mass % in relation to the total monomer components.

Examples of the monomers for introducing a radical polymerizing double bond include monomers having a carboxyl group such as (meth)acrylic acids and itaconic acid; monomers including a carboxyl acid anhydride group such as maleic acid anhydride or itaconic acid anhydride; monomers having an epoxy group such as glycidyl(meth)acrylate, 3,4-epoxycyclohexylmethyl(meth)acrylate, or o-(or m- or p-)vinylbenzyl glycidyl ether; and the like. In a case in which the monomer for introducing a radical polymerizing double bond is used, it is necessary to carry out a treatment for imparting a radical polymerizing double bond after the polymerization of the monomers. The treatment for imparting a radical polymerizing double bond group after the polymerization of the monomers varies depending on the kind of the monomer and examples thereof include the following treatments. In a case in which the monomer having a carboxyl group such as (meth)acrylic acid or itaconic acid is used, examples of the treatment include a treatment that adds a compound including an epoxy group such as glycidyl(meth)acrylate, 3,4-epoxycyclohexylmethyl (meth)acrylate, or o-(or m- or p-)vinylbenzyl glycidyl ether and a radical polymerizing double bond. In a case in which the monomer having a carboxylic acid anhydride group such as maleic acid anhydride or itaconic acid anhydride is used, examples of the treatment include a treatment that adds a compound having a hydroxyl group such as 2-hydroxyethyl (meth)acrylate and a radical polymerizing double bond. In a case in which the monomer having an epoxy group such as glycidyl(meth)acrylate, 3,4-epoxycyclohexylmethyl(meth) acrylate, or o-(or m- or p-)vinylbenzyl glycidyl ether is used, examples of the treatment include a treatment that adds a compound having the acid group such as (meth)acrylic acid and a radical polymerizing double bond.

In a case in which the polymer obtained by polymerizing monomer components including the compound represented by General Formula (ED) includes the monomer for introducing a radical polymerizing double bond, the content ratio thereof is not particularly limited, but is preferably in a range of 5 mass % to 70 mass % and more preferably in a range of 10 mass % to 60 mass % in relation to the total monomer components.

Examples of the monomer for introducing an epoxy group include glycidyl (meth)acrylate, 3,4-epoxycyclohexylm-ethyl(meth)acrylate, o-(or m- or p-)vinylbenzyl glycidyl ether; and the like.

In a case in which the polymer obtained by polymerizing monomer components including the compound represented by General Formula (ED) includes the monomer for introducing an epoxy group, the content ratio thereof is not particularly limited, but is preferably in a range of 5 mass % to 70 mass % and more preferably in a range of 10 mass % to 60 mass % in relation to the total monomer components.

Regarding another copolymerizable monomer, for example, the description of Paragraph <0328> and the like in JP2012-046629A can be referenced and the content thereof is incorporated into the specification of the present application by reference.

In a case in which the polymer obtained by polymerizing monomer components including the compound represented by General Formula (ED) includes another copolymerizable monomer, the content ratio thereof is not particularly limited, but is preferably 95 mass % or less and more preferably 85 mass % or less.

The weight-average molecular weight of the polymer obtained by polymerizing the monomer components including the compound represented by General Formula (ED) is not particularly limited; however, from the viewpoint of the viscosity of the near-infrared-absorbing composition and the heat resistance of a coated film formed using the composition, the weight-average molecular weight thereof is preferably in a range of 2000 to 200000, more preferably in a range of 5000 to 100000, and still more preferably in a range of 5000 to 20000.

In addition, in a case in which the polymer obtained by polymerizing the monomer components including the compound represented by General Formula (ED) includes the acid group, the acid value is preferably in a range of 30 mgKOH/g to 500 mgKOH/g and more preferably in a range of 50 mgKOH/g to 400 mgKOH/g.

The polymer obtained by polymerizing the monomer components including the compound represented by General Formula (ED) can be easily obtained by polymerizing the above-described monomers essentially including the ether dimer. At this time, the cyclization reaction of the ether dimer proceeds together with polymerization and thus a tetrahydrofuran ring structure is formed.

There is no particular limitation regarding the polymerization method applied for the synthesis of the polymer obtained by polymerizing the monomer components including the compound represented by General Formula (ED) and a variety of well-known polymerization methods of the related art can be employed, but a solution polymerization method is preferred. In detail, for example, it is possible to synthesize a polymer obtained by polymerizing monomer components including the compound represented by General Formula (ED) according to the synthesis method of a polymer (a) described in JP2004-300204A.

Hereinafter, exemplary compounds of the polymer obtained by polymerizing the monomer components including the compound represented by General Formula (ED) will be described, but the present invention is not limited thereto. The compositional ratios between the exemplary compounds described below are expressed using mol %.

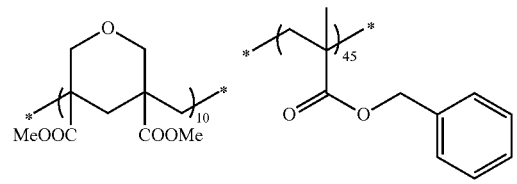

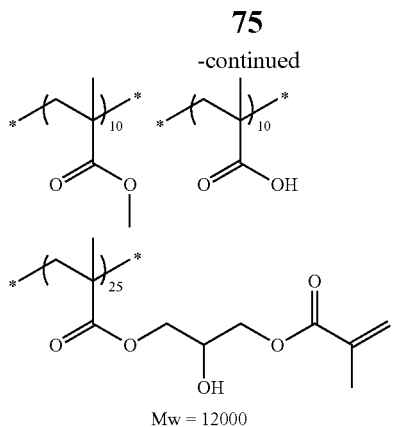

Mw = 12000

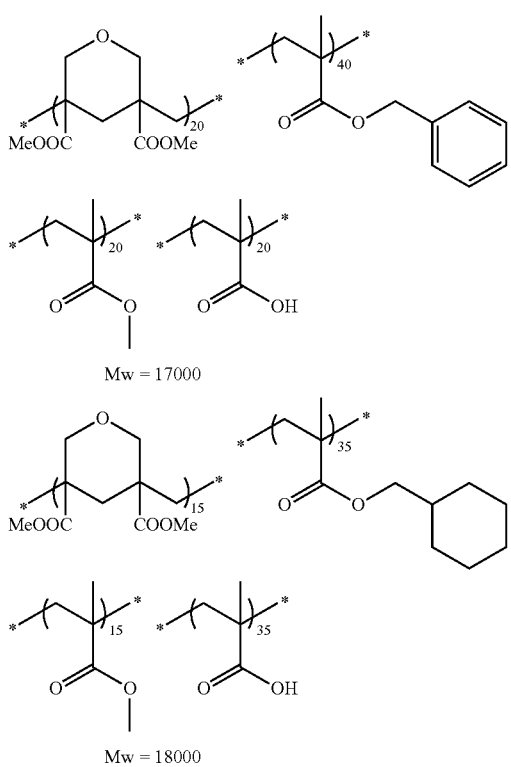

Mw = 17000

Mw = 18000

Mw = 18000

Mw = 18000

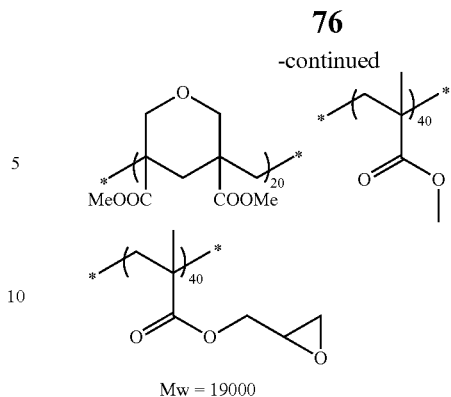

Mw = 19000

In the present invention, particularly, copolymers obtained by copolymerizing dimethyl-2,2'-[oxybis(methylene)]bis-2-propenoate (hereinafter, referred to as "DM"), benzyl methacrylate (hereinafter, referred to as "BzMA"), methyl methacrylate (hereinafter, referred to as "MMA"), methacrylic acid (hereinafter, referred to as "MAA"), or glycidyl methacrylate (hereinafter, referred to as "GMA") are preferred. Particularly, the molar ratio between DM:BzMA:MMA:MAA:GMA is preferably 5 to 15:40 to 50:5 to 15:5 to 15:20 to 30. The above-described components preferably account for 95 mass % or more of the components that configure the copolymer used in the present invention. In addition, the weight-average molecular weight of the above-described polymer is preferably in a range of 9000 to 20000.

In the present invention, an alkali-soluble phenol resin can also be preferably used. Examples of the alkali-soluble phenol resin include novolac resins, vinyl polymers, and the like.

Examples of the novolac resins include resins obtained by condensing a phenol and an aldehyde in the presence of an acid catalyst. Examples of the phenol include phenol, cresol, ethylphenol, butylphenol, xylenol, phenylphenol, catechol, resorcinol, pyrogallol, naphthol, bisphenol A, and the like.

Examples of the aldehyde include formaldehyde, paraformaldehyde, acetoaldehyde, propionaldehyde, benzaldehyde, and the like.

The phenol and the aldehyde can be used singly or a combination of two or more kinds thereof can be used.

Specific examples of the novolac resin include condensation products between methacresol, paracresol, or a mixture thereof and formalin.

For the novolac resin, the molecular weight distribution may be adjusted using means such as separation. Alternatively, a low-molecular-weight component having a phenol-based hydroxyl group such as bisphenol C or bisphenol A may be mixed in the novolac resin.

As the alkali-soluble resin, particularly, benzyl(meth)acrylate/(meth)acrylic acid copolymers or multi-component copolymers made up of benzyl(meth)acrylate/(meth)acrylic acid/other monomers are preferred. Additionally, copolymers obtained by copolymerizing 2-hydroxyethyl methacrylate, 2-hydroxypropyl(meth)acrylate/polystyrene macromonomer/benzyl methacrylate/methacrylic acid copolymers, 2-hydroxy-3-phenoxypropyl acrylate/polymethyl methacrylate macromonomer/benzyl methacrylate/methacrylic acid copolymers, 2-hydroxyethyl methacrylate/polystyrene macromonomer/methyl methacrylate/methacrylic acid copolymers, 2-hydroxyethyl methacrylate/polystyrene macromonomer/benzyl methacrylate/ methacrylic acid copolymers, and the like, which are described in JP1995-140654A (JP-H7-140654A) can be used.

The acid value of the alkali-soluble resin is preferably in a range of 30 mgKOH/g to 200 mgKOH/g, more preferably in a range of 50 mgKOH/g to 150 mgKOH/g, and most preferably in a range of 70 mgKOH/g to 120 mgKOH/g.

In addition, the weight-average molecular weight (Mw) of the alkali-soluble resin is preferably in a range of 2,000 to 50,000, more preferably in a range of 5,000 to 30,000, and most preferably in a range of 7,000 to 20,000.

The content of the binder polymer in the present invention is preferably in a range of 1 mass % to 80 mass %, more preferably in a range of 5 mass % to 50 mass %, and still more preferably in a range of 7 mass % to 30 mass % in relation to the total solid content of the composition.

<Surfactant>

The composition of the present invention may include a surfactant. Only one surfactant may be used or a combination of two or more surfactants may be used. The amount of the surfactant added is preferably in a range of 0.0001% by mass to 2% by mass, more preferably in a range of 0.005% by mass to 1.0% by mass, and still more preferably in a range of 0.01% by mass to 0.1% by mass in relation to the solid content of the composition of the present invention.

As the surfactant, a variety of surfactants such as a fluorine-based surfactant, a nonionic surfactant, a cationic surfactant, an anionic surfactant, and a silicone-based surfactant can be used.

Particularly, when the composition of the present invention includes at least any of fluorine-based surfactants and silicone-based surfactants, the liquid characteristics (particularly, fluidity) are further improved when a coating fluid is produced and thus the uniformity of the coating thickness or liquid-saving properties is further improved.

That is, in a case in which a film is formed using a coating fluid to which the composition including at least any one of fluorine-based surfactants and silicone-based surfactants is applied, the surface tension between a surface to be coated and the coating fluid decreases and thus the wetting properties to the surface to be coated improves and the coating properties to the surface to be coated improves. Therefore, in a case in which a thin film having a thickness of approximately several micrometers is formed using a small amount of the fluid as well, the inclusion of the surfactant is effective since a film having a uniform thickness with little thickness variation is more preferably formed.

The content ratio of fluorine in the fluorine-based surfactant is preferably in a range of 3% by mass to 40% by mass, more preferably in a range of 5% by mass to 30% by mass, and particularly preferably in a range of 7% by mass to 25% by mass. A fluorine-based surfactant having a content ratio of fluorine in the above-described range is effective in terms of the uniformity of the thickness of a coated film or liquid-saving properties and also has favorable solubility in the near-infrared absorbing composition.

Examples of the fluorine-based surfactant include MEGAFAC F171, MEGAFAC F172, MEGAFAC F173, MEGAFAC F176, MEGAFAC F177, MEGAFAC F141, MEGAFAC F142, MEGAFAC F143, MEGAFAC F144, MEGAFAC R30, MEGAFAC F437, MEGAFAC F479, MEGAFAC F482, MEGAFAC F554, MEGAFAC F780, MEGAFAC R08 (all manufactured by DIC Corporation), FLORADO FC430, FLORADO FC431, FLORADO FC171 (all manufactured by Sumitomo 3M Limited), SAFLON S-382, SAFLON S-141, SAFLON S-145, SAFLON SC-101, SAFLON SC-103, SAFLON SC-104, SAFLON SC-105, SAFLON SC1068, SAFLON SC-381, SAFLON SC-383, SAFLON 5393, SAFLON H-40 (all manufactured by Asahi Glass Co., Ltd.), EFTOP EF301, EFTOP EF303, EFTOP EF351, EFTOP EF352 (all manufactured by Jemco Inc.), PF636, PF656, PF6320, PF6520, PF7002 (manufactured by OMNOVA Solutions Inc.), and the like.

As the fluorine-based surfactant, a polymer having a fluoroaliphatic group is also preferred. Examples of the polymer having a fluoroaliphatic group include fluorine-based surfactants obtained from fluoroaliphatic compounds which have a fluoroaliphatic group which is manufactured using a telomerization method (also called a telomer method) or an oligomerization method (also called an oligomer method).

Here, the "telomerization method" refers to a method for synthesizing a compound having 1 or 2 active groups in the molecule by polymerizing low-molecular-weight substances. In addition, the "oligomerization method" refers to a method for converting a monomer or a mixture of monomers to an oligomer.

Examples of the fluoroaliphatic group in the present invention include —$CF_3$ group, —$C_2F_5$ group, —$C_3F_7$ group, —$C_4F_9$ group, —$O_5F_{11}$ group, —$C_6F_{13}$ group, —$C_7F_{15}$ group, —$C_8F_{17}$ group, $C_9F_{19}$ group, and $C_{10}F_{21}$ group and, in terms of compatibility and coating properties, —$C_2F_5$ group, —$C_3F_7$ group, —$C_4F_9$ group, —$O_5F_{11}$ group, —$C_6F_{13}$ group, —$C_7F_{15}$ group, and —$C_8F_{17}$ group are preferred.

The fluoroaliphatic compound in the present invention can be synthesized using the method described in JP2002-90991A.

The polymer having the fluoroaliphatic group in the present invention is preferably a copolymer of a monomer having the fluoroaliphatic group in the present invention and (poly(oxyalkylene)acrylate and/or (poly(oxyalkylene)) methacrylate. The copolymer may be irregularly distributed or block-copolymerized. In addition, examples of the poly (oxyalkylene) group include a poly(oxyethylene) group, a poly(oxypropylene) group, a poly(oxybutylene) group, and the like and the poly(oxyalkylene) group may be a unit having alkylenes having different chain lengths in the same chain length such as a poly(a block-linked body of oxyethylene, oxypropylene, and oxyethylene) group or a poly (block-linked body of oxyethylene, oxypropylene, and oxyethylene) group. Furthermore, the copolymer of a monomer having the fluoroaliphatic group and (poly(oxyalkylene)) acrylate (or methacrylate) may be not only a two-component copolymer but also a three or more-component copolymer of monomers having two or more different kinds of fluoroaliphatic groups or two or more different kinds of (poly (oxyalkylene))acrylate (or methacrylate).

Examples of commercially available surfactants including the polymer having the fluoroaliphatic group in the present invention include the surfactants described in Paragraph <0552> in JP2012-208494A (<0678> in the specification of US2012/0235099A) and the content thereof is incorporated into the specification of the present application. In addition, it is possible to use a copolymer MEGAFAC F-781 (manufactured by DIC Corporation), acrylate (or methacrylate) having a $C_6F_{13}$ group, (poly(oxyethylene))acrylate (or methacrylate), and (poly(oxypropylene))acrylate (or methacrylate), a copolymer of acrylate (or methacrylate) having a $C_8F_{17}$ group and (poly(oxyalkylene))acrylate (or methacrylate), a copolymer of acrylate (or methacrylate) having a $C_8F_{17}$ group, (poly(oxyethylene))acrylate (or methacrylate), and (poly(oxypropylene))acrylate (or methacrylate), or the like.

Examples of nonionic surfactants include polyoxyethylene alkyl ethers, polyoxyethylene alkyl allyl ethers, polyoxyethylene aliphatic acid esters, sorbitan aliphatic esters, polyoxyethylene sorbitan aliphatic acid esters, polyoxyethylene alkyl amines, glycerin aliphatic acid esters, oxyethyleneoxy propylene block copolymers, acetylene glycol-based surfactants, acetylene-based polyoxyethylene oxides, and the like. The above-described surfactants can be used singly or two or more surfactants can be used.

Examples of specific commercially available products thereof include SURFYNOL 61, 82, 104, 104E, 104H, 104A, 104BC, 104DPM, 104PA, 104PG-50, 104S, 420, 440, 465, 485, 504, CT-111, CT-121, CT-131, CT-136, CT-141, CT-151, CT-171, CT-324, DF-37, DF-58, DF-75, DF-110D, DF-210, GA, OP-340, PSA-204, PSA-216, PSA-336, SE, SE-F, TG, GA, DYNOL 604 (all manufactured by Nissin Chemical Co., Ltd. and Air Products & Chemicals, Inc.), OLFIN A, B, AK-02, CT-151W, E1004, E1010, P, SPC, STG, Y, 32W, PD-001, PD-002W, PD-003, PD-004, EXP. 4001, EXP. 4036, EXP. 4051, AF-103, AF-104, SK-14, AE-3 (all manufactured by Nissin Chemical Co., Ltd.), ACETYLENOL E00, E13T, E40,E60, E81, E100, E200 (all are trade names and are manufactured by Kawaken Fine Chemicals Co., Ltd.), and the like. Among these, OLFIN E1010 is preferred.

Additionally, regarding the nonionic surfactants, specifically, the nonionic surfactants described in Paragraph <0553> in JP2012-208494A (<0679> in the specification of the corresponding US2012/0235099A) can be referenced and the contents thereof can be incorporated into the specification of the present application by reference.

Specific examples of cationic surfactants include the cationic surfactants described in Paragraph <0554> in JP2012-208494A (<0680> in the specification of the corresponding US2012/0235099A) and the contents thereof can be incorporated into the specification of the present application by reference.

Specific examples of the anionic surfactants include W004, W005, W017 (manufactured by Yusho Co., Ltd.), and the like.

Examples of silicone-based surfactants include the silicone-based surfactants described in Paragraph <0556> in JP2012-208494A (<0682> in the specification of the corresponding US2012/0235099A) and the contents thereof can be incorporated into the specification of the present application by reference. In addition, examples thereof also include "TORAY SILICONE SF8410", TORAY SILICONE SF8427", TORAY SILICONE SF8400", "ST80PA", "ST83PA", "ST86PA" all manufactured by Dow Corning Toray Co., Ltd., "TSF-400", "TSF-401", "TSF-410", "TSF-4446" manufactured by Momentive Performance Materials Worldwide Inc., "KP321", "KP323", "KP324", "KP340" manufactured by Shin-Etsu Chemical Co., Ltd. and the like.

<Polymerization Initiator>

The composition of the present invention may include a polymerization initiator. The number of the polymerization initiators included may be one or more and, in a case in which the composition includes two or more polymerization initiators, the total amount thereof falls into the following range. The content of the polymerization initiator is preferably in a range of 0.01% by mass to 30% by mass, more preferably in a range of 0.1% by mass to 20% by mass, and particularly preferably in a range of 0.1% by mass to 15% by mass.

The polymerization initiator is not particularly limited as long as the polymerization initiator has the capability of initiating the polymerization of the polymerizing compounds using either or both light and heat and can be appropriately selected depending on the purpose, but is preferably a photopolymerizing compound. In a case in which polymerization is initiated using light, the polymerization initiator preferably has photosensitivity to light rays in an ultraviolet to visible light range.

In addition, in a case in which polymerization is initiated using heat, a polymerization initiator that is decomposed at a temperature in a range of 150° C. to 250° C. is preferred.

The polymerization initiator that can be used in the present invention is preferably a compound having at least an aromatic group and examples thereof include acylphosphine compounds, acetophenone-based compounds, α-aminoketone compounds, benzophenone-based compounds, benzoin ether-based compounds, ketal derivative compounds, thioxanthone compounds, oxime compounds, hexaaryl biimidazole compounds, trihalomethyl compounds, azo compounds, organic peroxides, onium salt compounds such as diazonium compounds, iodonium compounds, sulfonium compounds, azinium compounds, and metallocene compounds, organic borate compounds, disulfo compounds, and the like.

From the viewpoint of sensitivity, oxime compounds, acetophenone-based compounds, α-aminoketone compounds, trihalomethyl compounds, hexaaryl biimidazole compounds, and thiol compounds are preferred.

Regarding the acetophenone-based compounds, the trihalomethyl compounds, the hexaaryl biimidazole compounds, and the oxime compounds, specifically, the description in Paragraphs <0506> to <0510> in JP2012-208494A (<0622> to <0628> in the specification of the corresponding US2012/0235099A) and the like can be referenced and the content thereof is incorporated into the specification of the present application by reference.

Preferably, furthermore, the polymerization initiator can also be preferably used for the cyclic oxime compounds described in JP2007-231000A and JP2007-322744A.

Additional examples thereof include the oxime compounds having a specific substituent described in JP2007-269779A and the oxime compounds having a thioaryl group described in JP2009-191061A.

Specifically, the oxime compounds are also preferably compounds represented by Formula (1) described below. Meanwhile, the N—O bond in an oxime may be an oxime compound of an (E) body, an oxime compound of a (Z) body, or a mixture of the (E) body and the (Z) body. Regarding the compound represented by Formula (1), the description of the compound represented by Formula (OX-1) or (OX-2) in Paragraphs <0513> (<0632> in the specification of the corresponding US2012/235099A) and thereafter in JP2012-208494A can be referenced and the content thereof is incorporated into the specification of the present application by reference.

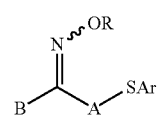

(1)

(In Formula (1), each of R and B independently represents a monovalent substituent, A represents a divalent organic group, and Ar represents an aryl group.)

The monovalent substituent represented by R is preferably a monovalent non-metal atomic group. Examples of the monovalent non-metal atomic group include alkyl groups having 1 to 30 carbon atoms, aryl groups having 6 to 30 carbon atoms, acyl groups having 2 to 20 carbon atoms, alkyoxcarbonyl groups having 2 to 20 carbon atoms, aryloxycarbonyl groups having 2 to 20 carbon atoms, heterocyclic groups, alkylthiocarbonyl groups, arylthiocarboxyl groups, and the like.

The monovalent substituent represented by B represents an aryl group, a heterocyclic group, an arylcarbonyl group, or a heterocyclic carbonyl group.

Examples of the divalent organic group represented by A include an alkylene group having 1 to 12 carbon atoms, a cyclohexylene group, and an alkylene group.

The above-described groups may have one or more substituents. In addition, the above-described substituent may be substituted with another substituent. Examples of the substituent include a halogen atom, an aryloxy group, an alkoxycarbonyl group, an aryloxy carbonyl group, an acyloxy group, an acyl group, an alkyl group, an aryl group, and the like.

Regarding specific examples of the oxime compounds that are preferably used, the description of Paragraph <0033> in JP2012-032556A, Paragraph <0033> in JP2012-122045A, and the like can be referenced and the content thereof is incorporated into the specification of the present application. (Plox-1) to (Plox-13) will be illustrated below, but the present invention is not limited thereto.

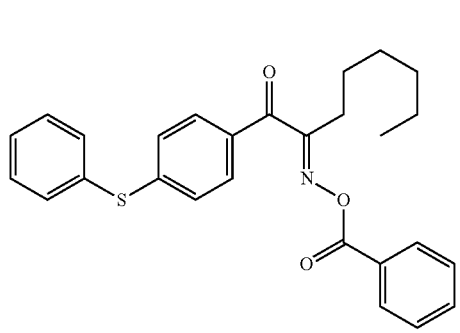
Plox-1

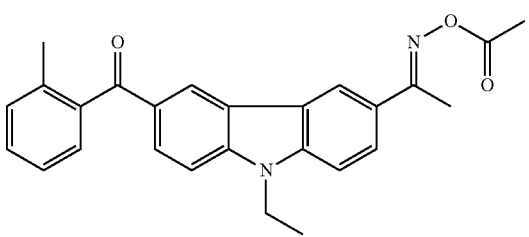
Plox-2

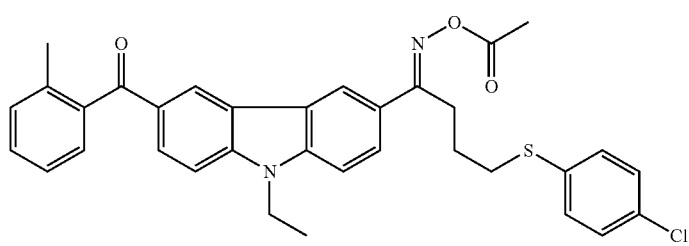
Plox-3

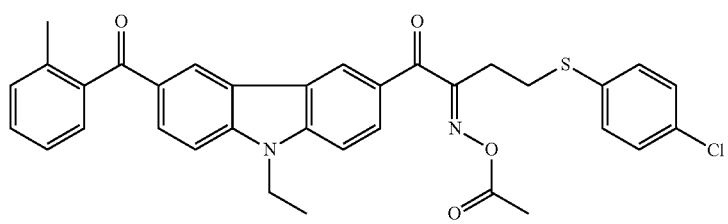
Plox-4

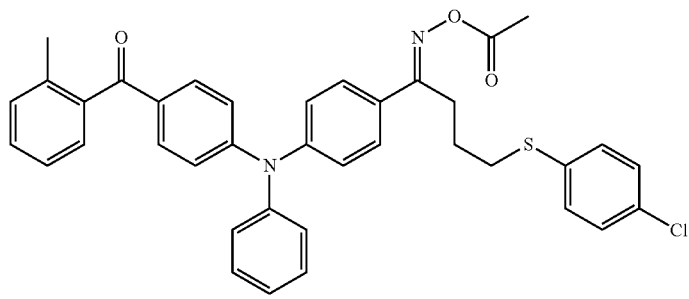
Plox-5

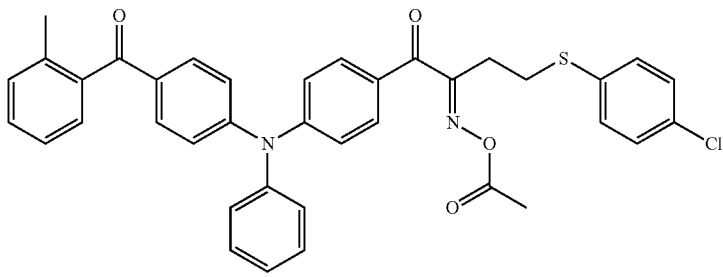
Plox-6
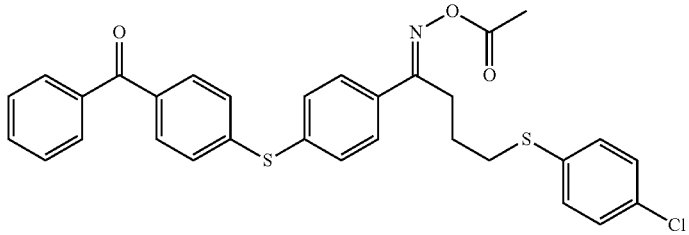
Plox-7
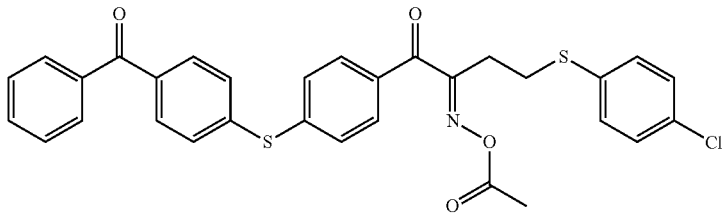
Plox-8
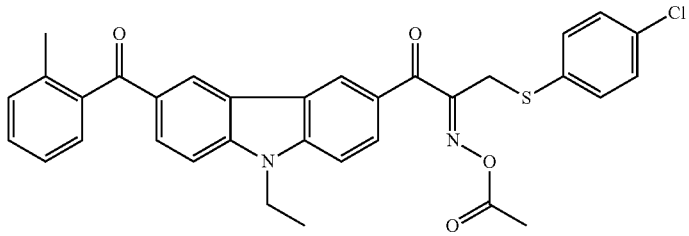
Plox-9
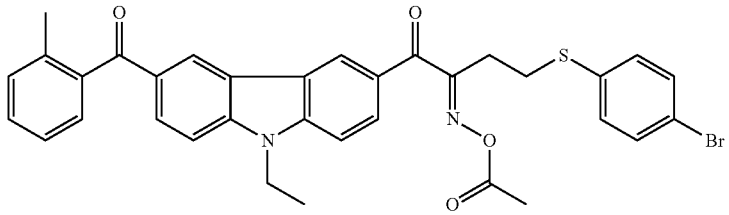
Plox-10
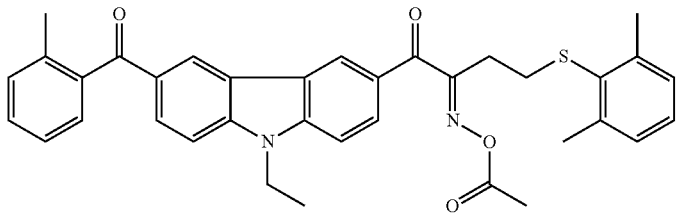
Plox-11

-continued

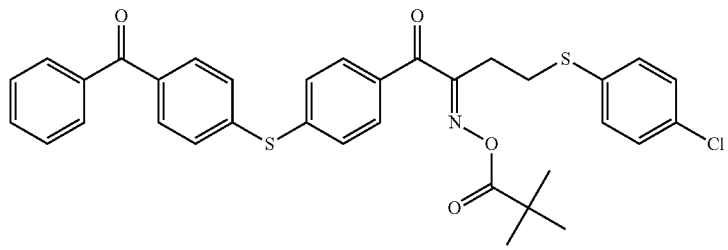
Plox-12

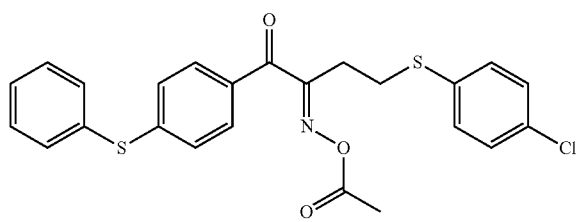
Plox-13

The oxime compound preferably has the maximum absorption wavelength in a wavelength range of 350 nm to 500 nm, more preferably has the maximum absorption wavelength in a wavelength range of 360 nm to 480 nm, and particularly preferably has high absorbance at 365 nm and 455 nm.

The mole absorption coefficient of the oxime compound at 365 nm or 405 nm is preferably in a range of 3,000 to 300,000, more preferably in a range of 5,000 to 300,000, and particularly preferably in a range of 10,000 to 200,000 from the viewpoint of sensitivity.

For the mole absorption coefficient of the compound, it is possible to use a well-known method and is preferably measured using, for example, a UV-visible spectrophotometer (Carry-5 spectrophotometer manufactured by Varian Inc.) and an ethyl acetate solvent at a concentration of 0.01 g/L.

A photopolymerization initiator is more preferably a compound selected from the group consisting of oxime compounds, acetophenone-based compounds, and acylphosphine compounds. More specifically, for example, it is also possible to use the aminoacetophenone-based initiators described in JP1998-291969A (JP-H10-291969A), the acylphosphine oxide-based initiators described in JP4225898B, the above-described oxime-based initiators, and, furthermore, as the oxime-based initiators, the compounds described in JP2001-233842A.

As the oxime compound, it is possible to use a commercially available products of IRGACURE-OXE01 (manufactured by BASF) or IRGACURE-OXE02 (manufactured by BASF). As the acetophenone-based initiator, it is possible to use commercially available products of IRGACURE-907, IRGACURE-369, and IRGACURE-379 (trade name, all manufactured by BASF Japan). In addition, as the acylphosphine-based initiator, it is possible to use a commercially available product of IRGACURE-819, and DAROCUR-TPO (trade name, all manufactured by BASF Japan).

<Other Components>

In the composition of the present invention, in addition to the above-described essential components and the above-described preferred additives, other components may be selectively used in an appropriate manner depending on the purpose as long as the effects of the present invention are not impaired.

Examples of the other components that can be jointly used include a binder polymer, a dispersing agent, a sensitizer, a crosslinking agent, a curing accelerator, a filler, a thermal curing accelerator, a thermopolymerization inhibitor, a plasticizer, and the like and, furthermore, an adhesion accelerator to the surface of a base material and other auxiliary agents (for example, conductive particles, a filler, a defoamer, a flame retardant, a leveling agent, a peeling accelerator, an antioxidant, a fragrance, a surface tension adjuster, a chain transfer agent, and the like) may also be jointly used.

When the composition of the present invention appropriately includes the above-described components, it is possible to adjust properties such as stability and film properties of the target near-infrared cut-off filter.

Regarding the above-described components, for example, the descriptions in Paragraphs <0183> and thereafter in JP2012-003225A, Paragraphs <0101> and <0102> in JP2008-250074A, Paragraphs <0103> and <0104> in JP2008-250074A, Paragraphs <0107> to <0109> in JP2008-250074A, and the like can be referenced and the contents thereof can be incorporated into the specification of the present application by reference.

Since the composition of the present invention may be in a liquid form, it is possible to easily produce the near-infrared cut-off filter by, for example, directly applying and drying the composition of the present invention and the production aptitude that has not been sufficient in the above-described near-infrared cut-off filter of the related art can be improved.

The use of the near-infrared-absorbing composition of the present invention is not particularly limited and examples thereof include compositions for near-infrared cut-off filters on the light-receiving side of a solid-state imaging element substrate (for example, compositions for near-infrared cut-off filters for wafer-level lenses, and the like), compositions for near-infrared cut-off filters on the back surface side of the solid-state imaging element substrate (the side opposite to the light-receiving side), and the like. The near-infrared-absorbing composition of the present invention is preferably used for light-shielding films on the light-receiving side of the solid-state imaging element substrate. Particularly, the near-infrared-absorbing composition of the present invention is preferably directly applied onto an image sensor for the solid-state imaging element. Particularly, the near-infrared-absorbing composition of the present invention is preferably directly applied onto an image sensor for a solid-state imaging sensor so as to form a coated film.

In addition, in a case in which an infrared cut-off layer is formed through coating, the viscosity of the near-infrared-absorbing composition of the present invention is preferably in a range of 1 mPa·s to 3000 mPa·s, more preferably in a range of 10 mPa·s to 2000 mPa·s, and still more preferably in a range of 100 mPa·s to 1500 mPa·s.

In a case in which the near-infrared-absorbing composition of the present invention is used for near-infrared cut-off filters on the light-receiving side of the solid-state imaging element substrate and an infrared cut-off layer is formed through coating, the viscosity thereof is preferably in a range of 10 mPa·s to 3000 mPa·s, more preferably in a range of 500 mPa·s to 1500 mPa·s, and most preferably in a range of 700 mPa·s to 1400 mPa·s from the viewpoint of thick film formability and uniform coating properties.

The present invention also relates to a laminate including a near-infrared cut-off layer obtained by curing the near-infrared-absorbing composition and a dielectric multilayer film. As preferred aspects of the laminate of the present invention, there are (i) an aspect in which a transparent supporter, a near-infrared cut-off layer, and a dielectric multilayer film are sequentially provided and (ii) an aspect in which a near-infrared cut-off layer, a transparent supporter, and a dielectric multilayer film are sequentially provided. The transparent supporter may be any of a glass substrate and a transparent resin substrate.

The dielectric multilayer film is a film having the capability of reflecting and/or absorbing near-infrared rays.

As a material for the dielectric multilayer film, for example, ceramics can be used. In order to form a near-infrared cut-off filter for which the effect of light interference is used, it is preferably to use two or more kinds of ceramics having different refractive indexes.

Alternatively, a noble metal film that absorbs light in the near-infrared range is preferably used in consideration of the thickness and the number of layers so as to prevent the visible light transmissivity of the near-infrared cut-off filter from being affected.

As the dielectric multilayer film, specifically, it is possible to preferably use a configuration in which high-refractive index material layers and low-refractive index material layers are alternately laminated.

As a material that configures the high-refractive index material layer, a material having a refractive index of 1.7 or more can be used and a material having a refractive index in a range of 1.7 to 2.5 is generally selected.

Examples of the material include titanium oxide (titania), zirconium oxide, tantalum pentaoxide, niobium pentaoxide, lanthanum oxide, yttrium oxide, zinc oxide, zinc sulfide, indium oxide, and materials which contain the above-described oxide as a main component and contain a small amount of titanium oxide, zinc oxide, and/or cerium oxide. Among these, titanium oxide (titania) is preferred.

As a material configuring the low-refractive index material layer, it is possible to use a material having a refractive index of 1.6 or less and a material having a refractive index in a range of 1.2 to 1.6 is generally selected.

Examples of the material include silica, alumina, lanthanum fluoride, magnesium fluoride, and sodium aluminum hexafluoride. Among these, silica is preferred.

The thickness of each of the high-refractive index layer and the low-refractive index layer is generally as thick as $0.1\lambda$ to $0.5\lambda$ of the wavelength $\lambda$ (nm) of an infrared ray which is planned to be shielded. When the thickness is outside the above-described range, the product (n×d) of the refractive index (n) and the film thickness (d) is significantly different from the optical film thickness computed using $\lambda/4$ and thus the optical characteristic relationship between reflection and refraction is no longer valid, and there is a tendency that it becomes difficult to control the shielding and transmitting of specific wavelengths.

In addition, the number of layers laminated in the dielectric multilayer film is preferably in a range of 5 to 50 and more preferably in a range of 10 to 45.

There is no particular limitation regarding the method for forming the dielectric multilayer film and examples thereof include a method in which a dielectric multilayer film in which high-refractive index layers and low-refractive index layers are alternately laminated is formed using a CVD method, a sputtering method, a vacuum deposition method, or the like and is attached to the film using an adhesive and a method in which a dielectric multilayer film in which high-refractive index layers and low-refractive index layers are alternately laminated is directly formed on the film using a CVD method, a sputtering method, a vacuum deposition method, or the like.

Furthermore, in a case in which a substrate is warped during the deposition of the dielectric multilayer film, in order to prevent the above-described warping, it is possible to employ a method in which the dielectric multilayer films are deposited on both surfaces of the substrate or the surface of the substrate on which the dielectric multilayer film is deposited is irradiated with a radioactive ray such as an infrared ray. Meanwhile, in a case in which the surface is irradiated with a radioactive ray, the surface may be irradiated with a radioactive ray while the dielectric multilayer film is deposited or the surface may be separately irradiated with a radioactive ray after the dielectric multilayer film is deposited.

The present invention also relates to a near-infrared cut-off filter obtained using the above-described near-infrared-absorbing composition of the present invention and a near-infrared cut-off filter including the laminate. Since the above-described near-infrared cut-off filter is formed using the near-infrared-absorbing composition of the present invention, the near-infrared cut-off filter has high light shielding properties (near-infrared shielding properties) in the near-infrared range, high translucency in the visible light range (visible light permeability), and excellent weather resistance such as light resistance and moisture resistance. Particularly, in the present invention, the near-infrared cut-off filter is advantageous as a near-infrared cut-off filter in a wavelength range of 700 nm to 2500 nm.

In addition, the present invention also relates to a near-infrared cut-off filter including a transparent supporter, a near-infrared cut-off layer obtained by curing the near-infrared-absorbing composition including a copper complex having the maximum absorption wavelength in the near-infrared absorption range, and a dielectric multilayer film. The copper complex having the maximum absorption wavelength in the near-infrared absorption range is identical to the copper complex for which the near-infrared-absorbing composition of the present invention and the preferred range is also identical.

Furthermore, the present invention also relates to a method for producing a near-infrared cut-off filter including a step of applying (preferably coating or printing and more preferably applicator-coating) the near-infrared-absorbing composition of the present invention to the light-receiving side of a solid-state imaging element substrate so as to form a film.

In order to form the near-infrared cut-off filter, first, a film is formed using the near-infrared-absorbing composition of the present invention. The film is not particularly limited as long as the film includes the near-infrared-absorbing composition and the film thickness, the laminate structure, and the like can be appropriately selected depending on the purpose.

Examples of the method for forming the film include a method in which the near-infrared-absorbing composition of the present invention (a coating fluid obtained by dissolving, emulsifying, or dispersing the solid content in the composition in the solvent) is directly applied (preferably coated) and dried.

A supporter may be a transparent substrate made of glass, a solid-state imaging element substrate, another substrate (for example, a glass substrate 30 described below) provided on the light-receiving side of the solid-state imaging element substrate, or a layer such as a flattened layer provided on the light-receiving side of the solid-state imaging element substrate.

The near-infrared-absorbing composition (coating fluid) can be applied onto the supporter using, for example, a spin coater, a slit spin coater, a slit coater, screen printing, applicator application, or the like.

In addition, the conditions for drying the coated film vary depending on the kind and fractions of individual components and a solvent; however, generally, the coated film is dried at a temperature in a range of 60° C. to 150° C. for approximately 30 seconds to 15 minutes.

The thickness of the film is not particularly limited and can be appropriately selected depending on the purpose. The thickness of the film is, for example, preferably in a range of 1 μm to 500 μm, more preferably in a range of 1 μm to 300 μm, and particularly preferably in a range of 1 μm to 200 μm.

A method for forming the near-infrared cut-off filter using the near-infrared-absorbing composition of the present invention may include other steps. The other steps are not particularly limited and can be appropriately selected depending on the purpose. Examples thereof include a surface treatment step of the base material, a pretreatment step (prebaking step), a curing treatment step, a post heating step (post baking step), and the like.

<Preheating Step and Post Heating Step>

The heating temperatures in the preheating step and the post heating step are generally in a range of 80° C. to 200° C. and preferably in a range of 90° C. to 150° C.

The heating times in the preheating step and the post heating step are generally in a range of 30 seconds to 240 seconds and preferably in a range of 60 seconds to 180 seconds.

<Curing Treatment Step>

The curing treatment step refers to a step of carrying out a curing treatment on the formed film as necessary and the curing treatment improves the mechanical strength of the near-infrared cut-off filter.

The curing treatment step is not particularly limited and can be appropriately selected depending on the purpose and preferred examples thereof include a full-surface exposure treatment, a full-surface thermal treatment, and the like. In the present invention, the meaning of "exposure" includes the irradiation of the surface with a radioactive ray such as an electron beam or an X ray as well as light rays having a variety of wavelengths.

The exposure is preferably carried out through irradiation using an radioactive ray and, as the radioactive ray that can be used in the exposure, particularly, an ultraviolet ray such as an electron beam, KrF, ArF, a g-ray, an h-ray, or an i-ray or visible light is preferably used. Preferably, KrF, a g-ray, an h-ray, and an i-ray are preferred.

Examples of the exposure method include stepper exposure, exposure using a high-pressure mercury lamp, and the like.

The exposure amount is preferably in a range of 5 J/cm$^2$ to 3000 mJ/cm$^2$, more preferably in a range of 10 J/cm$^2$ to 2000 mJ/cm$^2$, and particularly preferably in a range of 50 J/cm$^2$ to 1000 mJ/cm$^2$.

Examples of a method for the full-surface exposure treatment include a method in which the full surface of the above-described formed film is exposed. In a case in which the near-infrared-absorbing composition includes the polymerizing compound, the full-surface exposure accelerates the curing of a polymerizing component in the film formed of the composition, makes the film cured to a greater extent, and improves the mechanical strength and the durability.

An apparatus for carrying out the full-surface exposure is not particularly limited and can be appropriately selected depending on the purpose, and preferred examples thereof include UV steppers such as ultrahigh-pressure mercury lamps.

In addition, examples of the method for the full-surface thermal treatment include a method in which the full surface of the above-described formed film is heated. The heating of the full surface increases the film strength of a pattern.

The heating temperature during the full-surface heating is preferably in a range of 120° C. to 250° C. and more preferably in a range of 150° C. to 200° C. When the heating temperature is 120° C. or higher, the film strength is improved by the heating treatment and, when the heating temperature is 250° C. or lower, components in the film are decomposed and it is possible to prevent film qualities from becoming weak and brittle.

The heating time in the full-surface heating is preferably in a range of 3 minutes to 180 minutes and more preferably in a range of 5 minutes to 120 minutes.

An apparatus for carrying out the full-surface heating is not particularly limited and can be appropriately selected from well-known apparatuses depending on the purpose, and examples thereof include a dry oven, a hot plate, an IR heater, and the like.

The present invention also relates to a camera module including a solid-state imaging element substrate and a near-infrared cut-off filter disposed on the light-receiving side of the solid-state imaging element substrate, in which the near-infrared cut-off filter is the near-infrared cut-off filter of the present invention.

Hereinafter, a camera module according to an embodiment of the present invention will be described with reference to FIGS. 1 and 2, but the present invention is not limited by specific examples described below.

Figure 2:
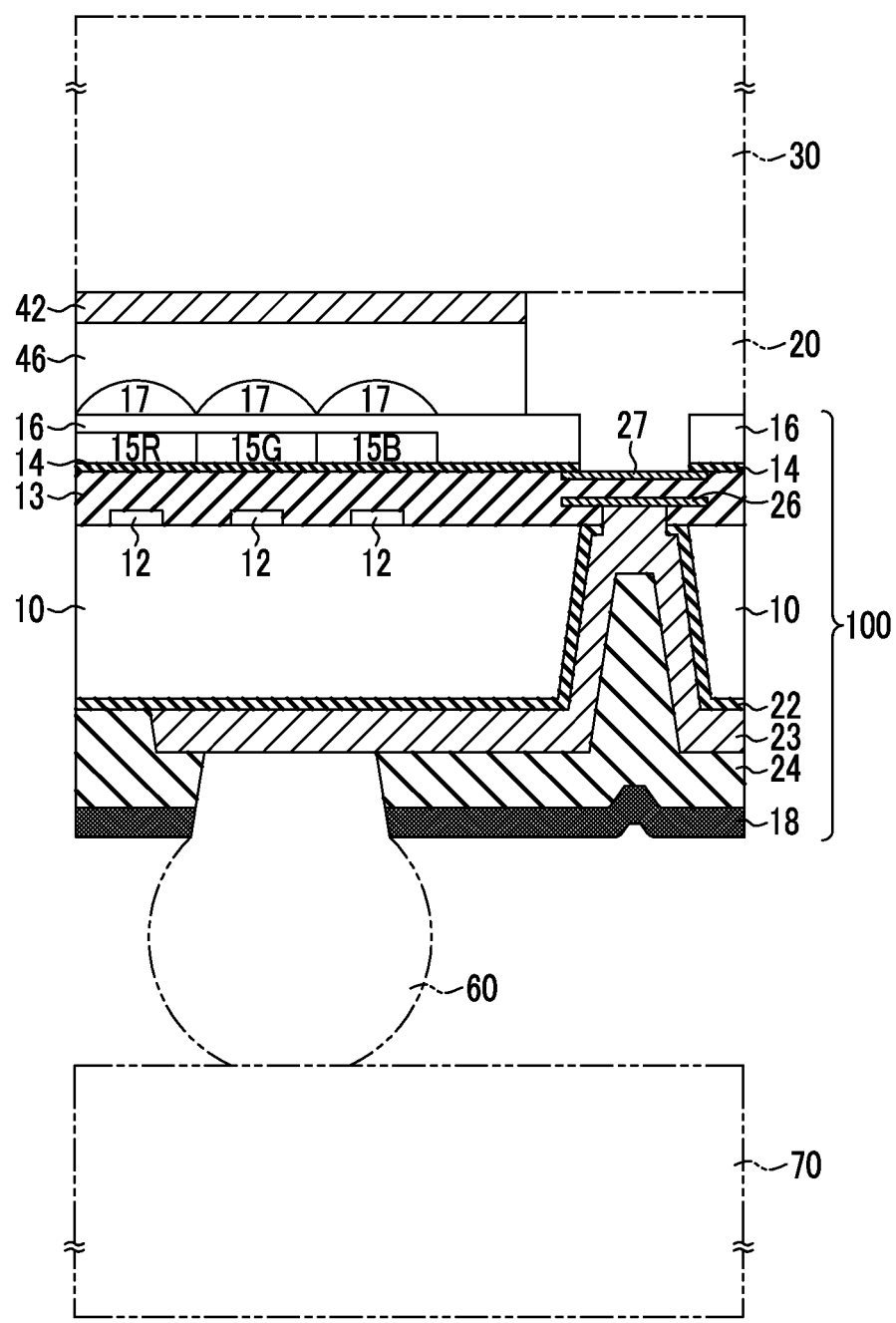
FIG. 2 is a schematic sectional view of a solid-state imaging element substrate according to the embodiment of the present invention.

In FIGS. 1 and 2, common portions are given common reference signs.

In addition, in the description, "upper", "upward", and "upper side" indicate the side far from a silicon substrate 10 and "lower", "downward", and "lower side" indicate the side close to the silicon substrate 10.

FIG. 1 is a schematic sectional view illustrating the configuration of a camera module including a solid-state imaging element.

A camera module 200 illustrated in FIG. 1 is connected to a circuit board 70 which is a mounting board through solder balls 60 that are connection members.

In detail, the camera module 200 includes a solid-state imaging element substrate 100 having an imaging element section on a first main surface of a silicon substrate, a flattening layer provided on the first main surface side (light-receiving side) of the solid-state imaging element substrate 100 (not illustrated in FIG. 1), a near-infrared cut-off filter 42 provided on the flattening layer, a lens holder 50 which is disposed above the near-infrared cut-off filter 42 and includes an imaging lens 40 in the inner space, and a light shielding and electromagnetic shield 44 disposed so as to surround the peripheries of the solid-state imaging element substrate 100 and a glass substrate 30. The glass substrate 30 (light transmissive substrate) may be provided on the flattening layer. The respective members are adhered using adhesives 20 and 45.

The present invention also relates to a step of forming a film by applying the near-infrared-absorbing composition of the present invention to the light-receiving side of the solid-state imaging element substrate in a method for manufacturing the camera module including the solid-state imaging element substrate and the near-infrared cut-off filter disposed on the light-receiving side of the solid-state imaging element substrate.

Therefore, in the camera module according to the present embodiment, for example, the near-infrared cut-off filter 42 can be formed by applying the near-infrared-absorbing composition of the present invention so as to form a film on the flattening layer. A method for applying the near-infrared cut-off filter is as described above.

In the camera module 200, incident light hv coming from the outside sequentially passes through the imaging lens 40, the near-infrared cut-off filter 42, the glass substrate 30, and the flattening layer and then reaches the imaging element section in the solid-state imaging element substrate 100. In addition, the camera module 200 is connected to the circuit board 70 through the solder balls 60 (connection material) on a second main surface side of the solid-state imaging element substrate 100.

The camera module 200 may include the near-infrared cut-off filter directly provided on the flattening layer without the glass substrate 30 or may include the near-infrared cut-off filter directly provided on the glass substrate 30 without the flattening layer.

FIG. 2 is an enlarged view of the solid-state imaging element substrate 100 in FIG. 1.

The solid-state imaging element substrate 100 includes the silicon substrate 10 which is a basic body, imaging elements 12, an interlayer insulating film 13, a base layer 14, a red color filter 15R, a green color filter 15G, a blue color filter 15B, an overcoat 16, micro lenses 17, a light-shielding film 18, an insulating film 22, a metal electrode 23, a solder resist layer 24, an internal electrode 26, and an element surface electrode 27.

Here, the solder resist layer 24 may not be provided.

Regarding the solid-state imaging element substrate 100, the description of the solid-state imaging element substrate 100 in Paragraphs <0245> <0407> in the specification of the corresponding US2012/068292A) and thereafter in JP2012-068418A can be referenced and the content thereof is incorporated into the specification of the present application by reference.

Thus far, the embodiment of the camera module has been described with reference to FIGS. 1 and 2, but the embodiment is not limited to the aspect of FIGS. 1 and 2.

EXAMPLES

Hereinafter, the present invention will be more specifically described using examples. Materials, amounts used, fractions, treatment contents, treatment orders, and the like described in the following examples can be appropriately changed within the scope of the gist of the present invention. Therefore, the scope of the present invention is not limited to specific examples described below.

In the present examples, the following abbreviations will be employed.

<Sulfonic Acid>

In Table 20 described below, for example, the organic group (—$CH_3$) of A-1 represents R in the general formula described below. In addition, for example, "*" in the organic group of A-13 represents a bonding portion with a sulfur atom in the general formula described below.

TABLE 20

$$R-\underset{\underset{O}{\|}}{\overset{\overset{O}{\|}}{S}}-OH$$

| Sulfonic acid | R |
|---|---|
| A-1 | —$CH_3$ |
| A-2 | —$CH_2CH_3$ |
| A-13 | *–(CH₂)₆–CH₃ (n-heptyl chain) |
| A-62 | *–C₆H₄–$CH_3$ (p-tolyl) |
| A-74 | *–(3,5-dimethylphenyl) |
| A-77 | *–(3,4,5-trimethylphenyl) |
| A-82 | *–C₆F₅ (pentafluorophenyl) |
| A-91 | *–(2-(methoxycarbonyl)phenyl), $H_3COOC$ |
| A-96 | —$CF_3$ |

TABLE 20-continued $$R-\underset{\underset{O}{\|}}{\overset{\overset{O}{\|}}{S}}-OH$$

| Sulfonic acid | R |
|---|---|
| A-105 | (camphor-derived bicyclic ketone group) |
| A-107 | allyl (*-CH$_2$-CH=CH$_2$) |
| A-111 | *-CH$_2$CH$_2$CH$_2$-O-C(=O)-C(CH$_3$)=CH$_2$ |
| A-112 | *-CH$_2$-C(CH$_3$)$_2$-NH-C(=O)-CH=CH$_2$ |
| A-113 | *-(p-C$_6$H$_4$)-CH=CH$_2$ |

<Polymerizing Compound>

NK ester ATM-35E: ethyleneoxy-denatured pentaerythritol tetraacrylate (polymerizing compound) (manufactured by Shin-Nakamura Chemical Co., Ltd.)

JER157S65: epoxy resin (manufactured by Japan Epoxy Resin Co., Ltd.)

EX-321: epoxy resin (manufactured by Nagase ChemteX Corporation)

KAYARAD D-320: (manufactured by Nippon Kayaku Co., Ltd., dipentaerythritol tetraacrylate)

M-510: (manufactured by Toagosei Co., Ltd., polybasic acid-denatured acryl oligomer)

M-520: (manufactured by Toagosei Co., Ltd., polybasic acid-denatured acryl oligomer)

DPCA-60: (manufactured by Nippon Kayaku Co., Ltd., hexafunctional acrylate having six penthyleneoxy chains)

<Solvent>

PGME: Propylene glycol monomethyl ether
PGMEA: Propylene glycol monomethyl ether acetate <Synthesis Example of Sulfonic Acid Copper Compound 1>

Sulfonic acid (A-1) (1.239 g, 12.89 mmol) and sulfonic acid (A-2) (1.420 g, 12.89 mmol) were weighed and methanol (45 g) was added and dissolved. Copper acetate (0.5 equivalent weights, 2.341 g, 12.89 mmol) was added to the total amount of the sulfonic acids, the components were heated to 50° C. and were reacted for 2 hours. After the end of the reaction, the generated acetic acid and the solvent were distilled away using an evaporator, thereby obtaining a sulfonic acid copper complex 1 (4.62 g).

<Synthesis Example of Sulfonic Acid Copper Complex 9>

Sodium ethanesulfonate (1.193 g, 9.03 mmol) and sodium trifluoromethanesulfonate (1.553 g, 9.03 mmol) were weighed and ethanol (45 g) was added and dissolved. Copper sulfate pentahydrate (0.5 equivalent weights, 2.254 g, 9.03 mmol) was added to the total amount of the sulfonic acids, the components were heated to 50° C. and were reacted for 2 hours. After the end of the reaction, the solvent was distilled away using an evaporator and sodium sulfate (5.00 g) was added. Tetrahydrofuran was added, insoluble components were removed through celite filtration, and the solvent was distilled away using an evaporator, thereby obtaining a sulfonic acid copper complex 9 (3.27 g).

<Synthesis Example of Sulfonic Acid Copper Complexes 2 to 8 and 10 to 23>

Additional sulfonic acid copper complexes 2 to 8 and 10 to 30 were obtained using the same method as in the above-described synthesis examples except for the fact that the kinds of the sulfonic acids or the molar ratios of the sulfonic acids were changed.

(Evaluation Methods)

<Evaluation of Near-Infrared-Absorbing Composition>

<<Preparation of Near-Infrared-Absorbing Composition>>

The following compounds were mixed, thereby preparing near-infrared-absorbing compositions of examples and comparative examples.

Sulfonic acid copper complex described in Table 21 below
  40 parts by mass
NK ester ATM-35E 40 parts by mass
PGME 120 parts by mass <Production of Near-Infrared Cut-Off Filter>

Each of the near-infrared-absorbing compositions prepared in the examples and the comparative examples was applicator-applied onto a glass substrate using an applicator coating method (baker applicator manufactured by Yoshimits Seiki Co., Ltd., used after a YBA-3 type was adjusted to a slit width of 250 μm) and was prebaked at 100° C. for 120 seconds. After that, all the samples were heated at 180° C. for 180 seconds using a hot plate, thereby obtaining near-infrared cut-off filters.

<<Evaluation of Solubility>>

Each of the sulfonic acid copper complexes (0.5 g) was weighed in a test tube, PGME was added so that the solid content concentration reached 50 mass %, 40 mass %, and 30 mass %, and the components were shaken for 10 minutes. The solid content concentrations at which the solution became visually turbid were evaluated on the basis of the following standards. The results are described in Table 21.

A: The solution did not become turbid
B: The solid content concentration was 50 mass %
C: The solid content concentration was 40 mass %
D: The solid content concentration was 30 mass %

<<Evaluation of Near-Infrared Shielding Properties>>

The transmissivities at a wavelength of 800 nm of the near-infrared cut-off filters obtained as described above were measured using a spectrophotometer U-4100 (manufactured by Hitachi High-Technologies Corporation). The near-infrared shielding properties were evaluated on the basis of the following standards. The results are described in Table 21.

A: transmissivity at 800 nm ≤ 5%
B: 5% < transmissivity at 800 nm ≤ 7%
C: 7% < transmissivity at 800 nm ≤ 10%
D: 10% < transmissivity at 800 nm <<Evaluation of Heat Resistance>>

The near-infrared cut-off filters obtained as described above were left to stand at 200° C. for 30 minutes. The maximum absorbance (Absλmax) at a wavelength of 700 nm to 1400 nm and the minimum absorbance (Absλmin) at a wavelength of 400 nm to 700 nm were measured using a spectrophotometer U-4100 (manufactured by Hitachi High-Technologies Corporation) respectively before and after the moisture resistance test and the absorbance ratios represented by "Absλmax/Absλmin" were obtained.

The absorbance ratio change rates represented by |((the absorbance ratio before the test-the absorbance ratio after the test)/the absorbance ratio before the test)×100|(%) were evaluated on the basis of the following standards. The results are described in the following tables.

A: absorbance ratio change rate≤2%
B: 2%<absorbance ratio change rate≤4%
C: 4%<absorbance ratio change rate≤7%
D: 7%<absorbance ratio change rate It was confirmed that even the near-infrared cut-off filters of Examples 31 to 38 had favorable near-infrared shielding properties.

TABLE 22

|  | Polymerizing compound | Solvent |
|---|---|---|
| Example 31 | KAYARAD D-320 (40 parts by mass) | PGME (120 parts by mass) |
| Example 32 | M-510 (40 parts by mass) | PGME (120 parts by mass) |
| Example 33 | M-520 (40 parts by mass) | PGME (120 parts by mass) |
| Example 34 | DPCA-60 (40 parts by mass) | PGME (120 parts by mass) |

TABLE 21

|  | Sulfonic acid | | | | | Near-infrared | | |
|---|---|---|---|---|---|---|---|---|
|  | Compound i | Compound ii | Compound iii | Compound iv | i:ii::iii:iv [molar ratio] | Sulfonic acid copper complex | Solubility | shielding properties | Heat resistance |
| Example 1 | A-1 | A-2 | | | 1:1:0:0 | 1 | C | A | A |
| Example 2 | A-2 | A-13 | | | 1:1:0:0 | 2 | C | A | A |
| Example 3 | A-2 | A-62 | | | 1:1:0:0 | 3 | C | A | B |
| Example 4 | A-2 | A-74 | | | 1:1:0:0 | 4 | B | A | B |
| Example 5 | A-2 | A-77 | | | 1:1:0:0 | 5 | B | A | B |
| Example 6 | A-2 | A-82 | | | 1:1:0:0 | 6 | B | A | B |
| Example 7 | A-2 | A-91 | | | 1:1:0:0 | 7 | B | A | A |
| Example 8 | A-2 | A-96 | | | 1:1:0:0 | 8 | B | A | A |
| Example 9 | A-2 (Na salt) | A-96 (Na salt) | | | 1:1:0:0 | 8 | B | A | B |
| Example 10 | A-2 | A-105 | | | 1:1:0:0 | 9 | B | A | A |
| Example 11 | A-2 | A-107 | | | 1:1:0:0 | 10 | B | A | B |
| Example 12 | A-2 | A-111 | | | 1:1:0:0 | 11 | B | A | B |
| Example 13 | A-2 | A-112 | | | 1:1:0:0 | 12 | B | A | B |
| Example 14 | A-2 | A-113 | | | 1:1:0:0 | 13 | B | A | B |
| Example 15 | A-2 | A-13 | A-62 | | 1:1:1:0 | 14 | A | A | B |
| Example 16 | A-2 | A-52 | A-105 | | 1:1:1:0 | 15 | A | A | A |
| Example 17 | A-2 | A-52 | A-107 | | 1:1:1:0 | 16 | A | A | A |
| Example 18 | A-2 | A-52 | A-107 | | 1:1:3:0 | 17 | A | A | B |
| Example 19 | A-2 | A-52 | A-112 | | 1:1:1:1 | 18 | A | A | B |
| Example 20 | A-2 | A-13 | A-62 | A-105 | 1:1:1:1 | 19 | A | A | BA |
| Example 21 | A-2 | A-13 | A-62 | A-107 | 1:1:1:3 | 20 | A | A | A |
| Example 22 | A-2 | A-13 | A-62 | A-107 | 1:1:1:1 | 21 | A | A | B |
| Example 23 | A-2 | A-13 | A-62 | A-112 | 1:0:0:0 | 22 | A | A | A |
| Example 24 | A-1 | | | | 1:0:0:0 | 23 | D | A | A |
| Example 25 | A-13 | | | | 1:0:0:0 | 24 | D | A | A |
| Example 26 | A-77 | | | | 1:0:0:0 | 25 | C | A | B |
| Example 27 | A-105 | | | | 1:0:0:0 | 29 | C | A | B |
| Example 28 | A-107 | | | | 1:0:0:0 | 27 | D | A | A |
| Example 29 | A-112 | | | | 1:0:0:0 | 28 | D | A | B |
| Example 30 | A-113 | | | | 1:0:0:0 | 29 | D | A | B |

As is clear from Table 21, the near-infrared-absorbing compositions of the examples were capable of forming cured films having excellent heat resistance while maintaining strong near-infrared shielding properties when the cured films were produced.

In addition, since near-infrared-absorbing compositions of Examples 15 to 23 were obtained by reacting three or more kinds of sulfonic acids, it is possible to further improve the solubility of the copper complex in a solvent while maintaining strong near-infrared shielding properties when the cured films were produced.

Examples 31 to 38

Near-infrared cut-off filters of Examples 31 to 38 were obtained in the same manner as in Example 1 except for the fact that, in the near-infrared-absorbing composition of Example 1, the polymerizing compound (NK ester ATM-35E) or the solvent (PGME) was changed to the polymerizing compounds or the solvents in Table 22 described below.

TABLE 22-continued

|  | Polymerizing compound | Solvent |
|---|---|---|
| Example 35 | NK ester ATM-35E (20 parts by mass) and JER157S65 (20 parts by mass) | PGME (120 parts by mass) |
| Example 36 | JER157S65 (40 parts by mass) | PGME (120 parts by mass) |
| Example 37 | EX-321 (40 parts by mass) | PGME (120 parts by mass) |
| Example 38 | NK ester ATM-35E (40 parts by mass) | PGMEA (120 parts by mass) |

Example 39

The following compounds were mixed together at blending amounts described below, thereby preparing a near-infrared-absorbing composition of Example 39.

Copper complex A (copper complex having the following sulfophthalic acid as a ligand) 10 parts by mass
Polymerizing compound (NK ester ATM-35E) 10 parts by mass
Solvent (water) 10 parts by mass

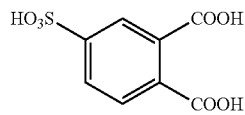

The copper complex A was synthesized as described below.

A 53.1% aqueous solution of sulfophthalic acid (13.49 g, 29.1 mmol) was dissolved in methanol (50 mL), the solution was heated to 50° C., then, copper hydroxide (2.84 g, 29.1 mmol) was added, and the components were reacted at 50° C. for 2 hours. After the end of the reaction, the solvent and the generated water were distilled away using an evaporator, thereby obtaining a copper complex A (8.57 g).

Example 40

The following compounds were mixed together at blending amounts described below, thereby preparing a near-infrared-absorbing composition of Example 40.

Copper complex A (copper complex having the above-described sulfophthalic acid as a ligand) 10 parts by mass
Binder described below 10 parts by mass
Solvent (water) 80 parts by mass
Binder: the following compound

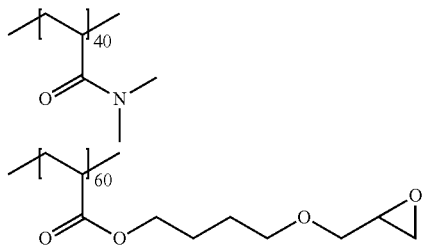

Examples 41 to 55

Near-infrared-absorbing compositions of Examples 41 to 55 were prepared in the same manner as in Example 39 except for the fact that, in the preparation of the near-infrared-absorbing composition of Example 39, copper complexes for which the compounds (ligand raw materials) described in Table 23 and copper hydroxide were reacted together were used as the copper complexes A.

In Table 23 described below, the ligand raw material (acid) indicates materials used to obtain the above-described copper complexes A. In addition, "-" indicates that the compound (ii) was not used.

TABLE 23

|  | Ligand raw material (acid) | | (i):(ii) [Molar ratio] | Acid group/ Cu ratio |
|---|---|---|---|---|
|  | Compound (i) | Compound (ii) | | |
| Example 41 | —SO₃H | ⌇⌇⌇SO₃H | 1:1 | 2/1 |
| Example 42 | CF₃—SO₃H | — | 1:0 | 2/1 |
| Example 43 | HO₃S—CF₂—CF₂—CF₂—SO₃H | — | 1:0 | 2/1 |
| Example 44 | 4-methylphenyl—SO₃H | — | 1:0 | 2/1 |
| Example 45 | HO₃S—CH₂CH₂—SO₃H | — | 1:0 | 2/1 |
| Example 46 | 2-COOH-phenyl—SO₃H | — | 1:0 | 4/1 |
| Example 47 | 2-COOH-phenyl—SO₃H | — | 1:0 | 2/1 |

TABLE 23-continued

| | Ligand raw material (acid) | | | |
|---|---|---|---|---|
| | Compound (i) | Compound (ii) | (i):(ii) [Molar ratio] | Acid group/ Cu ratio |
| Example 48 | HO₃S-C₆H₃(COOH)₂ | — | 1:0 | 6/1 |
| Example 49 | HO₃S-C₆H₃(COOH)₂ | — | 1:0 | 3/1 |
| Example 50 | HO₃S-C₆H₃(COOH)₂ | — | 1:0 | 2/1 |
| Example 51 | methacrylate-propyl-SO₃H | — | 1:0 | 2/1 |
| Example 52 | methoxyacetic acid | HO₃S-C₆H₃(COOH)₂ | 1:1 | 2/1 |
| Example 53 | methoxyacetic acid | HO₃S-C₆H₃(COOH)₂ | 3:1 | 2/1 |
| Example 54 | acryloyl-ethyl-succinate | HO₃S-C₆H₃(COOH)₂ | 1:1 | 2/1 |
| Example 55 | methacrylate-propyl-SO₃H | HO₃S-C₆H₃(COOH)₂ | 1:1 | 2/1 |

Near-infrared cut-off filters of Examples 39 to 41 were obtained in the same manner as in Example 1 using the near-infrared-absorbing compositions obtained in Examples 39 to 41.

It was confirmed that even the near-infrared cut-off filters of Examples 39 to 41 had favorable near-infrared shielding properties.

What is claimed is:

1. A near-infrared-absorbing composition, comprising:
a copper complex obtained by reacting two or more sulfonic acids represented by General Formula (I) described below or salts thereof with a copper component, General Formula (I)

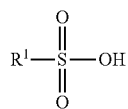

in Formula (I), R¹ represents an organic group.

2. A near-infrared-absorbing composition, comprising:
a copper complex which includes copper as a central metal and includes sulfonic acids represented by General Formula (I) described below having mutually different structures as ligands or a copper complex having structures represented by General Formula (II) described below that are different from each other; and
a solvent, General Formula (I)

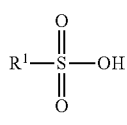

General Formula (II)

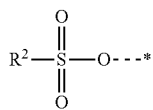

in Formula (I), $R^1$ represents an organic group, in Formula (II), $R^2$ represents an organic group, and "*" indicates a portion at which a coordination bond with copper is formed.

3. The near-infrared-absorbing composition according to claim 1,
wherein the $R^1$ is an alkyl group, an aryl group, or an organic group having an unsaturated double bond.

4. The near-infrared-absorbing composition according to claim 2,
wherein each of the $R^1$ and $R^2$ is independently an alkyl group, an aryl group, or an organic group having an unsaturated double bond.

5. The near-infrared-absorbing composition according to claim 1,
wherein the $R^1$ is an organic group having a molecular weight of 300 or less.

6. The near-infrared-absorbing composition according to claim 2,
wherein the $R^1$ and/or $R^2$ are organic groups having a molecular weight of 300 or less.

7. The near-infrared-absorbing composition according to claim 1,
wherein the sulfonic acid represented by General Formula (I) is selected from unsubstituted alkyl sulfonic acids, substituted or unsubstituted aryl sulfonic acids, alkyl sulfonic acids substituted with a fluorine atom, and substituted or unsubstituted alkenyl sulfonic acids.

8. The near-infrared-absorbing composition according to claim 2,
wherein the sulfonic acid represented by General Formula (I) is selected from unsubstituted alkyl sulfonic acids, substituted or unsubstituted aryl sulfonic acids, alkyl sulfonic acids substituted with a fluorine atom, and substituted or unsubstituted alkenyl sulfonic acids.

9. The near-infrared-absorbing composition according to claim 1,
wherein the copper complex is obtained by reacting three or more kinds of the sulfonic acids represented by General Formula (I) or salts thereof with the copper component.

10. The near-infrared-absorbing composition according to claim 2, further comprising:
three or more copper complexes which include the sulfonic acids represented by General Formula (I) having mutually different structures as ligands or three or more copper complexes having the structures represented by General Formula (II) that are different from each other.

11. The near-infrared-absorbing composition according to claim 2, further comprising:
a copper complex which includes the sulfonic acids represented by General Formula (I) all having the same structure as ligands or a copper complex having the structures represented by General Formula (II) that are identical to each other.

12. A near-infrared-absorbing composition, comprising:
a copper complex obtained by reacting sulfonic acids represented by General Formula (III) described below or salts thereof with a copper component;
a solvent; and
a curable compound,

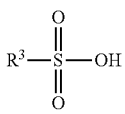

General Formula (III)

in Formula (III), $R^3$ represents an organic group having no (meth)acrylic ester group.

13. A near-infrared-absorbing composition, comprising:
a copper complex which includes copper as a central metal and includes sulfonic acids represented by General Formula (III) described below as ligands or a copper complex which has a structure represented by General Formula (IV) described below;
a solvent; and
a curable compound,

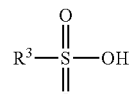

General Formula (III)

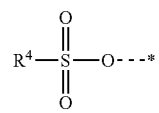

General Formula (IV)

in General Formula (III), $R^3$ represents an organic group having no (meth)acrylic ester group, in General Formula (IV), $R^4$ represents an organic group having no (meth)acrylic ester group, and "*" indicates a portion at which a coordination bond with copper is formed.

14. The near-infrared-absorbing composition according to claim 12,
wherein the $R^3$ is an alkyl group or an organic group having an aryl group.

15. The near-infrared-absorbing composition according to claim 13,
wherein each of the $R^3$ and $R^4$ is independently an alkyl group or an organic group having an aryl group.

16. The near-infrared-absorbing composition according to claim 12,
wherein the $R^3$ is an organic group having a molecular weight of 300 or less.

17. The near-infrared-absorbing composition according to claim 13,
wherein the $R^3$ and/or $R^4$ are organic groups having a molecular weight of 300 or less.

18. The near-infrared-absorbing composition according to claim 12,
wherein the sulfonic acid represented by General Formula (III) is selected from unsubstituted alkyl sulfonic acids, substituted or unsubstituted aryl sulfonic acids, alkyl sulfonic acids substituted with a fluorine atom, and substituted or unsubstituted alkenyl sulfonic acids.

19. The near-infrared-absorbing composition according to claim 13, further comprising:
two or more copper complexes which include sulfonic acids represented by General Formula (III) all having the same structure as ligands or two or more copper complexes having the structures represented by General Formula (IV) that are all identical to each other.

20. The near-infrared-absorbing composition according to claim 1, further comprising:
a curable compound.

21. The near-infrared-absorbing composition according to claim 20,
wherein the curable compound is a tri- or more-functional (meth)acrylate and/or an epoxy resin.

22. The near-infrared-absorbing composition according to claim 1, wherein a solid content of the near-infrared-absorbing composition is in a range of 35 mass % to 90 mass %.

23. The near-infrared-absorbing composition according to claim 1 which is used in a form of a coated film formed on an image sensor for a solid-state imaging element.

24. A near-infrared-absorbing composition, comprising:
a copper complex obtained by reacting a compound having two or more acid groups or salts thereof with a copper component; and
a curable compound.

25. The near-infrared-absorbing composition according to claim 24,
wherein the acid group included in the compound having two or more acid groups is selected from a sulfonic acid group, a carboxylic acid group, and acid groups including a phosphorous atom.

26. The near-infrared-absorbing composition according to claim 24,
wherein the compound having two or more acid groups includes at least a sulfonic acid group and a carboxylic acid group.

27. A near-infrared cut-off filter produced using the near-infrared-absorbing composition according to claim 1.

28. A camera module, comprising:
a solid-state imaging element substrate; and
the near-infrared cut-off filter according to claim 27 disposed on a light-receiving side of the solid-state imaging element substrate.

29. A method for manufacturing a camera module including a solid-state imaging element substrate and the near-infrared cut-off filter disposed on a light-receiving side of the solid-state imaging element substrate, comprising:
applying the near-infrared-absorbing composition according to claim 1 to the light-receiving side of the solid-state imaging element substrate to form a film.

30. A sulfonic acid copper complex mixture obtained by reacting two or more sulfonic acids represented by General Formula (I) described below or salts thereof with a copper component,

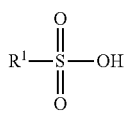

General Formula (I)

in Formula (I), $R^1$ represents an organic group.

31. A sulfonic acid copper complex mixture, comprising:
a sulfonic acid copper complex which includes copper as a central metal and includes sulfonic acids represented by General Formula (I) described below having mutually different structures as ligands or a sulfonic acid copper complex having structures represented by General Formula (II) described below that are different from each other; and a sulfonic acid copper complex which includes sulfonic acids represented by General Formula (I) described below all having the same structures as ligands or a sulfonic acid copper complex having the structures represented by General Formula (II) described below that are all identical to each other,

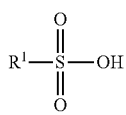

General Formula (I)

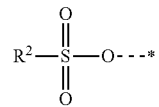

General Formula (II)

in General Formula (I), $R^1$ represents an organic group, in Formula (II), $R^2$ represents an organic group, and "*" indicates a portion at which a coordination bond with copper is formed.

32. A sulfonic acid copper complex obtained by reacting two or more sulfonic acids represented by General Formula (III) described below or salts thereof with a copper component, a sulfonic acid copper complex which includes copper as a central metal and includes two or more sulfonic acids represented by General Formula (III) described below as a ligand, or a sulfonic acid copper complex having two or more structures represented by General Formula (IV) described below,

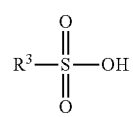

General Formula (III)

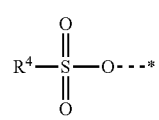

General Formula (IV)

in Formula (III), $R^3$ represents an organic group having no (meth)acrylic ester group, and, in Formula (IV), $R^4$ represents an organic group having no (meth)acrylic ester group and "*" indicates a portion at which a coordination bond with copper is formed.

33. The sulfonic acid copper complex according to claim 32,
wherein the sulfonic acid copper complex is a sulfonic acid copper complex mixture including two or more sulfonic acid copper complexes which include sulfonic acids represented by General Formula (III) all having the same structures as ligands or two or more sulfonic acid copper complexes having structures represented by General Formula (IV) that are all identical to each other.

34. The near-infrared-absorbing composition according to claim 12,
wherein the curable compound has a polymerizable group.

35. The near-infrared-absorbing composition according to claim 12,
wherein the curable compound is a polyfunctional (meth)acrylate.

36. The near-infrared-absorbing composition according to claim 12,
wherein the curable compound is an epoxy resin.

37. The near-infrared-absorbing composition according to claim 12,
wherein the curable compound is a polyfunctional epoxy resin.

38. The near-infrared-absorbing composition according to claim 12, wherein the curable compound is a polybasic-denatured acrylic oligomer.

39. The near-infrared-absorbing composition according to claim 12,
wherein the copper complex is obtained by reacting two or more sulfonic acids represented by General Formula (III) or salts thereof with a copper component.

40. The near-infrared-absorbing composition according to claim 12,
wherein the $R^3$ has a molecular weight in a range of 60 to 100.

41. The near-infrared-absorbing composition according to claim 12,
wherein the $R^3$ represents an alkyl group having no (meth)acrylic ester group or a heteroaryl group having no (meth)acrylic ester group.

42. The near-infrared-absorbing composition according to claim 13,
wherein the curable compound has a polymerizable group.

43. The near-infrared-absorbing composition according to claim 13,
wherein the curable compound is a polyfunctional (meth)acrylate.

44. The near-infrared-absorbing composition according to claim 13,
wherein the curable compound is an epoxy resin.

45. The near-infrared-absorbing composition according to claim 13,
wherein the curable compound is a polyfunctional epoxy resin.

46. The near-infrared-absorbing composition according to claim 13,
wherein the curable compound is a polybasic-denatured acrylic oligomer.

47. The near-infrared-absorbing composition according to claim 13,
wherein the copper complex includes copper as a central metal and includes two or more sulfonic acids represented by General Formula (III) as ligands or the copper complex has two or more structures represented by General Formula (IV).

48. The near-infrared-absorbing composition according to claim 13,
wherein the $R^3$ and/or $R^4$ have a molecular weight in a range of 60 to 100.

49. The near-infrared-absorbing composition according to claim 13,
wherein the $R^3$ and/or $R^4$ represent an alkyl group having no (meth)acrylic ester group or a heteroaryl group having no (meth)acrylic ester group.

50. The near-infrared-absorbing composition according to claim 24,
wherein the curable compound has a polymerizable group.

51. The near-infrared-absorbing composition according to claim 24,
wherein the curable compound is a polyfunctional (meth)acrylate.

52. The near-infrared-absorbing composition according to claim 24,
wherein the curable compound is an epoxy resin.

53. The near-infrared-absorbing composition according to claim 24,
wherein the curable compound is a polyfunctional epoxy resin.

54. The near-infrared-absorbing composition according to claim 24,
wherein the curable compound is a polybasic-denatured acrylic oligomer.

55. The near-infrared-absorbing composition according to claim 24,
wherein the copper complex is obtained by reacting a compound having three or more acid groups or salts thereof with a copper component.

56. The near-infrared-absorbing composition according to claim 24,
wherein the copper complex is obtained by reacting a compound having two or more carboxylic acid groups or salts thereof with a copper component.

57. The near-infrared-absorbing composition according to claim 32,
wherein the $R^3$ and/or $R^4$ have a molecular weight in a range of 60 to 100.

58. The near-infrared-absorbing composition according to claim 32,
wherein the $R^3$ and/or $R^4$ represent an alkyl group having no (meth)acrylic ester group or a heteroaryl group having no (meth)acrylic ester group.

* * * * *